(12) United States Patent
Jobling et al.

(10) Patent No.: US 6,956,148 B1
(45) Date of Patent: Oct. 18, 2005

(54) NUCLEIC ACIDS FROM CASSAVA ENCODING STARCH BRANCHING ENZYME II (SBEII) AND THEIR USE

(75) Inventors: Stephen A. Jobling, Huntingdon (GB); Richard Safford, Bedfordshire (GB)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 0 days.

(21) Appl. No.: 09/297,703

(22) PCT Filed: Nov. 4, 1997

(86) PCT No.: PCT/GB97/03032
§ 371 (c)(1),
(2), (4) Date: Jul. 19, 1999

(87) PCT Pub. No.: WO98/20145
PCT Pub. Date: May 14, 1998

(30) Foreign Application Priority Data

Nov. 5, 1996 (GB) .............................................. 9623095

(51) Int. Cl.[7] .............................. A01H 5/00; A01H 1/00; C12N 15/82; C12N 15/54
(52) U.S. Cl. ....................... 800/298; 536/23.2; 800/284
(58) Field of Search ................................. 800/284, 298, 800/278, 286, 320, 317.2, 317.4, 320.1, 320.2; 536/23.2, 23.6; 435/418, 468, 101, 411, 412, 417, 419

(56) References Cited

FOREIGN PATENT DOCUMENTS

| WO | WO 92/11375 | * | 7/1992 |
|----|-------------|---|--------|
| WO | WO 94/11520 A | * | 5/1994 |
| WO | WO 95/26407 | * | 10/1995 |
| WO | WO 96/34968 A | * | 11/1996 |
| WO | WO 97/20040 A | * | 6/1997 |
| WO | WO 97/22703 A | * | 6/1997 |

OTHER PUBLICATIONS

Hill et al, "Functional Analysis of Conserved Histidines in ADP–Glucose Prophosphorylase from *Escherichia coli*", 1998, Biochemical and Biophysical Research Communications vol. 244 pp. 573–577.*
Broun et al, "Catalytic Plasticity of Fatty Acid Modification Enzymes Underlying Chemical Diversity of Plant Lipids", 1998, Science vol. 282 pp. 1315–1317.*
Bowie et al, "Diciphering the Message in Protein Sequences: Tolerance to Amino Acid Substitutions", 1990, Science vol. 247, pp. 1306–1310.*
Lazar et al, "Transforming Growth Factor x: Mutation of Aspartic Acid 47 and Leucine 48 Results in Different Biological Activities", 1988, Molecular and Cellular Biology vol. 8 No. 3 pp. 1247–1252.*

Tang et al, "Antisense Repression of Vacuolar and Cell Wall Invertase in Transgenic Carrot Alters Early Plant Devleopment and Sucrose Partitiong", 1999, The Plant Cell, vol. 11 pp. 177–189.*
Colliver et al, "Differential modification of flavonoid and isflavonoid biosynthesis with an antisense chalcone synthase construct in transgenic *Lotus corniculatus*", 1997, Plant Molecular Biology vol. 35 pp. 509–522.*
Kuipers et al, "Factors affecting the inhibition by antisense RNA of granule–bound starch synthase gene expression in potato", 1995, Mol Gen Genet vol. 246, pp. 745–755.*
Bird et al, "Using antisense RNA to study gene function: inhibition of carotenoid biosynthesis in transgenic tomatoes", 1991, Bio/technology vol.. 9 pp. 635–639.*
van der Krol et al "Inhibition of flower pigmentation by antisense CHS genese: promoter and minimal sequence requirements for the antisense effect", 1990, Plant Molecular Biology vol. 14 pp. 457–466.*
Klann et al, "Antisense Acid Invertase (TIV1) Gene Alters Soluble Sugar Composition and Size in Transgenic Tomato Fruit", 1996, Plant Physiol. vol. 112: 1321–1330.*
Jobling et al, "A minor form of starch branching enzyme in potato (*Solanum tuberosum* L.) tubers has a major effect on starch structure: cloning and characterization of multiple forms of SBE A", 1999, The Plant Journal vol. 18(2) pp. 163–171.*
Burton et al, "Strach branching enzymes belonging to distinct enzyme families are differentialy expressed during pea embryo development", 1995, The Plant Journal, vol. 7(1) pp. 3–15.*
Kossman et al, Transgenic plants as tool to understand starch biosynthesis, 1995, Progress in Biotechnol. 10 (Carbohydrate Bioengineering 271–278.*
Fisher et al, "Two Closely related cDNAs encoding starch branching enzyme from *Arabidopsis thaliana*" 1996, Plant Molecular Biology vol. 30 pp. 97–108.*
Fisher et al, GenBank Accession No. U22428, 1996.*
Gao, M. et al., Independent Genetic Control of Maize Starch–Branching Enzymes IIa and IIb, Plant Physiology, vol. 114, No. 1, 1997, pp. 69–78.*
Burton, R.A., et al., "Starch Branching Enzymes Belonging to Distinct Enzyme Families are Differentially Expressed During Pea Embryo Development", EMBL Sequence Data Library, Jul. 6, 1994; Accession No. G10545.*

(Continued)

* cited by examiner

*Primary Examiner*—Anne Kubelik
(74) *Attorney, Agent, or Firm*—Karen G. Kaiser

(57) ABSTRACT

This invention provides isolated cassava nucleic acids encoding starch branching enzyme II (SBEII); constructs, vectors and host cells comprising the nucleic acids; and methods of using the nucleic acids to alter gene expression in cassava to obtain starch with altered properties.

10 Claims, 33 Drawing Sheets

OTHER PUBLICATIONS

Figure 1:
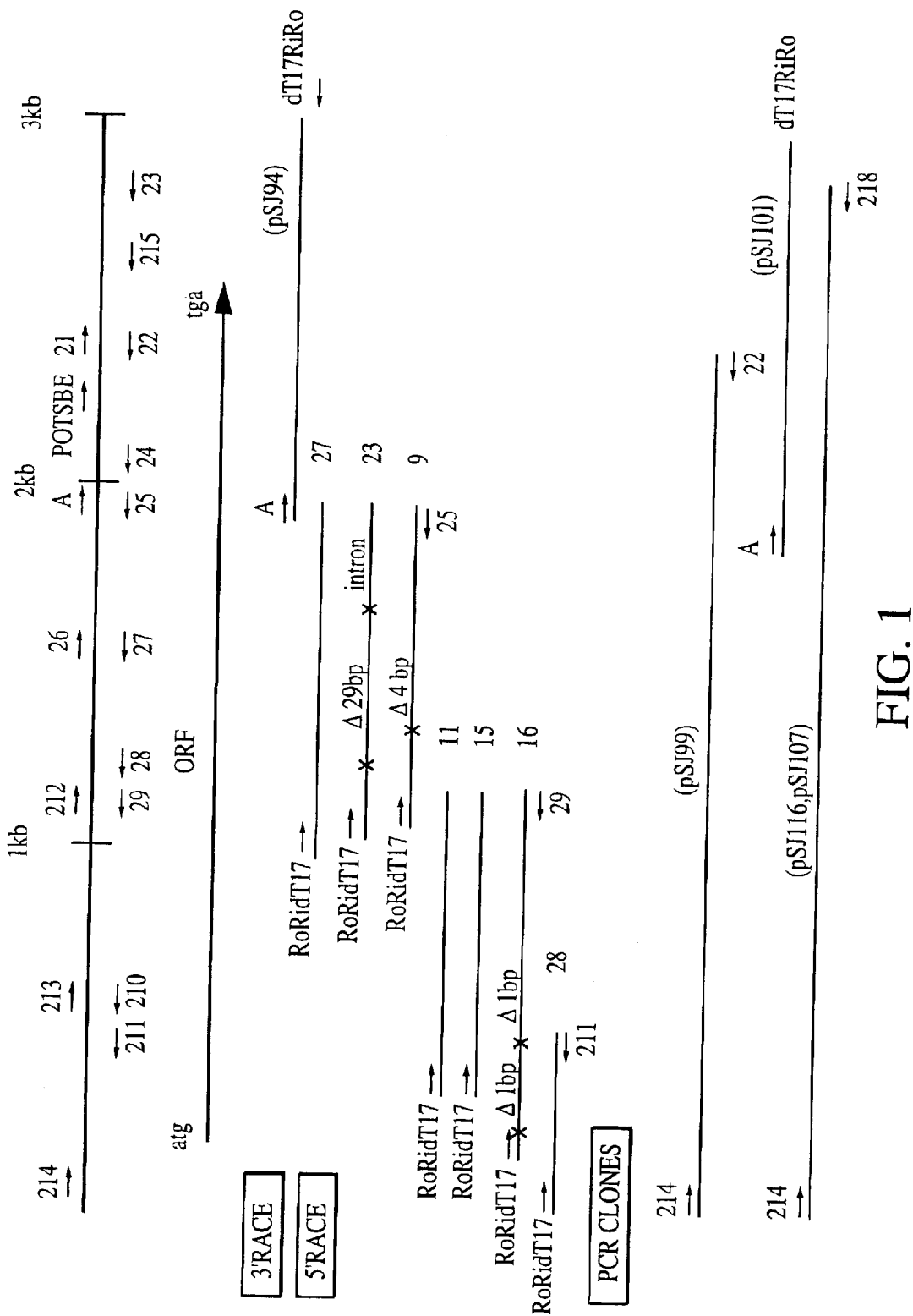

Fisher, D.K., "Two Closely Related cDNAs Encoding Starch Branching Enzyme from *Arabidopsis thaliana*", Plant Molecular Biology, vol. 30, 1996, pp. 97–108; Figure 3.*

Burton, R.A., et al., "Starch Branching Enzymes Belonging to Distinct Enzyme Families are Differentially Expressed During Pea Embryo Development", Plant Journal, vol. 7, No. 1, Jan. 1995, pp. 3–15.*

Salehuzzaman, S.N.I.M, et al., "Cloning, Partial Sequencing and Expression of a cDNA Coding for Branching Enzyme in Cassava", Plant Molecular Biology, vol. 20, 1992, pp. 809–819.*

```
        10         20         30         40         50         60         70         80         90        100        110        120
  84 TTAGTTGCGTCAGTTCTCACACTTCTCACACTTCTCTAACTTCTCTAACTTCTCAGCGAACTGGACACTACACCATATCAGGAATACGTTTTCCTTGTCTGCTCCACTCGCAAATCTCAATCTACCGGCTTCCATGG
   5 TTAGTTGCGTCAGTTCTCACACTTCTCACACTTCTCTAACTTCTCTAACTTCTCAGCGAACTGGACACTACACCATATCAGGAATACGTTTTCCTTGTCTGCTCCACTCGCAAATCTCAATCTACCGGCTTCCATGG
   1 TTAGTTGCGTCAGTTCTCACACTTCTCACACTTCTCTAACTTCTCTAACTTCTCAGCGAACTGGACACTACACCATATCAGGAATACGTTTTCCTTGTCTGCTCCACTCGCAAATCTCAATCTACCGGCTTCCATGG 190        200        210        220        230        240        250        260        270        280        290        300
 264 GGTCTTCTCTGGAAAGTCATCTCATGAAGTCGACTCTCAAATGTAATGGTCACTGCCTCTAAAAGAGTCCTTCACTGCCTCTGATGGTCGGATTGAATGCTATTCTTCTTCAACAGATCAATTGAA
 185 GGTCTTCTCTGGAAAGTCATCTCATGAAGTCGACTCTCAAATGTAATGGTCACTGCCTCTAAAAGAGTCCTTCACTGCCTCTGATGGTCGGATTGAATGCTATTCTTCTTCAACAGATCAATTGAA
 181 GGTCTTCTCTAGAAAGTCATCTCATGAAGTCGACTCTCAAATGTAATGGTCACTGCCTCTAAAAGAGTCCTTCACTGCCTCTGATGGTCGGATTGAATGCTATTCTTCTTCAACAGATCAATTGAA 370        380        390        400        410        420        430        440        450        460        470        480
 444 GGATGATAAGATTGTTGAAGATGAAGTAAATAAAGAATCTGTTCCAATGCGGGAGACAGTTAGCATCGAAAAATTCAGAAAAATTGATCTAAACCAAGTCCATTCCTCCACCGGCAGAGGGCAAAG
 365 GGATGATAAGATTGTTGAAGATGAAGTAAATAAAGAATCTGTTCCAATGCGGGAGACAGTTAGCATCGAAAAATTCAGAAAAATTGATCTAAACCAAGTCCATTCCTCCACCGGCAGAGGGCAAAG
 361 GGATGATAAGATTGTTGAAGATGAAGTAAATAAAGAATCTGTTCCAATGCGGGAGACAGTTAGCATCGAAAAATTCAGAAAAATTGATCTAAACCAAGTCCATTCCTCCACCGGCAGAGGGCAAAG 550        560        570        580        590        600        610        620        630        640        650        660
 624 ACAGTACAAAAGACTCCGAGAAGAAGAAATTGACAAGTAGTCTCGGATGCATTTCTCGTGGCTATGAAGTTGGTTTCTCAGCGAGTGAAACAGGAATAACTTATAGAGAGTG
 545 ACAGTACAAAAGACTCCGAGAAGAAGAAATTGACAAGTAGTCTCGGATGCATTTCTCGTGGCTATGAAGTTGGTTTCTCAGCGAGTGAAACAGGAATAACTTATAGAGAGTG
 541 ACAGTACAAAAGACTCCGAGAAGAAGAAATTGACAAGTAGTCTCGGATGCATTTCTCGTGGCTATGAAGTTGGTTTCTCAGCGAGTGAAACAGGAATAACTTATAGAGAGTG 730        740        750        760        770        780        790        800        810        820        830        840
 804 AGATGTCATGACTCAGAATGAGTGTGGTGTCTGGGAGATCTTTTTGCCGAATAATGCAGATGGTTCACCGAATTCCCATGGTTCTCGAGTAAAGATACGCATGGATACTCCATCTGG
 725 AGATGTCATGACTCAGAATGAGTGTGGTGTCTGGGAGATCTTTTTGCCGAATAATGCAGATGGTTCACCGAATTCCCATGGTTCTCGAGTAAAGATACGCATGGATACTCCATCTGG
 721 AGATGTCATGACTCAGAATGAGTGTGGTGTCTGGGAGATCTTTTTGCCGAATAATGCAGATGGTTCACCGAATTCCCATGGTTCTCGAGTAAAGATATGCATGGATACTCCATCTGG 910        920        930        940        950        960        970        980        990       1000       1010       1020
 984 ATATAATGGCATATACTATGATCCTCCCGAGGAGGAGGAAGTATGTCTTCAAAAATCCTCAGCCAAAGACCAAAATCACTTCGGATTGTTCAAAATCACTTCGGAATGAGTCCACGTTGGAATGAGTAGTACGGA
 905 ATATAATGGCATATACTATGATCCTCCCGAGGAGGAGGAAGTATGTCTTCAAAAATCCTCAGCCAAAGACCAAAATCACTTCGGATTGTTCAAAATCACTTCGGAATGAGTCCACGTTGGAATGAGTAGTACGGA
 901 ATATAATGGCATATACTATGATCCTCCCGAGGAGGAGGAAGTATGTCTTCAAAAATCCTCAGCCAAAGACCAAAATCACTTCGGATTGTTCAAAATCACTTCGGAATGAGTCCACGTTGGAATGAGTAGTACGGA
```

| FIG. 3-1 | FIG. 3-2 |
|---|---|
| FIG. 3-3 | FIG. 3-4 |

FIG. 3

FIG. 3-1

```
                130         140         150         160         170         180
        TGATCGAAGGAGGACCTCCTCTTGCCTTTCCTTCAACTTCAAGAAGGCGGCGTTTCTAGGAG csbe2con.seq
        CGATCCCAGGAGGACCTCCTCTTGCCTTTCCTTCAACTTCAAGAAGAVGGCGTTTTCTAGGAG 20con.seq
        TGATCGAAGGAGGACCTCCTCTTGCCTTTCCTTCAACTTCAAGAAGGCGGCGTTTCTAGGAG 35con.seq 310         320         330         340         350         360
        AGCCCCTGGCACAGTTTCAGAAGAATCCCAGTGCTTACTGATGTTGAGAGTTCTCATTAT csbe2con.seq
        AGCCCCTGGCACAGTTTCAGAAGAATCCCAGTGCTTACTGATGTTGAGAGTTCTCATTAT 20con.seq
        AGCCCCTGGCACAGTTTCAGAAGAATCCCAGTGCTTACTGATGTTGAGAGTTCTCATTAT 35con.seq 490         500         510         520         530         540
        AATATATGACATAGATCCAAGCTTGACAGGCTTTCGTCAACACCTAGATTACCGGTATTC csbe2con.seq
        AATATATGACATAGATCCAAGCTTGACAGGCTTTCGTCAACACCTAGATTACCGGTATTC 20con.seq
        AATATATGACATAGATCCAAGCTTGACAGGCTTTCGTCAACACCTAGATTACCGGTATTC 35con.seq 670         680         690         700         710         720
        GGCACCAGGAGCTACGTGGGCTGCATTGATTGGAGATTTCAATAACTGGAATCCTAATGC csbe2con.seq
        GGCACCAGGAGCTACGTGGGCTGCATTGATTGGAGATTTCAATAACTGGAATCCTAATGC 20con.seq
        GGCACCAGGAGCTACGTGGGCTGCATTGATTGGAGATTTCAATAACTGGAATCCTAATGC 35con.seq 850         860         870         880         890         900
        CAACAAAGATTCTATTCCTGCTTGGATCAAGTTCTCAGTTCAAGCACCAGGTGAACTCCC csbe2con.seq
        CAACAAAGATTCTATTCCTGCTTGGATCAAGTTCTCAGTTCAAGCACCAGGTGAACTCCC 1805
        CAACAAAGATTCTATTCCTGCTTGGATCAAGTTCTCCAGTTCAAGCACCAGGTGAACTCCC 35con.seq 1030        1040        1050        1060        1070        1080
        GCCAGTAATTAACACATATGCCAACTTTAGAGATGATGTGCTTCCTCGCATCAAAAAGCT csbe2con.seq
        GCCAGTAATTAACACATATGCCAACTTTAGAGATGATGTGCTTCCTCGCATCAAAAAGCT 20con.seq
        GCCAGTAATTAACACATATGCCAACTTTAGAGATGATGTGCTTCCTCGCATCAAAAAGCT 35con.seq
```

FIG. 3-2

FIG. 3-3

```
                1200      1210      1220       1230      1240       1250      1260
ATGATTTAAAGTCCCTAGTAGATAAAGCTCACGAGTTAGGTCTTCTTCTTCTTCATGATATTGTTCATAG  csbe2con.seq
ATGATTTAAAGTCTCTAATAGATAAAGCTCACGAGTTAGGTCTTCTTCTTGTTCTTCATGATATTGTTCATAG  20con.seq
ATGATTTAAAGTCTCTAATAGATAAAGCTCACGAGTTAGGTCTTCTTCTTGTTCTTCTTATGATATTGTTCATAG  35con.seq 1380      1390      1400       1410      1420       1430      1440
TCAACTATGGGAGCTGGGAGGTTCTAAGGTTTCTCTTCAAATACAAGGTGGTGGTTGGATGAGTACAA  csbe2con.seq
TCAACTATGGGAGCTGGGAGGTTCTAAGGTTCTCTTTCAAATGCAAGGTGGTGGTTGGATGAGTACAA  20con.seq
TCAACCATGGGAGCTGGGAGGTTCTAAGGTTCTCTTTCAAATGCAAGGTGGTGGTTGGATGAGTACAA  35con.seq 1560      1570      1580       1590      1600       1610      1620
TAGATGCTGTGGTTTATGTGATGCTGTTGAATGATATGATTCATGGTCTCTTCCCAGAGGCTGTCACCAT  csbe2con.seq
TAGATGCTGTGTGGTTTATTTGATGCTGTTGAATGATATGATTCATGGTCTCTTCCCAGAGGCTGTCACCAT  20con.seq
TAGATGCTGTGGTTTATTTGATGCTGTTGAATGATATGATTCATGGTCTCTTCCCAGAGGCTGTCACCAT  35con.seq 1740      1750      1760       1770      1780       1790      1800
TTCAGAAGAGAGATGAAGATTGGAAAAATGGTGACATTGTACATATGCTGACCAACAGCCGGTGGTTGGA  csbe2con.seq
TTCAGAAGAGAGATGAAGATTGAAAAATGGTGACATTGTACATATGCTGACCAACAGCCGGTGGTTGGA  20con.seq
TTCAGAAGAGAGATGAAGATTGAAAAATGGTGACATTGTACATATCCTGACCAACAGCCGGTGGTTGGA  35con.seq 1920      1930      1940       1950      1960       1970      1980
CATCTACTCCTCTTATAGATCGTGGAATAGCATTGCACAAAATGATCAGGCTTATTACCATGGCTTAGG  csbe2con.seq
CATCTACTCCTCTCATAGATCGTGGAGTAGCATTGCACAAAATGATCAGGCTTATTACCATGGATTAGG  20con.seq  1805
CATCTACCCCTCTTATAGATCGTGGAGTAGCATTGCACAAAATGATCAGGCTTATTACCATGGATTAGG  35con.seq 2100      2110      2120       2130      2140       2150      2160
ACCTACAGTTATGATAATGCCGGCTGCGCGTAGTTTGATCTAGCATGCAGTATCTAAGATATCATGAAT  csbe2con.seq
ATTACAGTTATGATAATGCCGGCGTAGTTTGATCTAGCAATTCAAAGCATCTGAGATATCATGGAAT  20con.seq
ATTACAGTTATGATAATGCCGGCGTAGTTTGATCTAGCAATTCAAAGCATCTGAGATATCATGGAAT  35con.seq csbe2con.seq
                                            20con.seq
                                            35con.seq
```

```
125+94. seq    1320      1330      1340      1350      1360      1370      1380
               TGGAGGCTTCAACAGGCTTAGTCAGTCATGATGCCGAGCACTTCACCTTTGACGGGTGGTATGATAACCGGCCT
116. seq       TGGAGGCTT   CAGGCTTAGTCAGTCATGATGC GAGCACTTCA CTTTGA GGGTGGTA GATAACCGGCCT
               2400      2410      2420      2430      2440      2450      2460
               TGGAGGCTTTGGCAGGCTTAGTCAGTCATGATGCAGAGCACTTCAGCTTTGAAGGGTGGTACGATAACCGGCCT
               1390      1400      1410      1420      1430      1440      1450
125+94. seq    CGGTCCTTCATGGTATATGCACCATCTAGGACAGCAGTGGTCCATGCTTTAGTAGAAGATGAAG
116. seq       CGGTCCTTCATGGTATATGCACCATCTAGGACAGCAGTGGTCCATGCTTTAGTAGAAGATGAAG
               2470      2480      2490      2500      2510      2520      2530
               CGGTCCTTCATGGTATATGCACCATCTAGGACAGCAGTGGTCCATGCTTTAGTAGAAGATGAAG
```

FIG. 5-3

```
125-94.pro  SFGYHVTNFFAPSSRFGTPDDLKSLIDKAHELGLLVLMDIVHSHASNNTLDGLNMPDGTDSHYFHSGSRG
116.pro     SFGYHVTNF:A:SSRFGTPDDLKSLIDKAHELGLLVLMDIVHSHASN.TLDGLNMFDGTD:HYFHSGSRG
            SFGYHVTNFYAASSRFGTPDDLKSLIDKAHELGLLIVLMDIVHSHASNTTLDGLNMFDGTDPHYFHSGSRG 125-94.pro  HHWLWDSRLFNYGSWEVLRFLLSNARWWLEEYRFDGFRFDGVTSMMYTPHGLQVAFTGNYNEYFGYATDV
116.pro     HHW:WDSRLFNYGSWEVLRFLLSNARWWL.EY:FDGFRFDGVTSMMYT.HGLQV.FTGNYNEYFGYATDV
            HHWMWDSRLFNYGSWEVLRFLLSNARWWLDEYKFDGFRFDGVTSMMYTHHGLQVDFTGNYNEYFGYATDV 125-94.pro  DAVIYLMLVNDMIHGLFPEAVTIGEDVSGKPTFCIPVEDGGVGFDYRLHMAIADKWIEILKKRDEDWKMG
116.pro     DAV:YLML:NDMIHGLFPEAVTIGEDVSG..PT.CIPVEDGGVGFDYRLHMA.ADKW:EI::KRDEDWKMG
            DAVVYLMLLNDMIHGLFPEAVTIGEDVSGMPTVCIPVEDGGMPTVCIPVEDGGVGFDYRLHMAVADKWVEIIOKRDEDWKMG 125-94.pro  DIVHTLTNRRWLEKCVAYAESHDQALVGDKTIAFWLMDKDMYDFMARDRPSTPLIDRGIALHKMIRLITM
116.pro     DIVH.LTNRRWLEKCV:YAESHDQALVGDKTIAFWLMDKDMYDFMA.DRPSTPLIDRG:ALHKMIRLITM
            DIVRMLTNRRWLEKCVSYAESHDQALVGDKTIAFWLMDKDMYDFMALDRPSTPLIDRGVALHKMIRLITM 125-94.pro  GLGGEGYLNFMGNEFGHPEWIDFPRGDRHLPNGKVIPGNNHSYDKCRRRFDLGDADYLRYHGMOEFDOAM
116.pro     GLGGEGYLNFMGNEFGHPEWIDFPRGD.HLP:GK:PGNN.SYDKCRRRFDLGD:::.RYHGMOEFDOA:
            GLGGEGYLNFMGNEFGHPEWIDFPRGDLHLPSGKFVPGNNYSYDKCRRRFDLGDNSKHRYHGMOEFDOAI 125-94.pro  OHLEEAYGFMTSEHQYISRKDEGRIIVFERGNLVFVFNFHWTNSYSDYRVGCFKSGKYKIVLDSDDGLF
116.pro     OHLEEAYGFMTSEHQYISRKDEGRIIVFERGNLVFVFNFHWT:SYSDYRVGC.KSGKYKIVLDSDD.LF
            OHLEEAYGEMTSEHQYISRKDEGRIIVFERGNLVFVFNFHWTSSYSDYRVGCLKSGKYKIVLDSDDPLF 125-94.pro  GGFNRLSHDAEHFTPDGWYDNRPRSFMYYAPSRTAVVHALVEDEENEAENEVES
116.pro     GGF.RLSHDAEHF:F.GWYDNRPRSFMY:.P.RTAVV.ALVEDE.::.:.VES
            GGFGRLSHDAEHFSPEGWYDNRPRSFMYTPCRTAVVYALVEDEVENEVEPVAG
```

FIG. 6

```
zmcon12.pro
RICE.2
psstb1.pro
SJ107.pro
atsbe2-1.pro
atsbe2-22.pro
potsbe2.pro 0    5    10    15    20    25   27.2
```

```
                                                                              Bcl I         Nco I
ATGGACAAGGATATGTATGACTTCATGGCTCTTGACAGACCATCTACTCCTCTCATAGATCGTGTGAGTAGCATTGCACAAATGATCAGGCTTATTACCA
TACCTGTTCCTATACATACTGAAGTACCGAGAACTGTCTGGTAGATGAGGAGATATTCAGCACACTCTAGCACTCGTAACGTGTTTTACTAGTCCGAATAATGGT  100
M  D  K  D  M  Y  D  F  M  A  L  D  R  P  S  T  P  L  I  D  R  G  V  A  L  H  K  M  I  R  L  I  T
TGGGATTAGGCGGAGAAGGATATTTGAATTTTATGGGAAATGAATTTGGACACCCCGAGTGATTATTTCCAAGAGTGATCTACATCTTCCAGTGG
ACCCTAATCCGCCTCTTCCTATATAAACTTAAAATACCCTTTACTTAACCTGTGGGGCTCACCTACTAAAAAGGTTCTCCACTAGATGTAGAAGGGTCACC  200
M  G  L  G  G  E  G  Y  L  N  F  M  G  N  E  F  G  H  P  E  W  I  D  F  P  P  R  G  D  L  H  L  P  S  G
                                                                                           EcoR V         Bcl I
TAAATTTGTTCCTGGAACAATTACAGTTATGATAAGTCCGGCGTAGGTTTGATCTAGCAATTCAAAGCGTCTGAGATATCATGAATGCAAGAGTTT
ATTTAAACAAGGACCCTTGTTAATGTCAATACTATTCAGCGCCATCCAAACTAGATCCGTTAAGTTCGCAGACTCTATAGTACCTTACGTTCTCAAA  300
K  F  V  P  G  N  N  Y  S  Y  D  K  C  R  R  F  D  L  G  N  S  K  R  L  R  Y  H  G  M  O  E  F
GATCAAGCAATTCAGCATCTTGAAGAACCTATGGTTTCATGACTTCTGAGCACCATACATTACGGAAGGATCGAAAGGATCGATCATTGTCTTCG
CTAGTTCGTTAAGTCGTAGAACTTCTTCGGATACCAAGACTACTGAAGACTCGTGGTTATAGTGCCTTCCTAGCCTAGTAACAGAAGC  400
D  Q  A  I  O  H  L  E  E  A  Y  G  F  M  T  S  E  H  O  Y  I  S  R  K  D  E  R  D  R  I  I  V  F
AGAGGGGAAACCTCGTTTTGTATTCAATTTTCATTGGACTAGCAGTTGGCTGCTGCTAAAGCCAGGAAGTACAAGATAGTCTT
TCTCCCCTTTGGAGCAAAACATAAGTTAAAACATATCGTCGACCGAGTCTTCGGTCCTTCCATGTTCTATCAGAA  500
E  R  G  N  L  V  F  V  F  N  F  H  W  T  S  S  Y  S  D  Y  R  V  G  C  L  K  P  G  K  Y  K  I  V  L
GGATTCAGATGATCATCCTTTGTTGGAGGCTTTGCAGGCTTAGTCATGATGCAGAGCACTTGAAGGTGGTACGATAACCGGCTCGATCCTTC
CCTAAGTCTACTAGGAAAACAAACTCCGAATCAGTCTCCGAATCAGTCACGTCCGTCCGAAGTCGAAACTTCCACCATGCTATTGGCGGACTAGGAAG  600
D  S  D  D  P  L  F  G  G  F  G  R  L  S  H  D  A  E  H  F  S  F  E  G  W  Y  D  N  R  P  R  S  F
ATGGTGTACACCATGTAGAACAGCAGTTGTCTATGCGTTCAGTTAGTGGAGGATGAAGTGAAGTGAACCTGTCGCCGTTAAGATATATCTTAGC
TACCACATGTGGTACATCTTGTCGTCAGTCGACAGATACGAAATCACCTTCACCTTACTTCACCTACTTCACTTGAATACTGAAGAATCG  700
M  V  Y  T  P  C  R  T  A  V  V  Y  A  L  V  E  D  E  V  E  N  E  V  E  P  V  A  G
AACAGGTTCTGAAGCAGGAAGTCCATTATTGATCTTCCTATGTGCATCTGCCTTGCGTCGTTGAACGAAATATATTGAGCCTATAAATTGATGCACGGTTCCTTGCAG
TTGTCCAAGACTTCGTCGTTCCTTCAGGTAATAACTACGAAGGATACACGTAGACGCAACTTGCTTTATATAACTCGGATATATAAACTACAGTGCCAGGAACGTC  800
ATTTCCATCGTCTGGTTCGTGGTATTTGTTGTGTCATGATAATAAACATAATCAAGACGGTTACATGCTAGCTTCCATCATCATAGGGAG
TAAAGTAGGACCAAGACCATAAAACAACAGTACTATTTGTATTAGTT-CTGGTTATCCTTTGCGTCCCAATGTACTACGAGGTACTACTATCCCTC  900
                                                                                                            Bcl I
CTCAGACCTTCCTAAACCATAAATCTTCAAGCTTCCTTAGGTAGTATGTTATGTGGTACTTTGCAATCTTAAATATCATGATCGTGTGGATGCTA
GAGTCTGGAGGATTTGGTATTTGAAGTTCGACGACGACGAAGCCATCATACAATACACCATGAAACGTTAGAATTTAATAGTACTAGCGACACCTACGAT  1000
ACTATGACAATTTTGTATATATGCCAACGAGGATTTTAAGTTTTAAAAAAAAAACAAAAAATCCATG
TGAATACTGTTAAAACATATATACGGTTGCCTCCTAAAATTTTTTTTTTTTGTTTTTTGTTAGGTAC   1069
```

FIG. 10-1

FIG. 10-2

```
                    Kpn I
                    Xma I
                    |  Sma I
           Sac I    |  | BamH I
           ....     ....
AGTGAATTCGAGCTCGGTACCCGGGGATCCGATTCGCATTTCTCGCTATTGCTTTCCGTTGTATTTCCATATATAAAATATCAAATCTAATCACTTGCGCCATTTCTATCTCTCCAAAC  120
TCACTTAAGCTCGAGCCATGGGCCCCTAGGCTAAGCGTAAAGAGCGATAACGAAAGGCAAATAAGGTATATATATTTTATAGTTTAGATTAGTGAACCGGTAAAGATAGAGAGAGGTTTG
                                                                                                      NcoI
                                                                                                      ...
          M  V  Y  Y  T  V  S  G  I  R  F  P  C  A  P  S  L  Y  K  S  Q  L  T  S  F  H  G  G  R  R  T  S  S  G  L  S  F
TCTCACCGAAATGGTATACTACACTGTATCAGGCATACGTTTTCCTTGTGCACCTTCAGCTCTACAAATCTCAGCTTCACCATGGCGGTCAAGGACCTTTCTGGCCTTTCCTT
AGAGTGGCTTTACCATATGATGTGACATAGTCCGTATGCAAAGGAACACGTGGAAGTCGAGATGTTTAGAGTCGAAGTGGTCGAAGTCGAAGTCCTGGAAGACCGGAAAGGAA     240
                                                                                                                 Bcl I
                                                                                                                 ...
L  L  K  K  E  L  F  P  R  K  I  F  A  G  K  S  S  Y  E  S  D  S  N  L  T  V  S  A  S  E  K  V  L  V  P  D  D  O  I
CCTCTTGAAGAAGGAGCTGTTTCCTCGGAAGATCTTTGCTGGAAAGTCCTCATATGAATCTGACTCCTCAAATTTAACTGTCTCTGCATCTGAGAAGGTCCTTGTTCCTGATGATCAGAT
GGAGAACTTCTTCCTCGACAAAGGAGCCTTCTAGAAACGACCTTTCAGGAGTACTTAGACTGAGGAGTTTAAATTGACAGAGACTAGACTCTTCCAGGAACAAGGACTACTAGTCTA    360
                                                                                             BstX I
                                                                                             ...
T  Y  O  L  E  T  T  G  T  V  L  E  E  S  O  V  L  G  D  A  E  S  L  V  M  E  D  D  K  N  V  E  E  D
TGATGGCTCTTCTTCTTCAACATATCAATTAGAAACCACTGGCACAGTTTTGGAGGAATCCAGAGTTCTTGGTGATGCAGAGAGTCTTGTGATGGAAGATGATAAGAATGTTGAGGAGGA
ACTACCGAGAAGAAGAAGTTGTATAGTTAATCTTTGGTGACCGTGTCAAAACCTCCTTAGGTCTCAAGAACACTACGTCTCTCAGACAACTCCTTCTACTATTCTTACAACTCCTCCT     480
                                                                                                         Hind III
                                                                                                         ...
D  G  S  S  S  T  Y  O  L  E  T  T  G  T  V  L  E  E  S  O  V  L  G  D  A  E  S  L  V  M  E  D  D  K  N  V  E  E  D
                E  V  K  K  E  S  V  P  L  H  E  T  I  S  I  G  K  S  E  S  K  P  R  S  I  P  P  P  G  S  G  O  R  I  Y  D  I  D  P  S
TGAAGTAAAAAAGAGTCGGTTCCATTGCATGAGACAATTAGCATTGGAAAAAGTGAATCTAAACAAGGTCCATTCCTCCACCTGGCAGTGGGCAGAGAATATGACATAGATCCAAG
ACTTCATTTTTTTCTCAGCCAAGGTAACGTACTCTGTTAATCGTAACCTTTTCACTTAGAGTTGTTCCAGGTAAGGAGGTGGACCCGTCTCTTATATACTGTATCTAGGTTC    600
```

| FIG. 13-1 |
| FIG. 13-2 |
| FIG. 13-3 |
| FIG. 13-4 |

FIG. 13

FIG. 13-1

```
                                                                                                    NsiI
CTTTGGCAGGTTTCCGTCAGCATCTTGACTACCGATATTCACAGTACAAAAGGCTGCGTGAGGAAATTGACAAGTATCAAGGTGTTTGGATGCATTCTCTGTGATTTGAAAAGTTTGG 720
GAACCGTCCAAAGGCAGTCGTAGAACTGATGCTATAAGTGTCATGTTTTCCGACGCACTCCTTAACTGTTCCACCAAACTACGTAAGAGACACTAAACTTTTCAAACC
 L  A  G  F  R  O  H  L  D  Y  R  Y  S  O  Y  K  R  L  R  E  E  I  D  K  Y  E  G  G  L  D  A  F  S  R  G  F  E  K  F  G

TTTCTTACGCAGTGAAACAGGAATAACTTATAGGAGAATTCCCTTATTGAATATCCCACGACTGAATAACCTTCTAAAGTTGTTAACCTTAGGATTACGTCTACGAGTACTGAGCCTTACT 840
AAAGAATGCGTCACTTTGTCCTTATTGAATAATCCCTTAAGGGATGAACTTATAGGGTGCTGACTTATTGGAAGTTGTTCAACAATTGAATGGAAGATTCAGATGTCATGACTCGGAATGA
 F  L  R  S  E  T  G  I  T  Y  R  E  W  A  P  G  A  T  W  A  A  L  I  G  D  F  N  N  W  N  P  N  A  D  V  M  T  R  N  E

GTTTGGTGTCTGGGAGATTTTTTGCCAAATAACGCAGATGTTCACCACCAATTCCTCATGTTCTCGAGTAAAGATACGCATGATACTCCATCTGCATCCTATAAAGATTCAATTCCTGC 960
CAAACCACAGACCCTCTAAAAAAACGGTTTATTGCGTCTACAAGTGGTTAAGGAGTACAAGAGCCATTCTATGGTACTATGAGTAGACCGTAGTTTCTAAGTTAAGGACG
 F  G  V  W  E  I  F  L  P  N  N  A  D  G  S  P  P  I  P  H  G  S  R  V  K  I  R  M  D  T  P  S  G  I  K  D  S  I  P  A

TTGGATCAAGTTCTCAGTCCTGGGACCACCTCAGCGAAATCCATATACAATGATCCATATAATTAACACATCCTCAGCCAAAGAGACCAAAATCACT 1080
                                                                                                                 HindIII
AACCTAGTTCAAGAGTCAGGTCCGGTGGACCACTTAGGGATGTATGATACGGATTATAATTGTGTAGGTCGCGTTTCCTCTCTCATACAAGTTGTTAGGAGTCGGTTCTCTGGTTTTAGTGA
 W  I  K  F  S  V  O  A  P  G  E  I  P  Y  N  A  I  Y  Y  D  P  P  K  E  E  K  Y  V  F  K  H  P  O  P  K  R  P  K  S  L TAGGATTTATGAATCTCATGTTGGGATGAGTAGTATGGAGCCAATAATTAACACATAACACATTAGAGATGATATGCTTCCTCGCATCAAAAGCTTGGCTACAATGTCTGTTCAGAT 1200
                                                                    NdeI
ATCCTAAATACTTAGAGTACAACATCACATCATTCAGTACGAATGCAGGTTGAACATTTCTACTATACGAAGGAGCTAGTTTTCGAACCGATGTTACGACAAGTCTA
 R  I  Y  E  S  H  V  G  M  S  S  M  E  P  I  I  N  T  Y  A  N  F  R  D  D  M  L  P  R  I  K  K  L  G  Y  N  A  V  O  I CATGGCTATTCAAGAGCAGCATTCCTATTATGCTAGTTTTGGGTACCATGTCACAAACCTTTTGCACCTAGCAGCCGATTGGAACTCCTGATGATTGAAGTCTTTAATAGATAAAGCTCA 1320
                     KpnI
GTACCGATAAGTTCTCGTAAGGATAATACGATCAAAAACCCATGGTACAGTGTTTGAAAAAACGTGGATCGCTAACCTTGAGGACTACTAAACTTCAGAAATTATCTATTTCGAGT
 M  A  I  O  E  H  S  Y  Y  A  S  F  G  Y  H  V  T  N  F  F  A  P  S  S  R  F  G  T  P  D  D  L  K  S  L  I  D  K  A  H TGAGTTAGGGCTGCTTGTTCTCATGGACATTGACGGTCTCAAATAATACGTTCAGTTTATTATTGCGACTTGTACAAACTACCATGCCTATCAGTGATCAGAAGGGTGAGGCCTAGTGCCCCC 1440
ACTCAANYCCCGACGCAACAAGAGTACCTATAAACAAGTATGCTACGCAGTTATAATAACGACTGAACATGTTTGATGGTACGATAGTCACTACCGGATCACGGGG
 E  L  G  L  L  V  L  M  D  I  V  H  S  H  A  S  N  N  T  L  D  G  L  N  M  F  D  G  T  D  S  H  Y  F  H  S  G  S  R  G

NUCLEIC ACIDS FROM CASSAVA ENCODING STARCH BRANCHING ENZYME II (SBEII) AND THEIR USE

FIELD OF THE INVENTION

This invention relates to novel nucleic acid sequences, vectors and host cells comprising the nucleic acid sequence(s), to polypeptides encoded thereby, and to a method of altering a host cell by introducing the nucleic acid sequence(s) of the invention.

BACKGROUND OF THE INVENTION

Starch consists of two main polysaccharides, amylose and amylopectin. Amylose is a linear polymer containing α-1,4 linked glucose units, while amylopectin is a highly branched polymer consisting of a α-1,4 linked glucan backbone with α-1,6 linked glucan branches. In most plant storage reserves amylopectin consitutes about 75% of the starch content. Amylopectin is synthesized by the concerted action of soluble starch synthase and starch branching enzyme [α-1,4 glucan: α-1,4 glucan 6-glycosyltransferase. EC 2.4.1.18]. Starch branching enzyme (SBE) hydrolyses α-1,4 linkages and rejoins the cleaved glucan, via an α-1,6 linkage, to an acceptor chain to produce a branched structure. The physical properties of starch are strongly affected by the relative abundance of amylose and amylopectin, and SBE is therefore a crucial enzyme in determining both the quality and quality of starches produced in plant systems.

Starches are commercially available from several plant sources including, maize, potato and cassava. Each of these starches has unique physical characteristics and properties and a variety of possible industrial uses. In maize there are a number of naturally occurring mutants which have altered starch composition such as high amylopectin types ("waxy" starches) or high amylose starches but in potato and cassava no such mutants exist on a commercial basis as yet.

Genetic modification offers the possibility of obtaining new starches which may have novel and potentially useful characteristics. Most of the work to date has involved potato plants because they are amenable to genetic manipulation i.e. they can be transformed using Agrobacterium and regenerated easily from tissue culture. In addition many of the genes involved in starch biosynthesis have been cloned from potato and thus are available as targets for genetic manipulation, for example, by antisense inhibition of expression or sense suppression.

Cassava (*Manihot esculenta* L. Crantz) is an important crop in the tropics, where its starch-filled roots are used both as a food source and increasingly as a source of starch. Cassava is a high yielding perennial crop that can grow on poor soils and is also tolerant of drought. Cassava starch being a root-derived starch has properties similar but not identical to potato starch and is composed of 20–25% amylose and 75–80% amylopectin (Rickard et al., 1991. Trop. Sci. 31, 189–207). Some of the genes involved in starch biosynthesis have been cloned from cassava, including starch branching enzyme I (SBE I) (Salehuzzaman et al., 1994 Plant Science 98, 53–62), and granule bound starch synthase I (GBSS I) (Salehuzzaman et al., 1993 Plant Molecular Biology 23, 947–962) and some work has been done on their expression patterns although only in in vitro grown plants (Salehuzzaman et al., 1994 Plant Science 98, 53–62).

In most plants studied to date e.g. maize (Boyer & Preiss. 1978 Biochem. Biophys. Res. Comm. 80, 169–175), rice (Smyth. 1988 Plant Sci. 57, 1–8) and pea (Smith, Planta 175, 270–279), two forms of SBE have been identified, each encoded by a separate gene. A recent review by Burton et al., (1995 The Plant Journal 7, 3–15) has demonstrated that the two forms of SBE constitute distinct classes of the enzyme such that, in general, enzymes of the same class from different plants may exhibit greater similarity than enzymes of different classes from the same plant. In their review, Burton et al. termed the two respective enzyme families class "A" and class "B", and the reader is referred thereto (and to the references cited therein) for a detailed discussion of the distinctions between the two classes. One general distinction of note would appear to be the presence, in class A SBE molecules, of a flexible N-terminal domain, which is not found in class B molecules. The distinctions noted by Burton et al. are relied on herein to define class A and class B SBE molecules, which terms are to be interpreted accordingly.

Many organisations have interests in obtaining modified Cassava starches by means of genetic modification. This is impossible to achieve however, unless the plant is amenable to transformation and regeneration, and the starch biosynthesis genes which are to be targeted for modification must be cloned. The production of transgenic cassava plants has only recently been demonstrated (Taylor et al., 1996 Nature Biotechnology 14, 726–730; Schöpke et al., 1996 Nature Biotechnology 14, 731–735; and Li et al., 1996 Nature Biotechnology 14, 736–740). The present invention concerns the identification, cloning and sequencing of a starch biosynthetic gene from Cassava, suitable as a target for genetic manipulation.

SUMMARY OF THE INVENTION

In a first aspect the invention provides a nucleic acid sequence encoding a polypeptide having starch branching enzyme (SBE) activity, the polypeptide comprising an effective portion of the amino acid sequences shown in FIG. 4 or FIG. 13. The nucleic acid is conveniently in substantial isolation, especially in isolation from other naturally associated nucleic acid sequences.

An "effective portion" of the amino acid sequences may be defined as a portion which retains sufficient SBE activity when expressed in *E. coli* KV832 to complement the branching enzyme mutation therein. The amino acid sequences shown in FIGS. 4 and 13 include the N terminal transit peptide, which comprises about the first 50 amino acid residues. As those skilled in the art will be well aware, such a transit peptide is not essential for SBE activity. Thus the mature polypeptide, lacking a transit peptide, may be considered as one example of an effective portion of the amino acid sequence shown in FIG. 4 or FIG. 13.

Other effective portions may be obtained by effecting minor deletions in the amino acid sequence, whilst substantially preserving SBE activity. Comparison with known class A SBE sequences, with the benefit of the disclosure herein, will enable those skilled in the art to identify regions of the polypeptide which are less well conserved and so amenable to minor deletion, or amino acid substitution (particularly, conservative amino acid substitution) whilst substantially preserving SBE activity. Such less well-conserved regions are generally found in the N terminal amino acid residues (up to the triple proline "elbow" at residues 138–140 in FIG. 4 and up to the proline elbow at residues 143–145 in FIG. 13) and in the last 50 residues or so of the C terminal, and in particular in the acidic tail of the C terminal.

Conveniently the nucleic acid sequence is obtainable from cassava, preferably obtained therefrom, and typically encodes a polypeptide obtainable from cassava. In a particular embodiment, the encoded polypeptide may have the amino acid sequence NSKH (SEQ ID NO: 32) at about position 697 (in relation to FIG. 4 (SEQ. ID. NO. 29)), which sequence appears peculiar to an isoform of the SBE class A enzyme of cassava, other class A SBE enzymes having the conserved sequence DA D/E Y (SEQ ID NO: 33) (Burton et al., 1995 cited above).

In a particular aspect of the invention there is provided a nucleic acid comprising a portion of nucleotides 21 to 2531 of the nucleic acid sequence shown in FIG. 4, or a functionally equivalent nucleic acid sequence. Such functionally equivalent nucleic acid sequences include, but are not limited to, those sequences which encode substantially the same amino acid sequence but which differ in nucleotide sequence from that shown in FIG. 4 by virtue of the degeneracy of the genetic code. For example, a nucleic acid sequence may be altered (e.g. "codon optimised") for expression in a host other than cassava, such that the nucleotide sequence differs substantially whilst the amino acid sequence of the encoded polypeptide is unchanged. Other functionally equivalent nucleic acid sequences are those which will hybridise under stringent hybridisation conditions (e.g. as described by Sambrook et al., Molecular Cloning. A Laboratory Manual, CSH, i.e. washing with 0.1×SSC, 0.5% SDS at 68° C.) with the sequence shown in FIG. 4. FIG. 10 shows a functionally equivalent sequence designated "125+94", which includes a region corresponding to the 3' coding portion of the sequence in FIG. 4. FIG. 13 shows a functionally equivalent sequence which comprises a second complete SBE coding sequence (the SBE-derived sequence is from nucleotides 35 to 2760, of which the coding sequence is nucleotides 131–2677, the rest of the sequence in the figure is vector-derived).

Functionally equivalent DNA sequences will preferably comprise at least 200–300 bp, more preferably 300–600 bp, and will exhibit at least 88% identity (more preferably at least 90%, and most preferably at least 95% identity) with the corresponding region of the DNA sequence shown in FIGS. 4 or 10. Those skilled in the art will readily be able to conduct a sequence alignment between the putative functionally equivalent sequence and those detailed in FIGS. 4 or 10—the identity of the two sequences is to be compared in those regions which are aligned by standard computer software, which aligns corresponding regions of the sequences.

Figures 2, 8:
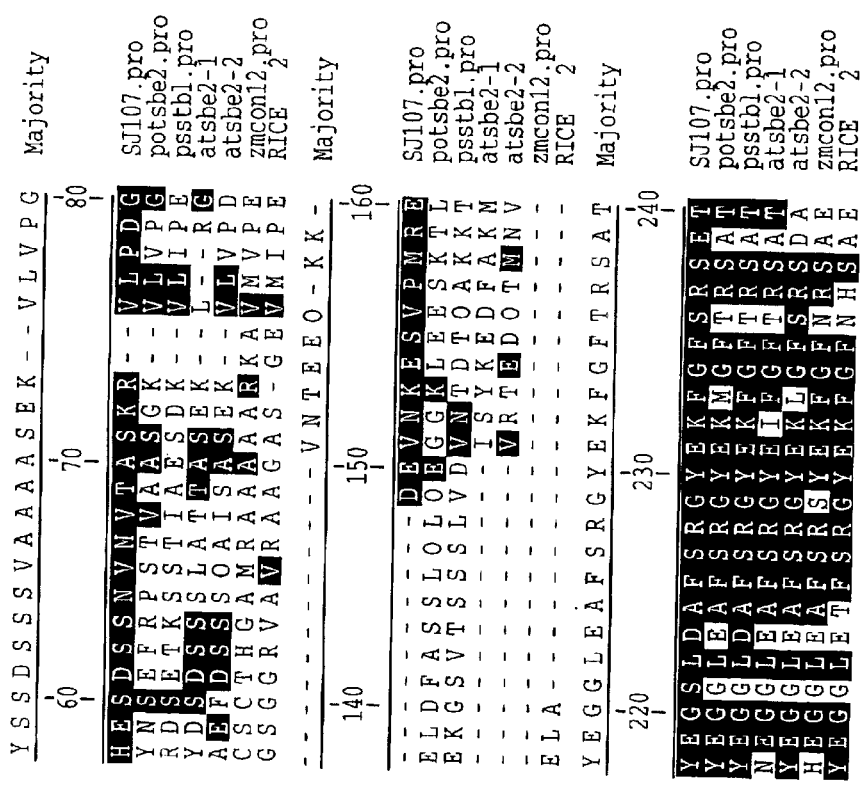
Figure 8:
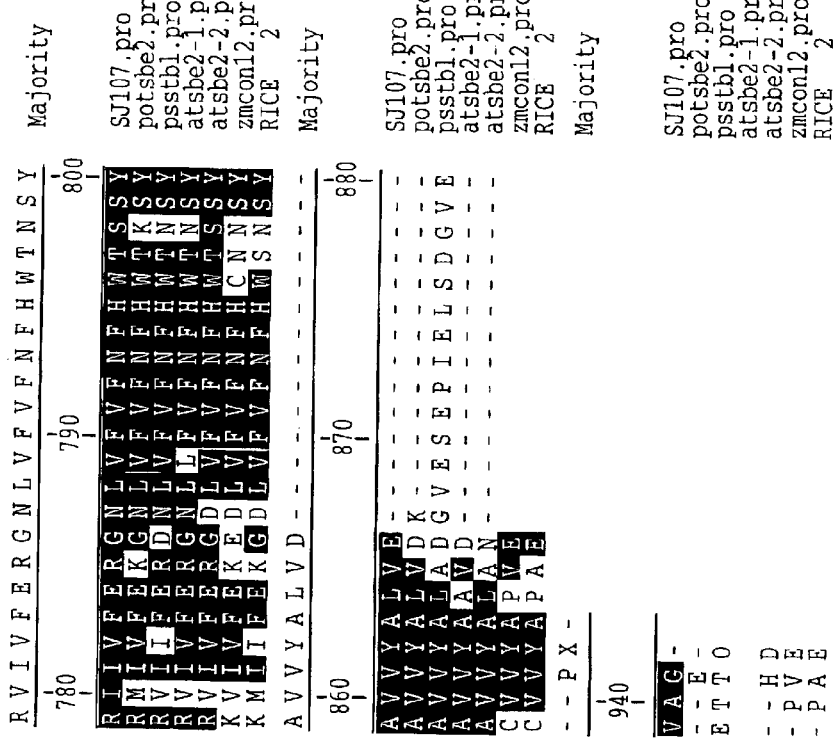

In particular embodiments the nucleic acid sequence may alternatively comprise a 5' and/or a 3' untranslated region ("UTR"), examples of which are shown in FIGS. 2 and 4. FIG. 9 includes a 3' UTR, as nucleotides 688–1044 and FIG. 10 includes 3' UTR as nucleotides 1507–1900 (which nucleotides correspond to the first base after the "stop" codon to the base immediately preceding the poly (A) tail). Any one of the sequences defined above, or a functional equivalent thereof (as defined by hybridisation properties, as set out in the preceding paragraph), could be useful in sense or anti-sense inhibition of corresponding genes, as will be apparent to those skilled in the art. It will also be apparent to those skilled in the art that such regions may be modified so as to optimise expression in a particular type of host cell and that the 5' and/or 3' UTRs could be used in isolation, or in combination with a coding portion of the sequence of the invention. Similarly, a coding portion could be used without a 5' or a 3' UTR if desired.

In a further aspect, the invention provides a replicable nucleic acid construct comprising any one of the nucleic acid sequences defined above. The construct will typically comprise a selectable marker and may allow for expression of the nucleic acid sequence of the invention. Conveniently the vector will comprise a promoter (especially a promoter sequence operable in a plant and/or a promoter operable in a bacterial cell) and one or more regulatory signals known to those skilled in the art.

In another aspect the invention provides a polypeptide having SBE activity, the polypeptide comprising an effective portion of the amino acid sequence shown in FIG. 4 (SEQ. ID. NO. 29) or FIG. 13 (SEQ. ID. NO. 31). The polypeptide is conveniently one obtainable from cassava, although it may be derived using recombinant DNA techniques. The polypeptide is preferably in substantial isolation from other polypeptides of plant origin, and more preferably in substantial isolation from any other polypeptides. The polypeptide may have amino acid residues NSKH (SEQ ID NO: 32) at about position 697 (in the sequence shown in FIG. 4 (SEQ. ID. NO. 29)), instead of the sequence DA D/E Y (SEQ ID NO: 33) found in other SBE class A polypeptides. The polypeptide may be used in a method of modifying starch in vitro, the method comprising treating starch under suitable conditions (of temperature, pH etc.) with an effective amount of the polypeptide.

Those skilled in the art will appreciate that the disclosure of the present specification can be utilised in a number of ways. In particular, the characteristics of a host cell may be altered by recombinant DNA techniques. Thus, in a further aspect, there is provided a method by which a host cell may be altered by introduction of a nucleic acid sequence comprising at least 200 bp and exhibiting at least 88% sequence identity (more preferably at least 90%, and most preferably at least 95% identity) with the corresponding region of the DNA sequence shown in FIGS. 4, 9, 10 or 13, operably linked in the sense or (preferably) in the anti-sense orientation to a suitable promoter active in the host cell, and causing transcription of the introduced nucleic acid sequence, said transcript and/or the translation product thereof being sufficient to interfere with the expression of a homologous gene naturally present in said host cell, which homologous gene encodes a polypeptide having SBE activity. The altered host cell is typically a plant cell, such as a cell of a cassava, banana, potato, sweet potato, tomato, pea, wheat, barley, oat, maize, or rice plant.

Desirably the method further comprises the introduction of one or more nucleic acid sequences which are effective in interfering with the expression of other homologous gene or genes naturally present in the host cell. Such other genes whose expression is inhibited may be involved in starch biosynthesis, (e.g. an SBE I gene), or may be unrelated to SBE II.

Those skilled in the art will be aware that both anti-sense inhibition, and "sense suppression" of expression of genes, especially plant genes, has been demonstrated (e.g. Matzke & Matzke 1995 Plant Physiol. 107, 679–685).

It is believed that antisense methods are mainly operable by the production of antisense mRNA which hybridises to the sense mRNA, preventing its translation into functional polypeptide, possibly by causing the hybrid RNA to be degraded (e.g. Sheehy et al., 1988 PNAS 85, 8805–8809; Van der Krol et al. Mol. Gen. Genet. 220, 204–212). Sense suppression also requires homology between the introduced sequence and the target gene, but the exact mechanism is unclear. It is apparent however that, in relation to both antisense and sense suppression, neither a full length nucleotide sequence, nor a "native" sequence is essential. Preferably the nucleic acid sequence used in the method will comprise at least 200–300 bp, more preferably at least 300–600 bp, of the full length sequence, but by simple trial and error other fragments (smaller or larger) may be found which are functional in altering the characteristics of the plant. It is also known that untranslated portions of sequence can suffice to inhibit expression of the homologous gene—coding portions may be present within the introduced sequence, but they do not appear to be essential under all circumstances.

The inventors have discovered that there are at least two class A SBE genes in cassava. A fragment of a second gene has been isolated, which fragment directs the expression of the C terminal 481 amino acids of cassava class A SBE (see FIG. 10) and comprises a 3' untranslated region. Subsequently, a complete clone of the second gene was also recovered (see FIG. 12). The coding portions of the two genes show some slight differences, and the second SBE gene may be considered as functionally equivalent to the corresponding portion of the nucleotide sequence shown in FIG. 4. However, the 3' untranslated regions of the two genes show marked differences. Thus the method of altering a host cell may comprise the use of a sufficient portion of either gene so as to inhibit the expression of the naturally occurring homologous gene. Conveniently, a portion of nucleotide sequence is employed which is conserved between both genes. Alternatively, sufficient portions of both genes may he employed, typically using a single construct to direct the transcription of both introduced sequences.

In addition, as explained above, it may be desired to cause inhibition of expression of the class B SBE (i.e. SBE I) in the same host cell. A number of class B SBE gene sequences are known, including portions of the cassava class B SBE (Salehuzzaman et al., 1994 Plant Science 98, 53–62) and any one of these may prove suitable. Preferably the sequence used is that which derives from the host cell sought to be altered (e.g. when altering the characteristics of a cassava plant cell, it is generally preferred to use sense or anti-sense sequences corresponding exactly to at least portions of the cassava gene whose expression is sought it be inhibited).

In a further aspect the invention provides an altered host cell, into which has been introduced a nucleic acid sequence comprising at least 200 bp and exhibiting at least 88% sequence identity (more preferably at least 90%, and most preferably at least 95% identity) with the corresponding region of the DNA sequence shown in FIGS. 4, 9, 10 or 13, operably linked in the sense or anti-sense orientation to a suitable promoter, said host cell comprising a natural gene sharing sequence homology with the introduced sequence.

The host cell may be a micro-organism (such as a bacterial, fungal or yeast cell) or a plant cell. Conveniently the host cell altered by the method is a cell of a cassava plant, or another plant with starch storage reserves, such as banana, potato, sweet potato, tomato, pea, wheat, barley, oat, maize, or rice plant. Typically the sequence will be introduced in a nucleic acid construct, by way of transformation, transduction, micro-injection or other method known to those skilled in the art. The invention also provides for a plant into which has been introduced a nucleic acid sequence of the invention, or the progeny of such a plant.

The altered plant cell will preferably be grown into an altered plant, using techniques of plant growth and cultivation well-known to those skilled in the art of re-generating plantlets from plant cells.

The invention also provides a method of obtaining starch from an altered plant, the plant being obtained by the method defined above. Starch may he extracted from the plant by any of the known techniques (e.g. milling). The invention further provides starch obtainable from a plant altered by the method defined above, the starch having altered properties compared to starch extracted from an equivalent but unaltered plant. Conveniently the altered starch is obtained from an altered plant selected from the group consisting of cassava, potato, pea, tomato, maize, wheat, barley, oat, sweet potato and rice. Typically the altered starch will have increased amylose content.

The invention will now be further described by way of illustrative examples and with reference to the accompanying drawings, in which:

FIG. 1 is a schematic illustration of the cloning strategy for cassava SBE II. The top line represents the size of a full length clone with distances in kilobases (kb) and arrows representing oligonucleotides (rightward pointing arrows are sense strand, leftward are on opposite strand). The long thick arrow is the open reading frame with start and stop codons shown. Below this are shown the 3' RACE. 5' RACE and PCR clones identified either by the plasmid name (shown in brackets above the line) or the clone number (shown to the left of the clone) for the 5' RACE only. Also shown (by an x) in the 5' RACE clones are positions of small deletions or introns.

FIG. 2 shows the DNA sequence and predicted ORF of csbe2con.seq (SEQ ID NO: 39). This sequence is a consensus of 3' RACE pSJ94 and 5' RACE clones 27/9,11 and 28. The first 64 base pairs are derived from the RoRidT17 adaptor primer/dT tail followed by the SBE sequence. The one long open reading frame is shown in one letter code below the double strand DNA sequence. Also shown is the upstream ORF (MQL . . . LPW). (SEQ ID NO: 40)

FIG. 3 shows an alignment of the 5' region of cassava SBE II csbe2con (SEQ ID NO: 41) and pSJ99 (clones 20 (SEQ ID NO: 42) and 35 (SEQ ID NO: 43)) DNA sequences. Differences from the consensus sequence are shaded.

FIG. 4 shows the DNA sequence (SEQ ID NO: 28) and predicted ORF (SEQ ID NO: 29) of full length cassava SBE II tuber cDNA in pSJ107. The sequence shown is from the CSBE214 (SEQ. ID. NO: 15) to the CSBE218 (SEQ. ID. NO: 19) oligonucleotide. The DNA sequence is sequence ID No. 28 in the attached sequence listing; the amino acid sequence is Seq ID No. 29.

FIG. 5 shows an alignment of 3' region of cassava SBE II pSJ116 (SEQ ID NO: 44) and 125+94 DNA sequences (SEQ ID NO: 45). The top line is the 125+94 sequence and the bottom SJ116 sequence.

FIG. 6 shows an alignment of carboxy terminal region of pSJ116 (SEQ ID NO: 46) and 125+94 protein sequences (SEQ ID NO: 47). The top sequence is from 125+94 and the bottom from pSJ116. Identical amino acid residues are shown with the same letter, conserved changes with a colon and neutral changes with a period.

FIG. 7 shows a phylogenetic tree of starch branching enzyme proteins. The length of each pair of branches represents the distance between sequence pairs. The scale beneath the tree measures the distance between sequences (units indicate the number of substitution events). Dotted lines indicate a negative branch length because of averaging the tree. Zmcon12.pro is maize SBE II, psstb1.pro is pea SBE I (Bhattacharyya et al 1990 Cell 60, 115–121) and atsbe2-1 & 2-2.pro are two SBE II proteins from *Arabidopsis thalania* (Fisher et al 1996 Plant Mol. Biol. 30, 97–108). SJ107.pro is representative of a cassava SBE II sequence, and potsbe2.pro is a potato SBE II sequence known to the inventors.

FIG. 8 is an alignment of SBE II proteins. Protein sequences are indicated in one letter code. The top line represents the consensus sequence, below which is shown the consensus ruler and the individual SBE II sequences (SEQ ID Nos: 54–59). Residues matching the consensus are shaded. Dashes represent gaps introduced to optimise alignment. Sequence identities are shown at the right of the figure and are as FIG. 7, except that SJ107.pro is cassava SBE II (SEQ ID NO: 29).

FIG. 9 shows the DNA sequence (SEQ ID NO: 48) and predicted ORF (SEQ ID NO: 49) of a cassava SBE II cDNA isolated by 3' RACE (plasmid pSJ 101).

FIG. 10 shows the consensus DNA sequence (SEQ ID NO: 50) and predicted ORF (SEQ ID NO: 51) of a second cassava SBE II cDNA isolated by 3' and 5' RACE (sequence designated 125+94 is from plasmid pSJ125 and pSJ94, spliced at the CSBE217, SEQ. ID. NO. 18, oligo sequence).

Figure 11:
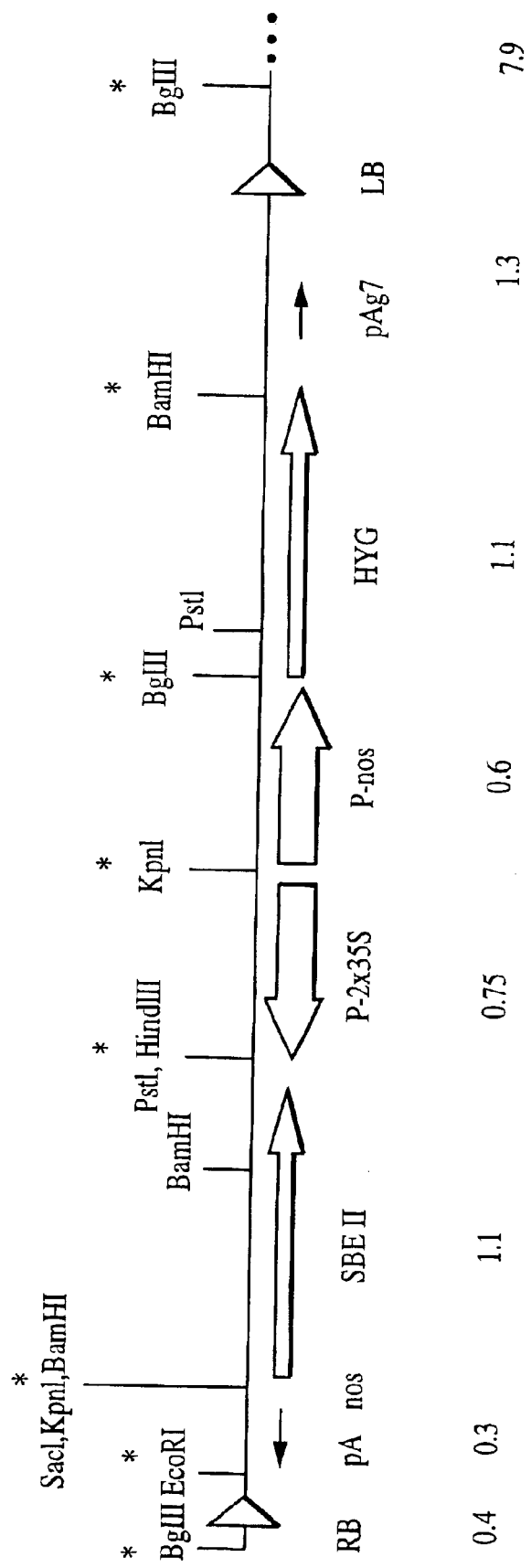

FIG. 11 is a schematic diagram of the plant transformation vector pSJ64. The black line represents the DNA sequence. The hashed line represents the bacterial plasmid backbone (containing the origin of replication and bacterial selection marker) and is not shown in full. The filled triangles represent the T-DNA borders (RB=right border, LB=left border). Relevant restriction enzyme sites are shown above the black line with the approximate distances (in kiloobases) betwen sites marked by an asterisk shown underneath. The thinnest arrows represent polyadenylation signals (pAnos= nopaline synthase, pAg7=Agrobacterium gene 7), the intermediate arrows represent protein coding regions (SBE II=cassava SBE II, HYG=hygromycin resistance gene) and the thick arrows represent promoter regions (P-2×35S= double CaMV 35S promoter, P-nos=nopaline synthase promoter).

Figure 12:
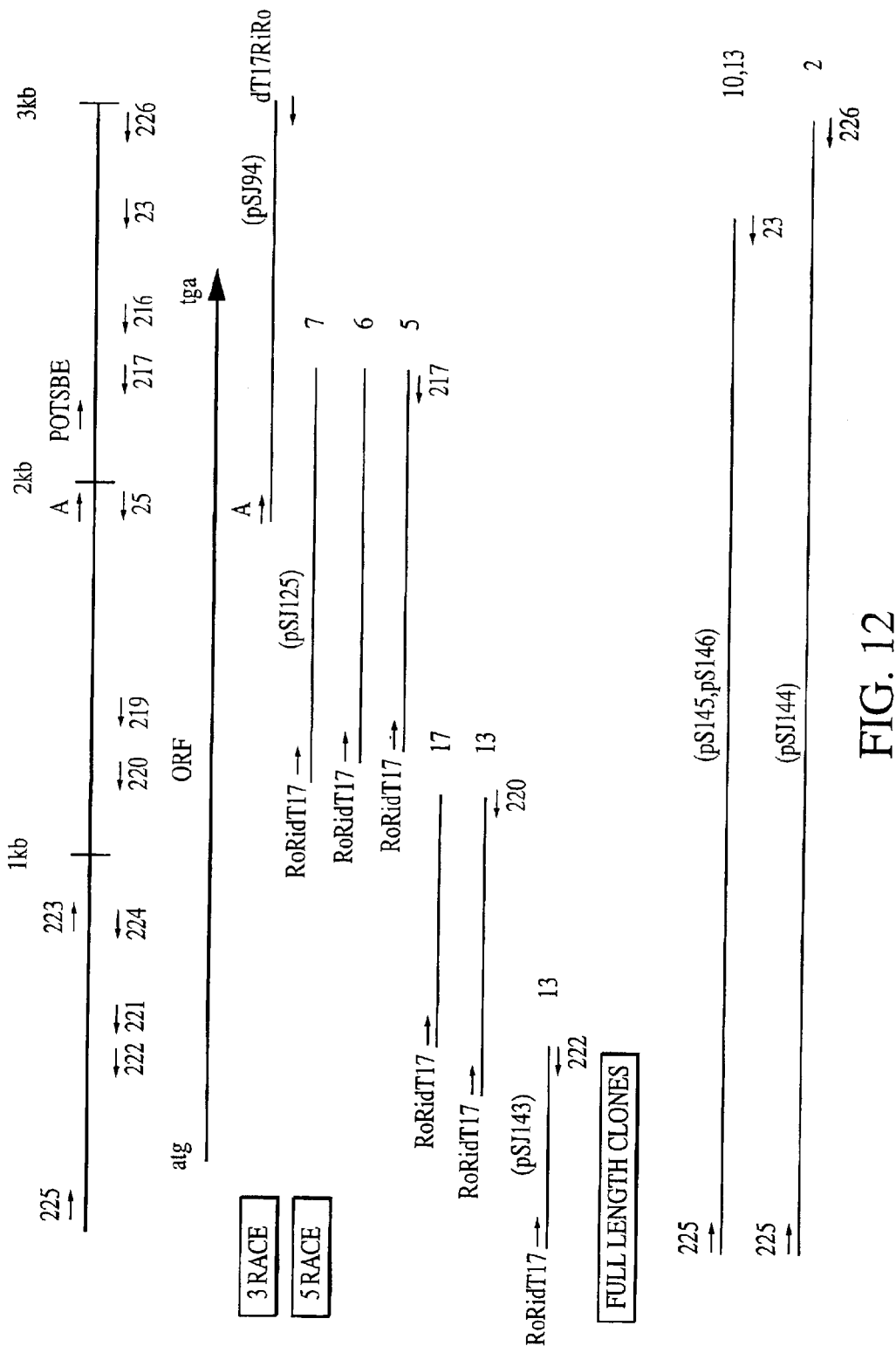

FIG. 12 is a schematic illustration of the cloning strategy used to isolate a second cassava SBE II gene. The top line represents the size of a full length clone with distances in kilobases (kb) and arrows representing oligonucleotides (rightward pointing arrows are sense strand, leftward are on opposite strand). The long thick arrow is the open reading frame with start and stop codons shown. Below this are shown the 3' RACE, 5' RACE and PCR clones identified either by the plasmid name (shown in brackets above the line) or the clone number (shown to the right of the clone).

FIG. 13 shows the DNA sequence (SEQ ID NO: 30) and predicted ORF (SEQ ID NO: 31) of a second full length cassava SBE II tuber cDNA in pSJ146. Nucleotides 35–2760 are SBE II sequence (SEQ ID NO: 52) and the remainder are from the pT7Blue vector (SEQ ID NO: 53). The DNA sequence of FIG. 13 is Seq ID No. 30, and the amino acid sequence is Seq ID No. 31, in the attached sequence listing.

EXAMPLE 1

This example relates to the isolation and cloning of SBE II sequences from cassava.

Recombinant DNA Manipulations

Standard procedures were performed essentially according to Sambrook et al. (1989 Molecular cloning A laboratory manual, 2nd edn. Cold Spring Harbor Laboratory Press, Cold Spring Harbor, N.Y.). DNA sequencing was performed on an ABI automated DNA sequencer and sequences manipulated using DNASTAR software for the Macintosh.

Rapid Amplification of cDNA Ends (RACE) and PCR Conditions

5' and 3' RACE were performed essentially according to Frohman et al., (1988 Proc. Natl. Acad. Sci. USA 85, 8998–9002) but with the following modifications.

For 3' RACE, 5 μg of total RNA was reverse transcribed using 5 pmol of the RACE adaptor RoRidT17 as primer and Stratascript RNAse H-reverse transcriptase (50 U) in a 50 μl reaction according to the manufacturer's instructions (Stratagene). The reaction was incubated for 1 hour at 37° C. and then diluted to 200 μl with TE (10 mM Tris HCl, 1 mM EDTA) pH 8 and stored at 4° C. 2.5 μl of this cDNA was used in a 25 μl PCR reaction with 12.5 pmol of SBE A and Ro primers for 30 cycles of 94° C. 45 sec, 50° C. 25 sec, 72° C. 1 min 30 sec. A second round of PCR (25 cycles) was performed using 1 μl of this reaction as template in a 50 μl reaction under the same conditions. Amplified products were separated by agarose gel electrophoresis and cloned into the pT7Blue vector (Invitrogen).

For the first round of 5' RACE, 5 μg of total leaf RNA was reverse transcribed as described above using 10 pmol of the SBE II gene specific primer CSBE22. This primer was removed from the reaction by diluting to 500 μl with TE and centrifuging twice through a centricon 100 microconcentrator. The concentrated cDNA was then dA-tailed with 9U of terminal deoxynucleotide transferase and 50 μM dATP in a 20 μl reaction in buffer supplied by the manufacturer (BRL). The reaction was incubated for 10 min at 37° C. and 5 min at 65° C. and then diluted to 200 μl with TE pH 8. PCR was performed in a 50 μl volume using 5 μl of tailed cDNA. 2.5 pmol of RoRidT17 and 25 pmol of Ro and CSBE24 primers for 30 cycles of 94° C. 45 sec, 55° C. 25 sec, 72° C. 3 min. Amplified products were separated on a 1% TAE agarose gel, cut out, 200μl of TE was added and melted at 99° C. for 10 min. Five μl of this was re-amplified in a 50 μl volume using CSBE25 and Ri as primers and 25 cycles of 94° C. 45 sec, 55° C. 25 sec, 72° C. 1 min 30 sec. Amplified fragments were separated on a 1% TAE agarose gel, purified on DEAE paper and cloned into pT7Blue.

The second round of 5' RACE was performed using CSBE28 and 29 primers in the first and second round PCR reactions respectively using a new A-tailed cDNA library primed with CSBE27.

A third round of 5' RACE was performed on the same CSBE27 primed cDNA.

Repeat 3' RACE and PCR Cloning

The 3' RACE library (RoRidT17 primed leaf RNA) was used as a template. The first PCR reaction was diluted 1:20 and 1 μl was used in a 50 μl PCR reaction with SBE A and Ri primers and the products were cloned into pT7Blue. The cloned PCR products were screened for the presence or absence of the CSBE23 oligo by colony PCR.

A full length cDNA of cassava SBE II was isolated by PCR from leaf or root cDNA (RoRidT17 primed) using primers CSBE214 and CSBE218 from 2.5 μl of cDNA in a 25 μl reaction and 30 cycles of 94° C. 45 sec, 55° C. 25 sec, 72° C. 2 min.

Complementation of E. coli Mutant KV832

SBE II containing plasmids were transformed into the branching enzyme deficient mutant E. coli KV832 (Keil et al., 1987 Mol. Gen. Genet. 207, 294–301) and cells grown on solid PYG media (0.85% $KH_2PO_4$, 1.1% $K_2HPO_4$, 0.6% yeast extract) containing 1.0% glucose. To test for complementation, a loop of cells was scraped off and resuspended in 150 μl water to which was added 15 μl of Lugol's solution (2 g KI and 1 g $I_2$ per 300 ml water).

RNA Isolation

RNA was isolated from cassava plants by the method of Logemann (1987 Anal. Biochem. 163, 21–26). Leaf RNA was isolated from 0.5 gm of in vitro grown plant tissue. The total yield was 300 μg. Three month old roots (89 gm) were used for isolation of root RNA).

| SBE II specific oligonucleotides | | |
|---|---|---|
| SBE A | ATGGACAAGGATATGTATGA | (Seq ID No. 1) |
| CSBE21 | GGTTTCATGACTTCTGAGCA | (Seq ID No. 2) |
| CSBE22 | TGCTCAGAAGTCATGAAACC | (Seq ID No. 3) |
| CSBE23 | TCCAGTCTCAATATACGTCG | (Seq ID No. 4) |
| CSBE24 | AGGAGTAGATGGTCTGTCGA | (Seq ID No. 5) |
| CSBE25 | TCATACATATCCTTGTCCAT | (Seq ID No. 6) |
| CSBE26 | GGGTGACTTCAATGATGTAC | (Seq ID No. 7) |
| CSBE27 | GGTGTACATCATTGAAGTCA | (Seq ID No. 8) |
| CSBE28 | AATTACTGGCTCCGTACTAC | (Seq ID No. 9) |
| CSBE29 | CATTCCAACGTGCGACTCAT | (Seq ID No. 10) |
| CSBE210 | TACCGGTAATCTAGGTGTTG | (Seq ID No. 11) |
| CSBE211 | GGACCTTGGTTTAGATCCAA | (Seq ID No. 12) |
| CSBE212 | ATGAGTCGCACGTTGGAATG | (Seq ID No. 13) |
| CSBE213 | CAACACCTAGATTACCGGTA | (Seq ID No. 14) |
| CSBE214 | TTAGTTGCGTCAGTTCTCAC | (Seq ID No. 15) |
| CSBE215 | AATATCTATCTCAGCCGGAG | (Seq ID No. 16) |
| CSBE216 | ATCTTAGATAGTCTGCATCA | (Seq ID No. 17) |
| CSBE217 | TGGTTGTTCCCTGGAATTAC | (Seq ID No. 18) |
| CSBE218 | TGCAAGGACCGTGACATCAA | (Seq ID No. 19) |

Results

Cloning of a SBE II Gene from Cassava Leaf

The strategy for cloning a full length cDNA of starch branching enzyme II of cassava is shown in FIG. 1. A comparison of several SBE II (class A) SBE DNA sequences identified a 23 bp region which appears to be completely conserved among most genes (data not shown) and is positioned about one kilobase upstream from the 3' end of the gene. An oligonucleotide primer (designated SBE A) was made to this sequence and used to isolate it partial cDNA clone by 3' RACE PCR from first strand leaf cDNA as illustrated in FIG. 1. An approximately 1100 bp band was amplified, cloned into pT7Blue vector and sequenced. This clone was designated pSJ94 and contained a 1120 bp insert starting with the SBE A oligo and ending with a polyA tail. There was a predicted open reading frame of 235 amino acids which was highly homologous (79% identical) to a potato SBE II also isolated by the inventors (data not shown) suggesting that this clone represented a class A (SBE II) gene.

To obtain the sequence of a full length clone nested primers were made complementary to the 5' end of this sequence and used in 5' RACE PCR to isolate clones from the 5' region of the gene. A total of three rounds of 5' RACE was needed to determine the sequence of the complete gene (i.e. one that has a predicted long ORF preceded by stop codons). It should be noted that during this cloning process several clones (#23, 9, 16) were obtained that had small deletions and in one case (clone 23) there was also a small (120 bp) intron present. These occurrences are not uncommon and probably arise through errors in the PCR process and/or reverse transcription of incompletely processed RNA (heterogeneous nuclear RNA).

The overlapping cDNA fragments could be assembled into a contiguous 3 kb sequence (designated csbe2con.seq) which contained one long predicted ORF as shown in FIG. 2. Several clones in the last round of 5' RACE were obtained which included sequence of the untranslated leader (UTL). All of these clones had an ORF (42 amino acids) 46 bp upstream and out of frame with that of the long ORF.

There Is More than One SBE II Gene in Cassava

In order to determine if the assembled sequence represented that of a single gene, attempts were made to recover by PCR a full length SBE II gene using primers CSBE214 and CSBE23 at the 5' and 3' ends of the csbe2con sequence respectively. All attempts were unsuccessful using either leaf or root cDNA as template. The PCR was therefore repeated with either the 5'- or 3'- most primer and complementary primers along the length of the SBE II gene to determine the size of the largest fragment that could be amplified. With the CSBE214 primer, fragments could he amplified using primers 210, 28, 27 and 22 in order of increasing distance, the latter primer pair amplifying a 2.2 kb band. With the 3' primer CSBE23, only primer pairs with 21 and 26 gave amplification products, the latter being about 1200 bp. These results suggest that the original 3' RACE clone (pSJ94) is derived from a different SBE II gene than the rest of the 5' RACE clones even though the two largest PCR fragments (214+22 and 26+23) overlap by 750 bp and share several primer sites. It is likely that the sequence of the two genes starts to diverge around the CSBE22 primer site such that the 3' end of the corresponding gene does not contain the 23 primer and is not therefore able to amplify a cDNA when used with the 214 primer.

To confirm this, the sequence of the longest 5' PCR fragment (214+22) from two clones (#20 designated pSJ99, & #35) was determined and compared to the consensus sequence csbe2con as shown in FIG. 3. The first 2000 bases are nearly identical (the single base changes might well be PCR errors), however the consensus sequence is significantly different after this. This region corresponds to the original 3' RACE fragment pSJ94 (SBE A+Ri adaptor) and provided evidence that there may be more than one SBE II gene in cassava.

The 3' end corresponding to pSJ99 was therefore cloned as follows: 3' RACE PCR was performed on leaf cDNA using the SBE A oligo as the gene specific primer so that all SBE II genes would be amplified. The cloned DNA fragments were then screened for the presence or absence of the CSBE23 primer by PCR. Two out of 15 clones were positive with the SBE A+Ri primer pair but negative with SBE A+CSBE23 primers. The sequence of these two clones (designated pSJ101, as shown in FIG. 9) demonstrated that they were indeed from an SBE II gene and that they were different from pSJ94. However the overlapping region of pSJ101 (the 3' clone) and pSJ99 (the 5' clone) was identical suggesting that they were derived from the same gene.

To confirm this a primer (CSBE218, SEQ. ID. NO. 19) was made to a region in the 3' UTR (untranslated region) of pSJ101 and used in combination with CSBE214 (SEQ. ID. NO. 15) primer to recover by PCR a full length cDNA from both leaf and root cDNA. These clones were sequenced and designated pSJ106 & pSJ107 respectively. The sequence and predicted ORF of pSJ101 is shown in FIG. 4 (SEQ. ID. NO. 28). The long ORF in plasmid pSJ106 was found to be interrupted by a stop codon (presumably introduced in the PCR process) approximately 1 kb from the 3' end of the gene, therefore another cDNA clone (designated pSJ116) was amplified in a separate reaction, cloned and sequenced. This clone had an intact ORF (data not shown).

There were only a few differences in these two sequences (in the transit peptide aa 27–41: YRRTSSCLSFNFKEA (SEQ ID NO: 34) to DRRTSSCLSFIFKKAA (SEQ ID NO: 35) and L831 in pSJ107 to V in pSJ116 respectively).

An additional 740 bp of sequence of the gene corresponding to the pSJ94 clone was isolated by 5' RACE using the primers CSBE216 and 217, and was designated pSJ125.

This sequence was combined with that of pSJ94 to form a consensus sequence "125+94", as shown in FIG. 10. The sequence of this second gene is about 90% identical at the DNA and protein level to pSJ116, as shown in FIG. 5 and 6, and is clearly a second form of SBE II in cassava. The 3' untranslated regions of the two genes are not related (data not shown).

It was also determined that the full length cassava SBE II genes (from both leaf and tuber) actually encode for active starch branching enzymes since the cloned genes were able to complement the glycogen branching enzyme deficient *E. coli* mutant KV832.

Main Findings

1) A full length cDNA clone of a starch branching enzyme II (SBE II) gene has been cloned from leaves and starch storing roots of cassava. This cDNA encodes a 836 amino acid protein (Mr 95 Kd) and is 86% identical to pea SBE I over the central conserved domain, although the level of sequence identity over the entire coding region is lower than 86%.

2) There is more than one SBE II gene in cassava as a second partial SBE II cDNA was isolated which differs slightly in the protein coding region from the first gene and has no homology in the 3' untranslated region.

3) The isolated full length cDNA from both leaves and roots encodes an active SBE as it complements an *E. coli* mutant deficient in glycogen branching enzyme as assayed by iodine staining.

We have shown that there are SBE II (Class A) gene sequences present in the cassava genome by isolating cDNA fragments using 3' and 5' RACE. From these cDNA fragments a consensus sequence of over 3 kb could be compiled which contained one long open reading frame (FIG. 2) which is highly homologous to other SBE II (class A) genes (data not shown). It is likely that the consensus sequence does not represent that of a single gene since attempts to PCR a full length gene using primers at the 5' and 3' ends of this sequence were not successful. In fact screening of a number of leaf derived 3' RACE cDNAs showed that a second SBE II gene (clone designated pSJ101) was also expressed which is highly homologous within the coding region to the originally isolated cDNA (pSJ94) but has a different 3' UTR. A full length SBE II gene was isolated from leaves and roots by PCR using a new primer to the 3' end of this sequence and the original sequence at the 5' end of the consensus sequence. If the frequency of clones isolated by 3' RACE PCR reflects the abundance of the mRNA levels then this full length gene may he expressed at lower levels in the leaf than the pSJ94 clone (2 out of 15 were the former class, 13/15 the latter). It should be noted that each class is expressed in both leaves and roots as judged by PCR (data not shown). Sequence analysis of the predicted ORF of the leaf and root genes showed only a few differences (4 amino acid changes and one deletion) which could have arisen through PCR errors or, alternatively, there may be more than one nearly identical gene expressed in these tissues.

A comparison of all known SBE II protein sequences shows that the cassava SBE II gene is most closely related to the pea gene (FIG. 8). The two proteins are 86.3% identical over a 686 amino acid range which extends from the triple proline "elbow" (Burton et al., 1995 Plant J. 7, 3–15) to the conserved VVYA (SEQ ID NO: 36) sequence immediately preceding the C-terminal extensions (data not shown). All SBE II proteins are conserved over this range in that they are at least 80% similar to each other. Remarkably however, the sequence conservation between the pea, potato and cassava SBE II proteins also extends to the N-terminal transit peptide, especially the first 12 amino acids of the precursor protein and the region surrounding the mature terminus of the pea protein (AKFSRDS (SEQ ID NO: 37)). Because the proteins are so similar around this region it can be predicted that the mature terminus of the cassava SBE II protein is likely to be GKSSHES (SEQ ID NO: 38). The precursor has a predicted molecular mass of 96 kD and the mature protein a predicted molecule mass of 91.3 kD. The cassava SBE II has a short acidic tail at the C-terminal although this is not as long or as acidic as that found in the pea or potato proteins. The significance of this acidic tail, if any, remains to be determined. One notable difference between the amino acid sequence of cassava SBE II and all other SBE II proteins is the presence of the sequence NSKH (SEQ ID NO: 32) at around position 697 instead of the conserved sequence DAD/EY (SEQ ID NO: 33). Although this conserved region forms part of a predicted $\alpha$-helix (number 8) of the catalytic $(\beta/\alpha)_8$ barrel domain (Burton et al 1995 cited previously), this difference does not abolish the SBE activity of the cassava protein as this gene can still complement the glycogen branching deletion mutant of *E. coli*. It may however affect the specificity of the protein. An interesting point is that the other cassava SBE II clone pSJ94 has the conserved sequence DADY (SEQ ID NO. 33).

One other point of interest concerning the sequence of the SBE II gene is the presence of an upstream ATG in the 5' UTR. This ATG could initiate a small peptide of 42 amino acids which would terminate downstream of the predicted initiating methionine codon of the SBE II precursor. If this does occur then the translation of the SBE II protein from this mRNA is likely to be inefficient as ribosomes normally initiate at the 5' most ATG in the mRNA. However the first ATG is in a poorer Kozak context than the SBE II initiator and it may be too close to the 5' end of the message to initiate efficiently (14 nucleotides) thus allowing initiation to occur at the correct ATG.

In conclusion we have shown that cassava does have SBE II gene sequences, that they are expressed in both leaves and tubers and that more than one gene exists.

EXAMPLE 2

Cloning of a Second Full Length Cassava SBE II Gene

Methods

| Oligonucleotides | | |
|---|---|---|
| CSBE219 | CTTTATCTATTAAAGACTTC | (Seq ID No. 20) |
| CSBE220 | CAAAAAGTTTGTGACATGG | (Seq ID No. 21) |
| CSBE221 | TCACTTTTTCCAATGCTAAT | (Seq ID No. 22) |
| CSBE222 | TCTCATGCAATGGAACCGAC | (Seq ID No. 23) |
| CSBE223 | CAGATGTCCTGACTCGGAAT | (Seq ID No. 24) |
| CSBE224 | ATTCCGAGTCAGGACATCTG | (Seq ID No. 25) |
| CSBE225 | CGCATTTCTCGCTATTGCTT | (Seq ID No. 26) |
| CSBE226 | CACAGGCCCAAGTGAAGAAT | (Seq ID No. 27) |

The 5' end of the gene corresponding to the 3' RACE clone pSJ94 was isolated in three rounds of 5' RACE. Prior to performing the first round of 5' RACE, 5 µg of total leaf RNA was reverse transcribed in a 20 µl reaction using conditions as decribed by the manufacturer (Superscript enzyme, BRL) and 10 pmol of the SBE II gene specific primer CSBE23. Primers were then removed and the cDNA tailed with dATP as described above. The first round of 5' RACE used primers CSBE216 and Ro. This PCR reaction was diluted 1:20 and used as a template for a second round of amplification using primers CSBE217 and Ri. The gene specific primers were designed so that they would preferentially hybridise to the SBE II sequence in pSJ94. Amplified products appeared as a smear of approximately 600–1200 bp when subjected to electrophoresis on a 1% TAE agarose gel.

This smear was excised and DNA purified using a Qiaquick column (Qiagen) before ligation to the pT7Blue vector. Several clones were sequenced and clone #7 was designated pSJ125. New primers (CSBE219 and 220) were designed to hybridise to the 5' end of pSJ125 and a second round of 5' RACE was performed using the same CSBE23 primed library. Two fragments of 600 and 800 bp were cloned and sequenced (clones 13,17). Primers CSBE221 and 222 were designed to hybridise to the 5' sequence of the longest clone (#13) and a third round of 5' RACE was performed on a new library (5 µg total leaf RNA reverse transcribed with Superscript using CSBE220 as primer and then dATP tailed with TdT from Boehringer Mannheim). Fragments of approximately 500 bp were amplified, cloned and sequenced. Clone #13, was designated pSJ143. The process is illustrated schematically in FIG. 12.

To isolate a full length gene as a contiguous sequence, a new primer (CSBE225) was designed to hybridise to the 5' end of clone pSJ143 and used with one of the primers (CSBE226 or 23) in the 3' end of clone pSJ94, in a PCR reaction using RoRidT17 primed leaf cDNA as template. Use of primer CSBE226 resulted in production of Clone #2 (designated pSJ144), and use of primer CSBE23 resulted in production of Clones #10 and 13 (designated pSJ145 and pSJ146 respectively). Only pSJ146 was sequenced fully.

Results

Isolation of a Second Full Length Cassava SBE II Gene

A full length clone for a second SBE II gene was isolated by extending the sequence of pSJ94 in three rounds of 5' RACE as illustrated schematically in FIG. 12. In each round of 5' RACE, primers were designed that would preferentially hybridise to the new sequence rather than to the gene represented by pSJ 116. In the final round of 5' RACE, three clones were obtained that had the initiating methione codon, and none of these had upstream ATGs. The overlapping cDNA fragments (sequences of the 5' RACE clones pSJ143, 13, pSJ125 and the 3' RACE clone pSJ94) could be assembled into a consensus sequence of approximately 3 kb which was designated csbe2-2.seq. This sequence contained one long ORF with a predicted size of 848 aa (M, 97 kDa). The full length gene was then isolated as a contiguous sequence by PCR amplification from RoRidT17 primed leaf cDNA using primers at the 5' (CSBE225) and 3' (CSBE23 or CSBE226) ends of the RACE clones. One clone, designated pSJ146, was sequenced and the restriction map is shown along with the predicted amino acid sequence in FIG. 13.

Sequence Homologies Between SBE II Genes

The two cassava genes (pSJ116 and pSJ146) share 88.8% identity at the DNA level over the entire coding region (data not shown). The homology extends about 50 bases outside of this region but beyond this the untranslated regions show no similarity (data not shown). At the protein level the two genes show 86% identity over the entire ORF (data not shown). The two genes are more closely related to each other than to any other SBE II. Between species, the pea SBE I shows the most homology to the cassava SBE II genes.

EXAMPLE 3

Construction of Plant Transformation Vectors and Transformation of Cassava with Antisense Starch Branching Enzyme Genes This example describes in detail how a portion of the SBE II gene isolated from cassava may be introduced into cassava plants to create transgenic plants with altered properties.

An 1100 bp Hind III—Sac I fragment of cassava SBE II (from plasmid pSJ94) was cloned into the Hind III—Sac I sites of the plant transformation vector pSJ64 (FIG. 11). This placed the SBE II gene in an antisense orientation between the 2×35S CaMV promoter and the nopaline synthase polyadenylation signal. pSJ64 is a derivative of the binary vector pGPTV-HYG (Becker et al., 1992 Plant Molecular Biology 20: 1195–1197) modified by inclusion of an approximately 750 bp fragment of pJIT60 (Guerineau et al 1992 Plant Mol. Biol. 18, 815–818) containing the duplicated cauliflower mosaic virus (CaMV) 35S promoter (Cabb-JI strain, equivalent to nucleotides 7040 to 7376 duplicated upstream of 7040 to 7433, as described by Frank et al., 1980 Cell 21, 285–294) to replace the GUS coding sequence. A similar construct was made with the cassava SBE II sequence from plasmid pSJ101.

These plasmids are then introduced into *Agrobacterium tumefaciens* LBA4404 by a direct DNA uptake method (An et al. Binary vectors, In: Plant Molecular Biology Manual (ed Galvin and Schilperoort) AD 1988 pp 1–19) and can be used to transform cassava somatic embryos by selecting on hygromycin as described by Li et al. (1996, Nature Biotechnology 14, 736–740).

SEQUENCE LISTING

```
<160> NUMBER OF SEQ ID NOS: 60

<210> SEQ ID NO 1
<211> LENGTH: 20
<212> TYPE: DNA
<213> ORGANISM: Artificial sequence
<220> FEATURE:
<223> OTHER INFORMATION: SEB A oligonucleotide

<400> SEQUENCE: 1
atggacaagg atatgtatga                                               20

<210> SEQ ID NO 2
<211> LENGTH: 20
<212> TYPE: DNA
<213> ORGANISM: Artificial sequence
<220> FEATURE:
<223> OTHER INFORMATION: CSBE21 oligonucleotide
```

```
<400> SEQUENCE: 2
ggtttcatga cttctgagca                                          20

<210> SEQ ID NO 3
<211> LENGTH: 20
<212> TYPE: DNA
<213> ORGANISM: Artificial sequence
<220> FEATURE:
<223> OTHER INFORMATION: CSBE22 oligonucleotide

<400> SEQUENCE: 3
tgctcagaag tcatgaaacc                                          20

<210> SEQ ID NO 4
<211> LENGTH: 20
<212> TYPE: DNA
<213> ORGANISM: Artificial sequence
<220> FEATURE:
<223> OTHER INFORMATION: CSBE23 oligonucleotide

<400> SEQUENCE: 4
tccagtctca atatacgtcg                                          20

<210> SEQ ID NO 5
<211> LENGTH: 20
<212> TYPE: DNA
<213> ORGANISM: Artificial sequence
<220> FEATURE:
<223> OTHER INFORMATION: CSBE24 oligonucleotide

<400> SEQUENCE: 5
aggagtagat ggtctgtcga                                          20

<210> SEQ ID NO 6
<211> LENGTH: 20
<212> TYPE: DNA
<213> ORGANISM: Artificial sequence
<220> FEATURE:
<223> OTHER INFORMATION: CSBE25 oligonucleotide

<400> SEQUENCE: 6
tcatacatat ccttgtccat                                          20

<210> SEQ ID NO 7
<211> LENGTH: 20
<212> TYPE: DNA
<213> ORGANISM: Artificial sequence
<220> FEATURE:
<223> OTHER INFORMATION: CSBE26 oligonucleotide

<400> SEQUENCE: 7
gggtgacttc aatgatgtac                                          20

<210> SEQ ID NO 8
<211> LENGTH: 20
<212> TYPE: DNA
<213> ORGANISM: Artificial sequence
<220> FEATURE:
<223> OTHER INFORMATION: CSBE27 oligonucleotide

<400> SEQUENCE: 8
ggtgtacatc attgaagtca                                          20

<210> SEQ ID NO 9
```

```
<211> LENGTH: 20
<212> TYPE: DNA
<213> ORGANISM: Artificial sequence
<220> FEATURE:
<223> OTHER INFORMATION: CSBE28 oligonucleotide

<400> SEQUENCE: 9
aattactggc tccgtactac                                               20

<210> SEQ ID NO 10
<211> LENGTH: 20
<212> TYPE: DNA
<213> ORGANISM: Artificial sequence
<220> FEATURE:
<223> OTHER INFORMATION: CSBE29 oligonucleotide

<400> SEQUENCE: 10
cattccaacg tgcgactcat                                               20

<210> SEQ ID NO 11
<211> LENGTH: 20
<212> TYPE: DNA
<213> ORGANISM: Artificial sequence
<220> FEATURE:
<223> OTHER INFORMATION: CSBE210 oligonucleotide

<400> SEQUENCE: 11
taccggtaat ctaggtgttg                                               20

<210> SEQ ID NO 12
<211> LENGTH: 20
<212> TYPE: DNA
<213> ORGANISM: Artificial sequence
<220> FEATURE:
<223> OTHER INFORMATION: CSBE211 oligonucleotide

<400> SEQUENCE: 12
ggaccttggt ttagatccaa                                               20

<210> SEQ ID NO 13
<211> LENGTH: 20
<212> TYPE: DNA
<213> ORGANISM: Artificial sequence
<220> FEATURE:
<223> OTHER INFORMATION: CSBE212 oligonucleotide

<400> SEQUENCE: 13
atgagtcgca cgttggaatg                                               20

<210> SEQ ID NO 14
<211> LENGTH: 20
<212> TYPE: DNA
<213> ORGANISM: Artificial sequence
<220> FEATURE:
<223> OTHER INFORMATION: CSBE213 oligonucleotide

<400> SEQUENCE: 14
caacacctag attaccggta                                               20

<210> SEQ ID NO 15
<211> LENGTH: 20
<212> TYPE: DNA
<213> ORGANISM: Artificial sequence
<220> FEATURE:
<223> OTHER INFORMATION: CSBE214 oligonucleotide

<400> SEQUENCE: 15
```
ttagttgcgt cagttctcac                                            20

<210> SEQ ID NO 16
<211> LENGTH: 20
<212> TYPE: DNA
<213> ORGANISM: Artificial sequence
<220> FEATURE:
<223> OTHER INFORMATION: CSBE215 oligonucleotide

<400> SEQUENCE: 16
aatatctatc tcagccggag                                            20

<210> SEQ ID NO 17
<211> LENGTH: 20
<212> TYPE: DNA
<213> ORGANISM: Artificial sequence
<220> FEATURE:
<223> OTHER INFORMATION: CSBE216 oligonucleotide

<400> SEQUENCE: 17
atcttagata gtctgcatca                                            20

<210> SEQ ID NO 18
<211> LENGTH: 20
<212> TYPE: DNA
<213> ORGANISM: Artificial sequence
<220> FEATURE:
<223> OTHER INFORMATION: CSBE217 oligonucleotide

<400> SEQUENCE: 18
tggttgttcc ctggaattac                                            20

<210> SEQ ID NO 19
<211> LENGTH: 20
<212> TYPE: DNA
<213> ORGANISM: Artificial sequence
<220> FEATURE:
<223> OTHER INFORMATION: CSBE218 oligonucleotide

<400> SEQUENCE: 19
tgcaaggacc gtgacatcaa                                            20

<210> SEQ ID NO 20
<211> LENGTH: 20
<212> TYPE: DNA
<213> ORGANISM: Artificial sequence
<220> FEATURE:
<223> OTHER INFORMATION: CSBE219 oligonucleotide

<400> SEQUENCE: 20
ctttatctat taaagacttc                                            20

<210> SEQ ID NO 21
<211> LENGTH: 20
<212> TYPE: DNA
<213> ORGANISM: Artificial sequence
<220> FEATURE:
<223> OTHER INFORMATION: CSBE220 oligonucleotide

<400> SEQUENCE: 21
caaaaaagtt tgtgacatgg                                            20

<210> SEQ ID NO 22
<211> LENGTH: 20
<212> TYPE: DNA

<213> ORGANISM: Artificial sequence
<220> FEATURE:
<223> OTHER INFORMATION: CSBE221 oligonucleotide

<400> SEQUENCE: 22
tcactttttc caatgctaat                                              20

<210> SEQ ID NO 23
<211> LENGTH: 20
<212> TYPE: DNA
<213> ORGANISM: Artificial sequence
<220> FEATURE:
<223> OTHER INFORMATION: CSBE222 oligonucleotide

<400> SEQUENCE: 23
tctcatgcaa tggaaccgac                                              20

<210> SEQ ID NO 24
<211> LENGTH: 20
<212> TYPE: DNA
<213> ORGANISM: Artificial sequence
<220> FEATURE:
<223> OTHER INFORMATION: CSBE223 oligonucleotide

<400> SEQUENCE: 24
cagatgtcct gactcggaat                                              20

<210> SEQ ID NO 25
<211> LENGTH: 20
<212> TYPE: DNA
<213> ORGANISM: Artificial sequence
<220> FEATURE:
<223> OTHER INFORMATION: CSBE224 oligonucleotide

<400> SEQUENCE: 25
attccgagtc aggacatctg                                              20

<210> SEQ ID NO 26
<211> LENGTH: 20
<212> TYPE: DNA
<213> ORGANISM: Artificial sequence
<220> FEATURE:
<223> OTHER INFORMATION: CSBE225 oligonucleotide

<400> SEQUENCE: 26
cgcatttctc gctattgctt                                              20

<210> SEQ ID NO 27
<211> LENGTH: 20
<212> TYPE: DNA
<213> ORGANISM: Artificial sequence
<220> FEATURE:
<223> OTHER INFORMATION: CSBE226 oligonucleotide

<400> SEQUENCE: 27
cacaggccca agtgaagaat                                              20

<210> SEQ ID NO 28
<211> LENGTH: 2588
<212> TYPE: DNA
<213> ORGANISM: Artificial sequence
<220> FEATURE:
<223> OTHER INFORMATION: cassava SBE II tuber cDNA in pSJ107
<220> FEATURE:
<221> NAME/KEY: CDS
<222> LOCATION: (21)..(2531)

```
<400> SEQUENCE: 28
ctctctaact tctcagcgaa atg gga cac tac acc ata tca gga ata cgt ttt        53
                     Met Gly His Tyr Thr Ile Ser Gly Ile Arg Phe
                      1               5                  10 cct tgt gct cca ctc tgc aaa tct caa tct acc ggc ttc cat ggc tat         101
Pro Cys Ala Pro Leu Cys Lys Ser Gln Ser Thr Gly Phe His Gly Tyr
             15                  20                  25 cgg agg acc tcc tct tgc ctt tcc ttc aac ttc aag gag gcg ttt tct         149
Arg Arg Thr Ser Ser Cys Leu Ser Phe Asn Phe Lys Glu Ala Phe Ser
         30                  35                  40 agg agg gtc ttc tct gga aag tca tct cat gaa tct gac tcc tca aat         197
Arg Arg Val Phe Ser Gly Lys Ser Ser His Glu Ser Asp Ser Ser Asn
     45                  50                  55 gta atg gtc act gct tct aaa aga gtc ctt cct gat ggt cgg att gaa         245
Val Met Val Thr Ala Ser Lys Arg Val Leu Pro Asp Gly Arg Ile Glu
 60                  65                  70                  75 tgc tat tct tct tca aca gat caa ttg gaa gcc cct ggc aca gtt tca         293
Cys Tyr Ser Ser Ser Thr Asp Gln Leu Glu Ala Pro Gly Thr Val Ser
                 80                  85                  90 gaa gaa tcc cag gtg ctt act gat gtt gag agt ctc att atg gat gat         341
Glu Glu Ser Gln Val Leu Thr Asp Val Glu Ser Leu Ile Met Asp Asp
             95                 100                 105 aag att gtt gaa gat gaa gta aat aaa gaa tct gtt cca atg cgg gag         389
Lys Ile Val Glu Asp Glu Val Asn Lys Glu Ser Val Pro Met Arg Glu
         110                 115                 120 aca gtt agc atc aga aaa att gga tct aaa cca agg tcc att cct cca         437
Thr Val Ser Ile Arg Lys Ile Gly Ser Lys Pro Arg Ser Ile Pro Pro
     125                 130                 135 ccc ggc aga ggg caa aga ata tat gac ata gat cca agc ttg aca ggc         485
Pro Gly Arg Gly Gln Arg Ile Tyr Asp Ile Asp Pro Ser Leu Thr Gly
140                 145                 150                 155 ttt cgt caa cac cta gat tac cgg tat tca cag tac aaa aga ctc cga         533
Phe Arg Gln His Leu Asp Tyr Arg Tyr Ser Gln Tyr Lys Arg Leu Arg
                 160                 165                 170 gaa gaa att gac aag tat gaa ggt agt ctg gat gca ttt tct cgt ggc         581
Glu Glu Ile Asp Lys Tyr Glu Gly Ser Leu Asp Ala Phe Ser Arg Gly
             175                 180                 185 tat gaa aag ttt ggt ttc tca cgc agt gaa aca gga ata act tat aga         629
Tyr Glu Lys Phe Gly Phe Ser Arg Ser Glu Thr Gly Ile Thr Tyr Arg
         190                 195                 200 gag tgg gca cca gga gct acg tgg gct gca ttg att gga gat ttc aat         677
Glu Trp Ala Pro Gly Ala Thr Trp Ala Ala Leu Ile Gly Asp Phe Asn
     205                 210                 215 aac tgg aat cct aat gca gat gtc atg act cag aat gag tgt ggt gtc         725
Asn Trp Asn Pro Asn Ala Asp Val Met Thr Gln Asn Glu Cys Gly Val
220                 225                 230                 235 tgg gag atc ttt ttg ccg aat aat gca gat ggt tca cca cca att ccc         773
Trp Glu Ile Phe Leu Pro Asn Asn Ala Asp Gly Ser Pro Pro Ile Pro
                 240                 245                 250 cat ggt tct cga gta aag ata cgc atg gat act cca tct ggc aac aaa         821
His Gly Ser Arg Val Lys Ile Arg Met Asp Thr Pro Ser Gly Asn Lys
             255                 260                 265 gat tct att cct gct tgg atc aag ttc tca gtt caa gca cca ggt gaa         869
Asp Ser Ile Pro Ala Trp Ile Lys Phe Ser Val Gln Ala Pro Gly Glu
         270                 275                 280 ctc cca tat aat ggc ata tac tat gat cct ccc gag gag gag aag tat         917
Leu Pro Tyr Asn Gly Ile Tyr Tyr Asp Pro Pro Glu Glu Glu Lys Tyr
     285                 290                 295 gtg ttc aaa aat cct cag cca aag aga cca aaa tca ctt cgg att tat         965
```

```
                                                              -continued

Val Phe Lys Asn Pro Gln Pro Lys Arg Pro Lys Ser Leu Arg Ile Tyr
300                 305                 310                 315 gag tcg cac gtt gga atg agt agt acg gag cca gta att aac aca tat    1013
Glu Ser His Val Gly Met Ser Ser Thr Glu Pro Val Ile Asn Thr Tyr
                320                 325                 330 gcc aac ttt aga gat gat gtg ctt cct cgc atc aaa aag ctt ggc tac    1061
Ala Asn Phe Arg Asp Asp Val Leu Pro Arg Ile Lys Lys Leu Gly Tyr
            335                 340                 345 aat gct gtt cag ctc atg gct att caa gag cat tca tat tat gct agt    1109
Asn Ala Val Gln Leu Met Ala Ile Gln Glu His Ser Tyr Tyr Ala Ser
        350                 355                 360 ttt ggg tat cac gtc aca aac ttt tat gca gct agc agc cga ttt gga    1157
Phe Gly Tyr His Val Thr Asn Phe Tyr Ala Ala Ser Ser Arg Phe Gly
    365                 370                 375 act cct gat gat tta aag tct cta ata gat aaa gct cac gag tta ggt    1205
Thr Pro Asp Asp Leu Lys Ser Leu Ile Asp Lys Ala His Glu Leu Gly
380                 385                 390                 395 ctt ctt gtt ctc atg gat att gtt cat agc cat gca tca act aat acg    1253
Leu Leu Val Leu Met Asp Ile Val His Ser His Ala Ser Thr Asn Thr
                400                 405                 410 ttg gat ggg ctg aat atg ttt gat ggt acg gat ggt cac tac ttt cac    1301
Leu Asp Gly Leu Asn Met Phe Asp Gly Thr Asp Gly His Tyr Phe His
            415                 420                 425 tct gga cca cgg ggt cat cat tgg atg tgg gac tct cgc ctt ttc aac    1349
Ser Gly Pro Arg Gly His His Trp Met Trp Asp Ser Arg Leu Phe Asn
        430                 435                 440 tat ggg agc tgg gag gtt cta agg ttt ctt ctt tca aat gca agg tgg    1397
Tyr Gly Ser Trp Glu Val Leu Arg Phe Leu Leu Ser Asn Ala Arg Trp
    445                 450                 455 tgg ttg gat gag tac aag ttt gat ggg ttc aga ttt gat ggg gtg act    1445
Trp Leu Asp Glu Tyr Lys Phe Asp Gly Phe Arg Phe Asp Gly Val Thr
460                 465                 470                 475 tca atg atg tac acc cat cat gga ttg cag gta gat ttt acc ggc aac    1493
Ser Met Met Tyr Thr His His Gly Leu Gln Val Asp Phe Thr Gly Asn
                480                 485                 490 tac aat gaa tac ttt gga tat gca act gat gta gat gct gtg gtt tat    1541
Tyr Asn Glu Tyr Phe Gly Tyr Ala Thr Asp Val Asp Ala Val Val Tyr
            495                 500                 505 ttg atg ctg ttg aat gat atg att cat ggt ctc ttc cca gag gct gtc    1589
Leu Met Leu Leu Asn Asp Met Ile His Gly Leu Phe Pro Glu Ala Val
        510                 515                 520 acc att ggt gaa gat gtt agt gga atg cca aca gtt tgc att ccg gtt    1637
Thr Ile Gly Glu Asp Val Ser Gly Met Pro Thr Val Cys Ile Pro Val
    525                 530                 535 gaa gat ggt ggt gtt ggc ttt gat tat cgt ctc cac atg gct gtt gct    1685
Glu Asp Gly Gly Val Gly Phe Asp Tyr Arg Leu His Met Ala Val Ala
540                 545                 550                 555 gat aaa tgg gtt gag att att cag aag aga gat gaa gat tgg aaa atg    1733
Asp Lys Trp Val Glu Ile Ile Gln Lys Arg Asp Glu Asp Trp Lys Met
                560                 565                 570 ggt gac att gta cat atg ctg acc aac agg cgg tgg ttg gaa aag tgt    1781
Gly Asp Ile Val His Met Leu Thr Asn Arg Arg Trp Leu Glu Lys Cys
            575                 580                 585 gtt tct tat gct gaa agt cat gac cag gcc ctt gtt ggt gac aaa act    1829
Val Ser Tyr Ala Glu Ser His Asp Gln Ala Leu Val Gly Asp Lys Thr
        590                 595                 600 att gca ttt tgg ctg atg gac aag gat atg tat gac ttc atg gct ctt    1877
Ile Ala Phe Trp Leu Met Asp Lys Asp Met Tyr Asp Phe Met Ala Leu
    605                 610                 615
```

```
gac aga cca tct act cct ctc ata gat cgt gga gta gca ttg cac aaa    1925
Asp Arg Pro Ser Thr Pro Leu Ile Asp Arg Gly Val Ala Leu His Lys
620             625                 630                 635 atg atc agg ctt att acc atg gga tta ggc gga gaa gga tat ttg aat    1973
Met Ile Arg Leu Ile Thr Met Gly Leu Gly Gly Glu Gly Tyr Leu Asn
            640                 645                 650 ttt atg gga aat gaa ttt gga cac ccc gag tgg att gat ttt cca aga    2021
Phe Met Gly Asn Glu Phe Gly His Pro Glu Trp Ile Asp Phe Pro Arg
655                 660                 665 ggt gat cta cat ctt ccc agt ggt aaa ttt gtt cct ggg aac aat tac    2069
Gly Asp Leu His Leu Pro Ser Gly Lys Phe Val Pro Gly Asn Asn Tyr
        670                 675                 680 agt tat gat aaa tgc cgg cgt agg ttt gat cta ggc aat tca aag cat    2117
Ser Tyr Asp Lys Cys Arg Arg Arg Phe Asp Leu Gly Asn Ser Lys His
685                 690                 695 ctg aga tat cat gga atg caa gag ttt gat caa gca att cag cat ctt    2165
Leu Arg Tyr His Gly Met Gln Glu Phe Asp Gln Ala Ile Gln His Leu
700                 705                 710                 715 gaa gaa gcc tat ggt ttc atg act tct gag cac caa tac ata tca cgg    2213
Glu Glu Ala Tyr Gly Phe Met Thr Ser Glu His Gln Tyr Ile Ser Arg
            720                 725                 730 aag gat gaa agg gat cgg atc att gtc ttc gag agg gga aac ctc gtt    2261
Lys Asp Glu Arg Asp Arg Ile Ile Val Phe Glu Arg Gly Asn Leu Val
                735                 740                 745 ttt gta ttc aat ttt cat tgg act agc agc tat tcg gat tac cga gtt    2309
Phe Val Phe Asn Phe His Trp Thr Ser Ser Tyr Ser Asp Tyr Arg Val
            750                 755                 760 ggc tgc tta aag cca gga aag tac aag ata gtc ttg gat tca gat gat    2357
Gly Cys Leu Lys Pro Gly Lys Tyr Lys Ile Val Leu Asp Ser Asp Asp
765                 770                 775 cct ttg ttt gga ggc ttt ggc agg ctt agt cat gat gca gag cac ttc    2405
Pro Leu Phe Gly Gly Phe Gly Arg Leu Ser His Asp Ala Glu His Phe
780                 785                 790                 795 agc ttt gaa ggg tgg tac gat aac cgg cct cga tcc ttc atg gtg tac    2453
Ser Phe Glu Gly Trp Tyr Asp Asn Arg Pro Arg Ser Phe Met Val Tyr
            800                 805                 810 aca cca tgt aga aca gca gtg gtc tat gct tta gtg gag gat gaa gtg    2501
Thr Pro Cys Arg Thr Ala Val Val Tyr Ala Leu Val Glu Asp Glu Val
                815                 820                 825 gag aat gaa ttg gaa cct gtc gcc ggt taa gatatatctt aacaacaggt      2551
Glu Asn Glu Leu Glu Pro Val Ala Gly
            830                 835 tctgaagcag gaatgccatt attgatcttc ctatgtt                           2588

<210> SEQ ID NO 29
<211> LENGTH: 836
<212> TYPE: PRT
<213> ORGANISM: Artificial sequence
<220> FEATURE:
<223> OTHER INFORMATION: cassava SBE II tuber cDNA in pSJ107

<400> SEQUENCE: 29

Met Gly His Tyr Thr Ile Ser Gly Ile Arg Phe Pro Cys Ala Pro Leu
1               5                   10                  15

Cys Lys Ser Gln Ser Thr Gly Phe His Gly Tyr Arg Arg Thr Ser Ser
            20                  25                  30

Cys Leu Ser Phe Asn Phe Lys Glu Ala Phe Ser Arg Arg Val Phe Ser
        35                  40                  45

Gly Lys Ser Ser His Glu Ser Asp Ser Ser Asn Val Met Val Thr Ala
    50                  55                  60
```

-continued

```
Ser Lys Arg Val Leu Pro Asp Gly Arg Ile Glu Cys Tyr Ser Ser Ser
 65                  70                  75                  80

Thr Asp Gln Leu Glu Ala Pro Gly Thr Val Ser Glu Ser Gln Val
                 85                  90                  95

Leu Thr Asp Val Glu Ser Leu Ile Met Asp Asp Lys Ile Val Glu Asp
                100                 105                 110

Glu Val Asn Lys Glu Ser Val Pro Met Arg Glu Thr Val Ser Ile Arg
                115                 120                 125

Lys Ile Gly Ser Lys Pro Arg Ser Ile Pro Pro Gly Arg Gly Gln
    130                 135                 140

Arg Ile Tyr Asp Ile Asp Pro Ser Leu Thr Gly Phe Arg Gln His Leu
145                 150                 155                 160

Asp Tyr Arg Tyr Ser Gln Tyr Lys Arg Leu Arg Glu Glu Ile Asp Lys
                165                 170                 175

Tyr Glu Gly Ser Leu Asp Ala Phe Ser Arg Gly Tyr Glu Lys Phe Gly
                180                 185                 190

Phe Ser Arg Ser Glu Thr Gly Ile Thr Tyr Arg Glu Trp Ala Pro Gly
    195                 200                 205

Ala Thr Trp Ala Ala Leu Ile Gly Asp Phe Asn Asn Trp Asn Pro Asn
210                 215                 220

Ala Asp Val Met Thr Gln Asn Glu Cys Gly Val Trp Glu Ile Phe Leu
225                 230                 235                 240

Pro Asn Asn Ala Asp Gly Ser Pro Ile Pro His Gly Ser Arg Val
                245                 250                 255

Lys Ile Arg Met Asp Thr Pro Ser Gly Asn Lys Asp Ser Ile Pro Ala
                260                 265                 270

Trp Ile Lys Phe Ser Val Gln Ala Pro Gly Glu Leu Pro Tyr Asn Gly
                275                 280                 285

Ile Tyr Tyr Asp Pro Pro Glu Glu Glu Lys Tyr Val Phe Lys Asn Pro
    290                 295                 300

Gln Pro Lys Arg Pro Lys Ser Leu Arg Ile Tyr Glu Ser His Val Gly
305                 310                 315                 320

Met Ser Ser Thr Glu Pro Val Ile Asn Thr Tyr Ala Asn Phe Arg Asp
                325                 330                 335

Asp Val Leu Pro Arg Ile Lys Lys Leu Gly Tyr Asn Ala Val Gln Leu
                340                 345                 350

Met Ala Ile Gln Glu His Ser Tyr Tyr Ala Ser Phe Gly Tyr His Val
                355                 360                 365

Thr Asn Phe Tyr Ala Ala Ser Ser Arg Phe Gly Thr Pro Asp Asp Leu
    370                 375                 380

Lys Ser Leu Ile Asp Lys Ala His Glu Leu Gly Leu Leu Val Leu Met
385                 390                 395                 400

Asp Ile Val His Ser His Ala Ser Thr Asn Thr Leu Asp Gly Leu Asn
                405                 410                 415

Met Phe Asp Gly Thr Asp Gly His Tyr Phe His Ser Gly Pro Arg Gly
                420                 425                 430

His His Trp Met Trp Asp Ser Arg Leu Phe Asn Tyr Gly Ser Trp Glu
    435                 440                 445

Val Leu Arg Phe Leu Leu Ser Asn Ala Arg Trp Trp Leu Asp Glu Tyr
    450                 455                 460

Lys Phe Asp Gly Phe Arg Phe Asp Gly Val Thr Ser Met Met Tyr Thr
465                 470                 475                 480
```

-continued

```
His His Gly Leu Gln Val Asp Phe Thr Gly Asn Tyr Asn Glu Tyr Phe
            485                 490                 495

Gly Tyr Ala Thr Asp Val Asp Ala Val Val Tyr Leu Met Leu Leu Asn
            500                 505                 510

Asp Met Ile His Gly Leu Phe Pro Glu Ala Val Thr Ile Gly Glu Asp
            515                 520                 525

Val Ser Gly Met Pro Thr Val Cys Ile Pro Val Glu Asp Gly Gly Val
        530                 535                 540

Gly Phe Asp Tyr Arg Leu His Met Ala Val Ala Asp Lys Trp Val Glu
545                 550                 555                 560

Ile Ile Gln Lys Arg Asp Glu Asp Trp Lys Met Gly Asp Ile Val His
                565                 570                 575

Met Leu Thr Asn Arg Arg Trp Leu Glu Lys Cys Val Ser Tyr Ala Glu
            580                 585                 590

Ser His Asp Gln Ala Leu Val Gly Asp Lys Thr Ile Ala Phe Trp Leu
        595                 600                 605

Met Asp Lys Asp Met Tyr Asp Phe Met Ala Leu Asp Arg Pro Ser Thr
610                 615                 620

Pro Leu Ile Asp Arg Gly Val Ala Leu His Lys Met Ile Arg Leu Ile
625                 630                 635                 640

Thr Met Gly Leu Gly Gly Glu Gly Tyr Leu Asn Phe Met Gly Asn Glu
                645                 650                 655

Phe Gly His Pro Glu Trp Ile Asp Phe Pro Arg Gly Asp Leu His Leu
            660                 665                 670

Pro Ser Gly Lys Phe Val Pro Gly Asn Asn Tyr Ser Tyr Asp Lys Cys
        675                 680                 685

Arg Arg Arg Phe Asp Leu Gly Asn Ser Lys His Leu Arg Tyr His Gly
690                 695                 700

Met Gln Glu Phe Asp Gln Ala Ile Gln His Leu Glu Glu Ala Tyr Gly
705                 710                 715                 720

Phe Met Thr Ser Glu His Gln Tyr Ile Ser Arg Lys Asp Glu Arg Asp
                725                 730                 735

Arg Ile Ile Val Phe Glu Arg Gly Asn Leu Val Phe Val Phe Asn Phe
            740                 745                 750

His Trp Thr Ser Ser Tyr Ser Asp Tyr Arg Val Gly Cys Leu Lys Pro
        755                 760                 765

Gly Lys Tyr Lys Ile Val Leu Asp Ser Asp Asp Pro Leu Phe Gly Gly
770                 775                 780

Phe Gly Arg Leu Ser His Asp Ala Glu His Phe Ser Phe Glu Gly Trp
785                 790                 795                 800

Tyr Asp Asn Arg Pro Arg Ser Phe Met Val Tyr Thr Pro Cys Arg Thr
                805                 810                 815

Ala Val Val Tyr Ala Leu Val Glu Asp Glu Val Glu Asn Glu Leu Glu
            820                 825                 830

Pro Val Ala Gly
        835

<210> SEQ ID NO 30
<211> LENGTH: 2805
<212> TYPE: DNA
<213> ORGANISM: Artificial sequence
<220> FEATURE:
<223> OTHER INFORMATION: cassava SBE II tuber cDNA in pSJ146
<220> FEATURE:
<221> NAME/KEY: CDS
<222> LOCATION: (131)..(2677)
```

<400> SEQUENCE: 30

```
agtgaattcg agctcggtac ccggggatcc gattcgcatt tctcgctatt gctttccgtt      60
tatttccata tataaaatat caaatctaat cacttgcgcc atttctatct ctctccaaac     120
tctcaccgaa atg gta tac tac act gta tca ggc ata cgt ttt cct tgt       169
            Met Val Tyr Tyr Thr Val Ser Gly Ile Arg Phe Pro Cys
             1               5                  10 gca cct tca ctc tac aaa tct cag ctc acc agc ttc cat ggc ggt cga      217
Ala Pro Ser Leu Tyr Lys Ser Gln Leu Thr Ser Phe His Gly Gly Arg
 15              20                  25 agg acc tct tct ggc ctt tcc ttc ctc ttg aag aag gag ctg ttt cct      265
Arg Thr Ser Ser Gly Leu Ser Phe Leu Leu Lys Lys Glu Leu Phe Pro
 30              35                  40                  45 cgg aag atc ttt gct gga aag tcc tct tat gaa tct gac tcc tca aat      313
Arg Lys Ile Phe Ala Gly Lys Ser Ser Tyr Glu Ser Asp Ser Ser Asn
         50                  55                  60 tta act gtc tct gca tct gag aag gtc ctt gtt cct gat gat cag att      361
Leu Thr Val Ser Ala Ser Glu Lys Val Leu Val Pro Asp Asp Gln Ile
     65                  70                  75 gat ggc tct tct tct tca aca tat caa tta gaa acc act ggc aca gtt      409
Asp Gly Ser Ser Ser Ser Thr Tyr Gln Leu Glu Thr Thr Gly Thr Val
         80                  85                  90 ttg gag gaa tcc cag gtt ctt ggt gat gca gag agt ctt gtg atg gaa      457
Leu Glu Glu Ser Gln Val Leu Gly Asp Ala Glu Ser Leu Val Met Glu
 95                 100                 105 gat gat aag aat gtt gag gag gat gaa gta aaa aaa gag tcg gtt cca      505
Asp Asp Lys Asn Val Glu Glu Asp Glu Val Lys Lys Glu Ser Val Pro
110                 115                 120                 125 ttg cat gag aca att agc att gga aaa agt gaa tct aaa cca agg tcc      553
Leu His Glu Thr Ile Ser Ile Gly Lys Ser Glu Ser Lys Pro Arg Ser
                130                 135                 140 att cct cca cct ggc agt ggg cag aga ata tat gac ata gat cca agc      601
Ile Pro Pro Pro Gly Ser Gly Gln Arg Ile Tyr Asp Ile Asp Pro Ser
             145                 150                 155 ttg gca ggt ttc cgt cag cat ctt gac tac cga tat tca cag tac aaa      649
Leu Ala Gly Phe Arg Gln His Leu Asp Tyr Arg Tyr Ser Gln Tyr Lys
         160                 165                 170 agg ctg cgt gag gaa att gac aag tat gaa ggt ggt ttg gat gca ttc      697
Arg Leu Arg Glu Glu Ile Asp Lys Tyr Glu Gly Gly Leu Asp Ala Phe
     175                 180                 185 tct cgt gga ttt gaa aag ttt ggt ttc tta cgc agt gaa aca gga ata      745
Ser Arg Gly Phe Glu Lys Phe Gly Phe Leu Arg Ser Glu Thr Gly Ile
190                 195                 200                 205 act tat agg gaa tgg gca cct gga gct acg tgg gct gca ctt att gga      793
Thr Tyr Arg Glu Trp Ala Pro Gly Ala Thr Trp Ala Ala Leu Ile Gly
                210                 215                 220 gat ttc aac aat tgg aat cct aat gca gat gtc atg act cgg aat gag      841
Asp Phe Asn Asn Trp Asn Pro Asn Ala Asp Val Met Thr Arg Asn Glu
             225                 230                 235 ttt ggt gtc tgg gag att ttt ttg cca aat aac gca gat ggt tca cca      889
Phe Gly Val Trp Glu Ile Phe Leu Pro Asn Asn Ala Asp Gly Ser Pro
         240                 245                 250 cca att cct cat ggt tct cga gta aag ata cgc atg gat act cca tct      937
Pro Ile Pro His Gly Ser Arg Val Lys Ile Arg Met Asp Thr Pro Ser
     255                 260                 265 ggc atc aaa gat tca att cct gct tgg atc aag ttc tca gtt cag gca      985
Gly Ile Lys Asp Ser Ile Pro Ala Trp Ile Lys Phe Ser Val Gln Ala
270                 275                 280                 285
```

-continued

| | | |
|---|---|---|
| cct ggt gaa atc cca tac aat gcc ata tac tat gat cca cca aag gag<br>Pro Gly Glu Ile Pro Tyr Asn Ala Ile Tyr Tyr Asp Pro Pro Lys Glu<br>              290                  295                      300 | 1033 | |
| gag aag tat gtg ttc aaa cat cct cag cca aag aga cca aaa tca ctt<br>Glu Lys Tyr Val Phe Lys His Pro Gln Pro Lys Arg Pro Lys Ser Leu<br>          305                  310                  315 | 1081 | |
| agg att tat gaa tct cat gtt ggg atg agt agt atg gag cca ata att<br>Arg Ile Tyr Glu Ser His Val Gly Met Ser Ser Met Glu Pro Ile Ile<br>       320                  325                  330 | 1129 | |
| aac aca tat gcc aac ttt aga gat gat atg ctt cct cgc atc aaa aag<br>Asn Thr Tyr Ala Asn Phe Arg Asp Asp Met Leu Pro Arg Ile Lys Lys<br>335                  340                  345 | 1177 | |
| ctt ggc tac aat gct gtt cag atc atg gct att caa gag cat tcc tat<br>Leu Gly Tyr Asn Ala Val Gln Ile Met Ala Ile Gln Glu His Ser Tyr<br>350                  355                  360                  365 | 1225 | |
| tat gct agt ttt ggg tac cat gtc aca aac ttt ttt gca cct agc agc<br>Tyr Ala Ser Phe Gly Tyr His Val Thr Asn Phe Phe Ala Pro Ser Ser<br>              370                  375                  380 | 1273 | |
| cga ttt gga act cct gat gat ttg aag tct tta ata gat aaa gct cat<br>Arg Phe Gly Thr Pro Asp Asp Leu Lys Ser Leu Ile Asp Lys Ala His<br>                  385                  390                  395 | 1321 | |
| gag tta ggg ctg ctt gtt ctc atg gat att gtt cat agc cat gcg tca<br>Glu Leu Gly Leu Leu Val Leu Met Asp Ile Val His Ser His Ala Ser<br>       400                  405                  410 | 1369 | |
| aat aat acg ttg gat ggg ctg aac atg ttt gat ggt acg gat agt cac<br>Asn Asn Thr Leu Asp Gly Leu Asn Met Phe Asp Gly Thr Asp Ser His<br>415                  420                  425 | 1417 | |
| tac ttc cac tcc gga tca cgg ggt cat cat tgg ttg tgg gac tct cgc<br>Tyr Phe His Ser Gly Ser Arg Gly His His Trp Leu Trp Asp Ser Arg<br>430                  435                  440                  445 | 1465 | |
| ctt ttc aac tat gga agc tgg gag gtg cta aga ttt ctt ctt tca aat<br>Leu Phe Asn Tyr Gly Ser Trp Glu Val Leu Arg Phe Leu Leu Ser Asn<br>              450                  455                  460 | 1513 | |
| gca aga tgg tgg ttg gaa gag tac agg ttt gat ggt ttt aga ttt gat<br>Ala Arg Trp Trp Leu Glu Glu Tyr Arg Phe Asp Gly Phe Arg Phe Asp<br>                  465                  470                  475 | 1561 | |
| ggg gtg act tcc atg atg tac act ccc cat ggg ttg cag gta gct ttt<br>Gly Val Thr Ser Met Met Tyr Thr Pro His Gly Leu Gln Val Ala Phe<br>       480                  485                  490 | 1609 | |
| act ggc aac tac aat gag tac ttt gga tat gca act gat gta gat gct<br>Thr Gly Asn Tyr Asn Glu Tyr Phe Gly Tyr Ala Thr Asp Val Asp Ala<br>495                  500                  505 | 1657 | |
| gtg att tat ttg atg ctt gtg aat gat atg att cac ggt ctt ttc cct<br>Val Ile Tyr Leu Met Leu Val Asn Asp Met Ile His Gly Leu Phe Pro<br>510                  515                  520                  525 | 1705 | |
| gag gct gtt acc att ggt gaa gat gtt agc gga aag cca aca ttt tgc<br>Glu Ala Val Thr Ile Gly Glu Asp Val Ser Gly Lys Pro Thr Phe Cys<br>              530                  535                  540 | 1753 | |
| att cca gtg gaa gat ggt ggt gtt gga ttt gat tac cgt ctc cac atg<br>Ile Pro Val Glu Asp Gly Gly Val Gly Phe Asp Tyr Arg Leu His Met<br>                  545                  550                  555 | 1801 | |
| gcc att gcc gat aaa tgg att gag att ctt aag aag aga gat gag gac<br>Ala Ile Ala Asp Lys Trp Ile Glu Ile Leu Lys Lys Arg Asp Glu Asp<br>              560                  565                  570 | 1849 | |
| tgg aaa atg ggt gac att gtg cat aca ctc acc aac aga agg tgg ttg<br>Trp Lys Met Gly Asp Ile Val His Thr Leu Thr Asn Arg Arg Trp Leu<br>       575                  580                  585 | 1897 | |
| gaa aaa tgt gtt gct tat gct gaa agt cat gac caa gct ctt gtt ggt<br>Glu Lys Cys Val Ala Tyr Ala Glu Ser His Asp Gln Ala Leu Val Gly<br>590                  595                  600                  605 | 1945 | |

| | | |
|---|---|---|
| gac aaa act att gca ttt tgg ctg atg gac aag gac atg tac gac ttc<br>Asp Lys Thr Ile Ala Phe Trp Leu Met Asp Lys Asp Met Tyr Asp Phe<br>610                                  615                           620 | 1993 |
| atg gct cgt gac aga cca tct act cct ctt ata gat cgt gga ata gca<br>Met Ala Arg Asp Arg Pro Ser Thr Pro Leu Ile Asp Arg Gly Ile Ala<br>625                               630                           635 | 2041 |
| ttg cac aaa atg atc agg ctt att acc atg ggc tta ggc gga gaa gga<br>Leu His Lys Met Ile Arg Leu Ile Thr Met Gly Leu Gly Gly Glu Gly<br>640                              645                          650 | 2089 |
| tat ttg aat ttt atg gga aat gaa ttt gga cat cct gag tgg att gat<br>Tyr Leu Asn Phe Met Gly Asn Glu Phe Gly His Pro Glu Trp Ile Asp<br>655                              660                         665 | 2137 |
| ttt cca aga ggg gat cga cat ctg ccc aat ggt aaa gta att cca ggg<br>Phe Pro Arg Gly Asp Arg His Leu Pro Asn Gly Lys Val Ile Pro Gly<br>670                           675                         680                     685 | 2185 |
| aac aac cac agt tat gat aaa tgc cgt cgt aga ttt gat cta ggt gat<br>Asn Asn His Ser Tyr Asp Lys Cys Arg Arg Arg Phe Asp Leu Gly Asp<br>                      690                           695                          700 | 2233 |
| gca gac tat cta aga tat cat gga atg caa gag ttt gat cag gca atg<br>Ala Asp Tyr Leu Arg Tyr His Gly Met Gln Glu Phe Asp Gln Ala Met<br>705                              710                         715 | 2281 |
| caa cat ctt gaa gaa gcc tat ggt ttc atg act tct gag cac cag tat<br>Gln His Leu Glu Glu Ala Tyr Gly Phe Met Thr Ser Glu His Gln Tyr<br>720                           725                         730 | 2329 |
| ata tca cgg aag gat gaa gga gat cgg atc att gtc ttt gag agg gga<br>Ile Ser Arg Lys Asp Glu Gly Asp Arg Ile Ile Val Phe Glu Arg Gly<br>735                              740                         745 | 2377 |
| aac ctt gtt ttt gta ttc aac ttt cat tgg act aac agc tat tca gat<br>Asn Leu Val Phe Val Phe Asn Phe His Trp Thr Asn Ser Tyr Ser Asp<br>750                           755                           760                     765 | 2425 |
| tac cga gtt ggc tgc ttc aag tca gga aag tac aag att gtt ttg gac<br>Tyr Arg Val Gly Cys Phe Lys Ser Gly Lys Tyr Lys Ile Val Leu Asp<br>                      770                           775                          780 | 2473 |
| tcg gat gat ggc ttg ttt gga ggc ttc aac agg ctt agt cat gat gcc<br>Ser Asp Asp Gly Leu Phe Gly Gly Phe Asn Arg Leu Ser His Asp Ala<br>785                              790                         795 | 2521 |
| gag cac ttc acc ttt gac ggg tgg tat gat aac cgg cct cgg tcc ttc<br>Glu His Phe Thr Phe Asp Gly Trp Tyr Asp Asn Arg Pro Arg Ser Phe<br>800                           805                         810 | 2569 |
| atg gta tat gca cca tct agg aca gca gtg gtc tat gct tta gta gaa<br>Met Val Tyr Ala Pro Ser Arg Thr Ala Val Val Tyr Ala Leu Val Glu<br>815                           820                         825 | 2617 |
| gat gaa gag aat gaa gca gag aat gaa gta gaa agt gaa gtg aaa cca<br>Asp Glu Glu Asn Glu Ala Glu Asn Glu Val Glu Ser Glu Val Lys Pro<br>830                              835                         840                     845 | 2665 |
| gcc tcc ggc tga gatagatatt tagtaagagg atccctaaa gcaggaatgg<br>Ala Ser Gly | 2717 |
| ttaacctgtg catctgcatt gaacgacgta tattgagact ggaaatccat atgactagta | 2777 |
| gatcctctag agtcgacctg caggcatg | 2805 |

<210> SEQ ID NO 31
<211> LENGTH: 848
<212> TYPE: PRT
<213> ORGANISM: Artificial sequence
<220> FEATURE:
<223> OTHER INFORMATION: cassava SBE II tuber cDNA in pSJ146

<400> SEQUENCE: 31

Met Val Tyr Tyr Thr Val Ser Gly Ile Arg Phe Pro Cys Ala Pro Ser

-continued

```
  1                   5                  10                  15
Leu Tyr Lys Ser Gln Leu Thr Ser Phe His Gly Gly Arg Arg Thr Ser
                 20                  25                  30
Ser Gly Leu Ser Phe Leu Leu Lys Lys Glu Leu Phe Pro Arg Lys Ile
             35                  40                  45
Phe Ala Gly Lys Ser Ser Tyr Glu Ser Asp Ser Ser Asn Leu Thr Val
         50                  55                  60
Ser Ala Ser Glu Lys Val Leu Val Pro Asp Asp Gln Ile Asp Gly Ser
 65                  70                  75                  80
Ser Ser Ser Thr Tyr Gln Leu Glu Thr Thr Gly Thr Val Leu Glu Glu
                 85                  90                  95
Ser Gln Val Leu Gly Asp Ala Glu Ser Leu Val Met Glu Asp Asp Lys
                100                 105                 110
Asn Val Glu Glu Asp Glu Val Lys Lys Glu Ser Val Pro Leu His Glu
            115                 120                 125
Thr Ile Ser Ile Gly Lys Ser Glu Ser Lys Pro Arg Ser Ile Pro Pro
130                 135                 140
Pro Gly Ser Gly Gln Arg Ile Tyr Asp Ile Asp Pro Ser Leu Ala Gly
145                 150                 155                 160
Phe Arg Gln His Leu Asp Tyr Arg Tyr Ser Gln Tyr Lys Arg Leu Arg
                165                 170                 175
Glu Glu Ile Asp Lys Tyr Glu Gly Gly Leu Asp Ala Phe Ser Arg Gly
                180                 185                 190
Phe Glu Lys Phe Gly Phe Leu Arg Ser Glu Thr Gly Ile Thr Tyr Arg
            195                 200                 205
Glu Trp Ala Pro Gly Ala Thr Trp Ala Ala Leu Ile Gly Asp Phe Asn
    210                 215                 220
Asn Trp Asn Pro Asn Ala Asp Val Met Thr Arg Asn Glu Phe Gly Val
225                 230                 235                 240
Trp Glu Ile Phe Leu Pro Asn Asn Ala Asp Gly Ser Pro Pro Ile Pro
                245                 250                 255
His Gly Ser Arg Val Lys Ile Arg Met Asp Thr Pro Ser Gly Ile Lys
                260                 265                 270
Asp Ser Ile Pro Ala Trp Ile Lys Phe Ser Val Gln Ala Pro Gly Glu
            275                 280                 285
Ile Pro Tyr Asn Ala Ile Tyr Tyr Asp Pro Pro Lys Glu Glu Lys Tyr
        290                 295                 300
Val Phe Lys His Pro Gln Pro Lys Arg Pro Lys Ser Leu Arg Ile Tyr
305                 310                 315                 320
Glu Ser His Val Gly Met Ser Ser Met Glu Pro Ile Ile Asn Thr Tyr
                325                 330                 335
Ala Asn Phe Arg Asp Asp Met Leu Pro Arg Ile Lys Lys Leu Gly Tyr
                340                 345                 350
Asn Ala Val Gln Ile Met Ala Ile Gln Glu His Ser Tyr Tyr Ala Ser
            355                 360                 365
Phe Gly Tyr His Val Thr Asn Phe Phe Ala Pro Ser Ser Arg Phe Gly
        370                 375                 380
Thr Pro Asp Asp Leu Lys Ser Leu Ile Asp Lys Ala His Glu Leu Gly
385                 390                 395                 400
Leu Leu Val Leu Met Asp Ile Val His Ser His Ala Ser Asn Asn Thr
                405                 410                 415
Leu Asp Gly Leu Asn Met Phe Asp Gly Thr Asp Ser His Tyr Phe His
                420                 425                 430
```

-continued

```
Ser Gly Ser Arg Gly His His Trp Leu Trp Asp Ser Arg Leu Phe Asn
        435                 440                 445
Tyr Gly Ser Trp Glu Val Leu Arg Phe Leu Leu Ser Asn Ala Arg Trp
    450                 455                 460
Trp Leu Glu Glu Tyr Arg Phe Asp Gly Phe Arg Phe Asp Gly Val Thr
465                 470                 475                 480
Ser Met Met Tyr Thr Pro His Gly Leu Gln Val Ala Phe Thr Gly Asn
                485                 490                 495
Tyr Asn Glu Tyr Phe Gly Tyr Ala Thr Asp Val Asp Ala Val Ile Tyr
            500                 505                 510
Leu Met Leu Val Asn Asp Met Ile His Gly Leu Phe Pro Glu Ala Val
        515                 520                 525
Thr Ile Gly Glu Asp Val Ser Gly Lys Pro Thr Phe Cys Ile Pro Val
    530                 535                 540
Glu Asp Gly Gly Val Gly Phe Asp Tyr Arg Leu His Met Ala Ile Ala
545                 550                 555                 560
Asp Lys Trp Ile Glu Ile Leu Lys Lys Arg Asp Glu Asp Trp Lys Met
                565                 570                 575
Gly Asp Ile Val His Thr Leu Thr Asn Arg Arg Trp Leu Glu Lys Cys
            580                 585                 590
Val Ala Tyr Ala Glu Ser His Asp Gln Ala Leu Val Gly Asp Lys Thr
        595                 600                 605
Ile Ala Phe Trp Leu Met Asp Lys Asp Met Tyr Asp Phe Met Ala Arg
    610                 615                 620
Asp Arg Pro Ser Thr Pro Leu Ile Asp Arg Gly Ile Ala Leu His Lys
625                 630                 635                 640
Met Ile Arg Leu Ile Thr Met Gly Leu Gly Gly Glu Gly Tyr Leu Asn
                645                 650                 655
Phe Met Gly Asn Glu Phe Gly His Pro Glu Trp Ile Asp Phe Pro Arg
            660                 665                 670
Gly Asp Arg His Leu Pro Asn Gly Lys Val Ile Pro Gly Asn Asn His
        675                 680                 685
Ser Tyr Asp Lys Cys Arg Arg Phe Asp Leu Gly Asp Ala Asp Tyr
    690                 695                 700
Leu Arg Tyr His Gly Met Gln Glu Phe Asp Gln Ala Met Gln His Leu
705                 710                 715                 720
Glu Glu Ala Tyr Gly Phe Met Thr Ser Glu His Gln Tyr Ile Ser Arg
                725                 730                 735
Lys Asp Glu Gly Asp Arg Ile Ile Val Phe Glu Arg Gly Asn Leu Val
            740                 745                 750
Phe Val Phe Asn Phe His Trp Thr Asn Ser Tyr Ser Asp Tyr Arg Val
        755                 760                 765
Gly Cys Phe Lys Ser Gly Lys Tyr Lys Ile Val Leu Asp Ser Asp Asp
    770                 775                 780
Gly Leu Phe Gly Gly Phe Asn Arg Leu Ser His Asp Ala Glu His Phe
785                 790                 795                 800
Thr Phe Asp Gly Trp Tyr Asp Asn Arg Pro Arg Ser Phe Met Val Tyr
                805                 810                 815
Ala Pro Ser Arg Thr Ala Val Val Tyr Ala Leu Val Glu Asp Glu Glu
            820                 825                 830
Asn Glu Ala Glu Asn Glu Val Glu Ser Glu Val Lys Pro Ala Ser Gly
        835                 840                 845
```

```
<210> SEQ ID NO 32
<211> LENGTH: 4
<212> TYPE: PRT
<213> ORGANISM: Artificial sequence
<220> FEATURE:
<223> OTHER INFORMATION: amino acid sequence within SBE class A enzyme
      of cassava

<400> SEQUENCE: 32

Asn Ser Lys His
1

<210> SEQ ID NO 33
<211> LENGTH: 4
<212> TYPE: PRT
<213> ORGANISM: Artificial sequence
<220> FEATURE:
<223> OTHER INFORMATION: conserved sequence within SBE class A enzyme
      of cassava
<220> FEATURE:
<221> NAME/KEY: MISC_FEATURE
<222> LOCATION: (3)..(3)
<223> OTHER INFORMATION: X can be either Asp or Glu

<400> SEQUENCE: 33

Asp Ala Xaa Tyr
1

<210> SEQ ID NO 34
<211> LENGTH: 15
<212> TYPE: PRT
<213> ORGANISM: Artificial sequence
<220> FEATURE:
<223> OTHER INFORMATION: amino acid sequence in clone pSJ107

<400> SEQUENCE: 34

Tyr Arg Arg Thr Ser Ser Cys Leu Ser Phe Asn Phe Lys Glu Ala
1               5                   10                  15

<210> SEQ ID NO 35
<211> LENGTH: 16
<212> TYPE: PRT
<213> ORGANISM: Artificial sequence
<220> FEATURE:
<223> OTHER INFORMATION: amino acid sequence in clone pSJ116

<400> SEQUENCE: 35

Asp Arg Arg Thr Ser Ser Cys Leu Ser Phe Ile Phe Lys Lys Ala Ala
1               5                   10                  15

<210> SEQ ID NO 36
<211> LENGTH: 4
<212> TYPE: PRT
<213> ORGANISM: Artificial sequence
<220> FEATURE:
<223> OTHER INFORMATION: conserved sequence in SBEII proteins

<400> SEQUENCE: 36

Val Val Tyr Ala
1

<210> SEQ ID NO 37
<211> LENGTH: 7
<212> TYPE: PRT
<213> ORGANISM: Artificial sequence
<220> FEATURE:
<223> OTHER INFORMATION: mature terminus of pea protein
```

```
<400> SEQUENCE: 37

Ala Lys Phe Ser Arg Asp Ser
1               5

<210> SEQ ID NO 38
<211> LENGTH: 7
<212> TYPE: PRT
<213> ORGANISM: Artificial sequence
<220> FEATURE:
<223> OTHER INFORMATION: predicted mature terminus of cassava SBEII
      protein

<400> SEQUENCE: 38

Gly Lys Ser Ser His Glu Ser
1               5

<210> SEQ ID NO 39
<211> LENGTH: 3074
<212> TYPE: DNA
<213> ORGANISM: Manihot esculenta
<220> FEATURE:
<221> NAME/KEY: CDS
<222> LOCATION: (127)..(2658)
<220> FEATURE:
<221> NAME/KEY: modified_base
<222> LOCATION: (58)
<223> OTHER INFORMATION: a, t, c, g, other or unknown

<400> SEQUENCE: 39
tatggattga catcgataat acgactcact ataggggattt cttttttttt cttttttgntt      60 tttaaaaaaa gttgaacatg caattagttg cgtcagttct cacactctct ctaacttctc      120 agcgaa atg gga cac tac acc ata tca gga ata cgt ttt cct tgt gct         168
       Met Gly His Tyr Thr Ile Ser Gly Ile Arg Phe Pro Cys Ala
       1               5                   10 cca ctc cgc aaa tct caa tct acc ggc ttc cat ggt gat cga agg acc         216
Pro Leu Arg Lys Ser Gln Ser Thr Gly Phe His Gly Asp Arg Arg Thr
15                  20                  25                  30 tcc tct tgc ctt tcc ttc aac ttc aag aag gcg gcg ttt tct agg agg         264
Ser Ser Cys Leu Ser Phe Asn Phe Lys Lys Ala Ala Phe Ser Arg Arg
                35                  40                  45 gtc ttc tct gga aag tca tct cat gaa tct gac tcc tca aat gta atg         312
Val Phe Ser Gly Lys Ser Ser His Glu Ser Asp Ser Ser Asn Val Met
            50                  55                  60 gtc act gcg tct aaa aga gtc ctt cct gat ggt cgg att gaa tgc tat         360
Val Thr Ala Ser Lys Arg Val Leu Pro Asp Gly Arg Ile Glu Cys Tyr
65                  70                  75 tct tct tca aca gat caa ttg gaa gcc cct ggc aca gtt tca gaa gaa         408
Ser Ser Ser Thr Asp Gln Leu Glu Ala Pro Gly Thr Val Ser Glu Glu
        80                  85                  90 tcc cag gtg ctt act gat gtt gag agt ctc att atg gat gat aag att         456
Ser Gln Val Leu Thr Asp Val Glu Ser Leu Ile Met Asp Asp Lys Ile
95                  100                 105                 110 gtt gaa gat gaa gta aat aaa gaa tct gtt cca atg cgg gag aca gtt         504
Val Glu Asp Glu Val Asn Lys Glu Ser Val Pro Met Arg Glu Thr Val
                115                 120                 125 agc atc gga aaa att gga tct aaa cca agg tcc att cct cca ccc ggc         552
Ser Ile Gly Lys Ile Gly Ser Lys Pro Arg Ser Ile Pro Pro Pro Gly
            130                 135                 140 aga ggg caa aga ata tat gac ata gat cca agc ttg aca ggc ttt cgt         600
Arg Gly Gln Arg Ile Tyr Asp Ile Asp Pro Ser Leu Thr Gly Phe Arg
        145                 150                 155 caa cac cta gat tac cgg tat tca cag tac aaa aga ctc cga gaa gaa         648
```

```

Gln His Leu Asp Tyr Arg Tyr Ser Gln Tyr Lys Arg Leu Arg Glu Glu
    160                 165                 170 att gac aag tat gaa ggt agt ctg gat gca ttt tct cgt ggc tat gaa        696
Ile Asp Lys Tyr Glu Gly Ser Leu Asp Ala Phe Ser Arg Gly Tyr Glu
175                 180                 185                 190 aag ttt ggt ttc tca cgc agt gaa aca gga ata act tat aga gag tgg        744
Lys Phe Gly Phe Ser Arg Ser Glu Thr Gly Ile Thr Tyr Arg Glu Trp
                195                 200                 205 gca cca gga gct acg tgg gct gca ttg att gga gat ttc aat aac tgg        792
Ala Pro Gly Ala Thr Trp Ala Ala Leu Ile Gly Asp Phe Asn Asn Trp
            210                 215                 220 aat cct aat gca gat gtc atg act cag aat gag tgt ggt gtc tgg gag        840
Asn Pro Asn Ala Asp Val Met Thr Gln Asn Glu Cys Gly Val Trp Glu
        225                 230                 235 atc ttt ttg ccg aat aat gca gat ggt tca cca cca att ccc cat ggt        888
Ile Phe Leu Pro Asn Asn Ala Asp Gly Ser Pro Pro Ile Pro His Gly
    240                 245                 250 tct cga gta aag ata cgc atg gat act cca tct ggc aac aaa gat tct        936
Ser Arg Val Lys Ile Arg Met Asp Thr Pro Ser Gly Asn Lys Asp Ser
255                 260                 265                 270 att cct gct tgg atc aag ttc tca gtt caa gca cca ggt gaa ctc cca        984
Ile Pro Ala Trp Ile Lys Phe Ser Val Gln Ala Pro Gly Glu Leu Pro
                275                 280                 285 tat aat ggc ata tac tat gat cct ccc gag gag gag aag tat gtg ttc       1032
Tyr Asn Gly Ile Tyr Tyr Asp Pro Pro Glu Glu Glu Lys Tyr Val Phe
            290                 295                 300 aaa aat cct cag cca aag aga cca aaa tca ctt cgg att tat gag tcg       1080
Lys Asn Pro Gln Pro Lys Arg Pro Lys Ser Leu Arg Ile Tyr Glu Ser
        305                 310                 315 cac gtt gga atg agt agt acg gag cca gta att aac aca tat gcc aac       1128
His Val Gly Met Ser Ser Thr Glu Pro Val Ile Asn Thr Tyr Ala Asn
    320                 325                 330 ttt aga gat gat gtg ctt cct cgc atc aaa aag ctt ggc tac aat gct       1176
Phe Arg Asp Asp Val Leu Pro Arg Ile Lys Lys Leu Gly Tyr Asn Ala
335                 340                 345                 350 gtt cag ctc atg gct att caa gag cat tca tat tat gct agt ttt ggg       1224
Val Gln Leu Met Ala Ile Gln Glu His Ser Tyr Tyr Ala Ser Phe Gly
                355                 360                 365 tat cac gtc aca aac ttt tat gca gct agc agc cga ttt gga act cct       1272
Tyr His Val Thr Asn Phe Tyr Ala Ala Ser Ser Arg Phe Gly Thr Pro
            370                 375                 380 gat gat tta aag tcc cta gta gat aaa gct cac gag tta ggt ctt ctt       1320
Asp Asp Leu Lys Ser Leu Val Asp Lys Ala His Glu Leu Gly Leu Leu
        385                 390                 395 gtt ctc atg gat att gtt cat agc cat gca tca act aat acg ttg gat       1368
Val Leu Met Asp Ile Val His Ser His Ala Ser Thr Asn Thr Leu Asp
    400                 405                 410 ggg ctg aat atg ttt gat ggt acg gat ggt cac tac ttt cac tct gga       1416
Gly Leu Asn Met Phe Asp Gly Thr Asp Gly His Tyr Phe His Ser Gly
415                 420                 425                 430 cca cgg ggt cat cat tgg atg tgg gac tct cgc ctt ttc aac tat ggg       1464
Pro Arg Gly His His Trp Met Trp Asp Ser Arg Leu Phe Asn Tyr Gly
                435                 440                 445 agc tgg gag gtt cta agg ttt ctt ctt tca aat aca agg tgg tgg ttg       1512
Ser Trp Glu Val Leu Arg Phe Leu Leu Ser Asn Thr Arg Trp Trp Leu
            450                 455                 460 gat gag tac aag ttt gat ggg ttc aga ttt gat ggg gtg act tca atg       1560
Asp Glu Tyr Lys Phe Asp Gly Phe Arg Phe Asp Gly Val Thr Ser Met
        465                 470                 475
```

```
atg tac acc cat cat gga ttg cag gta gat ttc acc ggc aac tac aat    1608
Met Tyr Thr His His Gly Leu Gln Val Asp Phe Thr Gly Asn Tyr Asn
    480                 485                 490 gaa tac ttt gga tat gca act gat gta gat gct gtg gtt tat ctg atg    1656
Glu Tyr Phe Gly Tyr Ala Thr Asp Val Asp Ala Val Val Tyr Leu Met
495                 500                 505                 510 ctg ttg aat gat atg att cat ggt ctc ttc cca gag gct gtc acc att    1704
Leu Leu Asn Asp Met Ile His Gly Leu Phe Pro Glu Ala Val Thr Ile
                515                 520                 525 ggt gaa gat gtt agt gga atg cca aca gtt tgc att ccg gtt gaa gat    1752
Gly Glu Asp Val Ser Gly Met Pro Thr Val Cys Ile Pro Val Glu Asp
            530                 535                 540 ggt ggt gtt ggc ttt gat tat cgt ctc cac atg gct gtt gct gat aaa    1800
Gly Gly Val Gly Phe Asp Tyr Arg Leu His Met Ala Val Ala Asp Lys
        545                 550                 555 tgg gtt gag att att cag aag aga gat gaa gat tgg aaa atg ggt gac    1848
Trp Val Glu Ile Ile Gln Lys Arg Asp Glu Asp Trp Lys Met Gly Asp
    560                 565                 570 att gta cat atg ctg acc aac agg cgg tgg ttg gaa aag tgt gtt tct    1896
Ile Val His Met Leu Thr Asn Arg Arg Trp Leu Glu Lys Cys Val Ser
575                 580                 585                 590 tat gct gaa agt cat gac cag gcc ctt gtt ggt gac aaa act att gca    1944
Tyr Ala Glu Ser His Asp Gln Ala Leu Val Gly Asp Lys Thr Ile Ala
                595                 600                 605 ttt tgg ctg atg gac aag gat atg tat gac ttc atg gct cgt gac aga    1992
Phe Trp Leu Met Asp Lys Asp Met Tyr Asp Phe Met Ala Arg Asp Arg
            610                 615                 620 cca tct act cct ctt ata gat cgt gga ata gca ttg cac aaa atg atc    2040
Pro Ser Thr Pro Leu Ile Asp Arg Gly Ile Ala Leu His Lys Met Ile
        625                 630                 635 agg ctt att acc atg ggc tta ggc gga gaa gga tat ttg aat ttt atg    2088
Arg Leu Ile Thr Met Gly Leu Gly Gly Glu Gly Tyr Leu Asn Phe Met
    640                 645                 650 gga aat gaa ttt gga cat cct gag tgg att gat ttt cca aga ggg gat    2136
Gly Asn Glu Phe Gly His Pro Glu Trp Ile Asp Phe Pro Arg Gly Asp
655                 660                 665                 670 cga cat ctg ccc aat ggt aaa gta att cca ggg aac aac cac agt tat    2184
Arg His Leu Pro Asn Gly Lys Val Ile Pro Gly Asn Asn His Ser Tyr
                675                 680                 685 gat aaa tgc cgt cgt aga ttt gat cta ggt gat gca gac tat cta aga    2232
Asp Lys Cys Arg Arg Arg Phe Asp Leu Gly Asp Ala Asp Tyr Leu Arg
            690                 695                 700 tat cat gga atg caa gag ttt gat cag gca atg caa cat ctt gaa gaa    2280
Tyr His Gly Met Gln Glu Phe Asp Gln Ala Met Gln His Leu Glu Glu
        705                 710                 715 gcc tat ggt ttc atg act tct gag cac cag tat ata tca cgg aag gat    2328
Ala Tyr Gly Phe Met Thr Ser Glu His Gln Tyr Ile Ser Arg Lys Asp
    720                 725                 730 gaa gga gat cgg atc att gtc ttt gag agg gga aac ctt gtt ttt gta    2376
Glu Gly Asp Arg Ile Ile Val Phe Glu Arg Gly Asn Leu Val Phe Val
735                 740                 745                 750 ttc aac ttt cat tgg act aac agc tat tca gat tac cga gtt ggc tgc    2424
Phe Asn Phe His Trp Thr Asn Ser Tyr Ser Asp Tyr Arg Val Gly Cys
                755                 760                 765 ttc aag tca gga aag tac aag att gtt ttg gac tcg gat gat ggc ttg    2472
Phe Lys Ser Gly Lys Tyr Lys Ile Val Leu Asp Ser Asp Asp Gly Leu
            770                 775                 780 ttt gga ggc ttc aac agg ctt agt cat gat gcc gag cac ttc acc ttt    2520
Phe Gly Gly Phe Asn Arg Leu Ser His Asp Ala Glu His Phe Thr Phe
        785                 790                 795
```

-continued

```
gac ggg tgg tat gat aac cgg cct cgg tcc ttc atg gta tat gca cca    2568
Asp Gly Trp Tyr Asp Asn Arg Pro Arg Ser Phe Met Val Tyr Ala Pro
800                 805                 810 tct agg aca gca gtg gtc cat gct tta gta gaa gat gaa gag aat gaa    2616
Ser Arg Thr Ala Val Val His Ala Leu Val Glu Asp Glu Glu Asn Glu
815                 820                 825                 830 gca gag aat gaa gta gaa agt gaa gtg aaa cca gcc tcc ggc            2658
Ala Glu Asn Glu Val Glu Ser Glu Val Lys Pro Ala Ser Gly
                835                 840 tgagatagat atttagtaag aggatcccct aaagcaggaa tggttaacct gtgcatctgc  2718
attgaacgac gtatattgag acttgaattg atttgctgct caggacacag aatattaatt  2778
ccaaggctca aggcagagat acacgccata atgcatgatc atatgaaagc tccccaactt  2838
gtaaatcatt tagcaagctg cgtgcactct gtaaattata tgtagtactt tggcaagtca  2898
cgttattatg gataccatgg atgtccgcta ggaaaaattt tgtgtatacg cctactagga  2958
tttttaaatc tcgcatgttc cacataaagt ggtggttgaa tgttgcgcga ctatttttga  3018
gtaaaatgat tgaagttatt cttcacttgg gcctgtgaaa aaaaaaaaa aaaaaa       3074
```

<210> SEQ ID NO 40
<211> LENGTH: 42
<212> TYPE: PRT
<213> ORGANISM: Manihot esculenta

<400> SEQUENCE: 40

```
Met Gln Leu Val Ala Ser Val Leu Thr Leu Ser Leu Thr Ser Gln Arg
1               5                   10                  15

Asn Gly Thr Leu His His Ile Arg Asn Thr Phe Ser Leu Cys Ser Thr
            20                  25                  30

Pro Gln Ile Ser Ile Tyr Arg Leu Pro Trp
        35                  40
```

<210> SEQ ID NO 41
<211> LENGTH: 2223
<212> TYPE: DNA
<213> ORGANISM: Manihot esculenta

<400> SEQUENCE: 41

```
ttagttgcgt cagttctcac actctctcta acttctcagc gaaatgggac actacaccat    60
atcaggaata cgttttcctt gtgctccact ccgcaaatct caatctaccg gcttccatgg   120
tgatcgaagg acctcctctt gcctttcctt caacttcaag aaggcggcgt tttctaggag   180
ggtcttctct ggaaagtcat ctcatgaatc tgactcctca aatgtaatgg tcactgcgtc   240
taaaagagtc cttcctgatg gtcggattga atgctattcc tcttcaacag atcaattgga   300
agcccctggc acagtttcag aagaatccca ggtgcttact gatgttgaga gtctcattat   360
ggatgataag attgttgaag atgaagtaaa taagaatctg gttccaatgc gggagacagt   420
tagcatcgga aaaattggat ctaaaccaag gtccattcct ccacccggca gagggcaaag   480
aatatatgac atagatccaa gcttgacagg ctttcgtcaa cacctagatt accggtattc   540
acagtacaaa agactccgag aagaaattga caagtatgaa ggtagtctgg atgcattttc   600
tcgtggctat gaaaagtttg gtttctcacg cagtgaaaca ggaataactt atagagagtg   660
ggcaccagga gctacgtggg ctgcattgat tggagatttc aataactgga atcctaatgc   720
agatgtcatg actcagaatg agtgtggtgt ctggagagatc ttttttgccga ataatgcaga   780 tggttcacca ccaattcccc atggttctcg agtaaagata cgcatggata ctccatctgg   840
```

-continued

```
caacaaagat tctattcctg cttggatcaa gttctcagtt caagcaccag gtgaactccc      900
atataatggc atatactatg atcctcccga ggaggagaag tatgtgttca aaaatcctca      960
gccaaagaga ccaaaatcac ttcggattta tgagtcgcac gttggaatga gtagtacgga     1020
gccagtaatt aacacatatg ccaactttag agatgatgtg cttcctcgca tcaaaaagct     1080
tggctacaat gctgttcagc tcatggctat tcaagagcat tcatattatg ctagttttgg     1140
gtatcacgtc acaaactttt atgcagctag cagccgattt ggaactcctg atgatttaaa     1200
gtccctagta gataaagctc acgagttagg tcttcttgtt ctcatggata ttgttcatag     1260
ccatgcatca actaatacgt tggatgggct gaatatgttt gatggtacgg atggtcacta     1320
ctttcactct ggaccacggg tcatcattg gatgtgggac tctcgccttt tcaactatgg     1380
gagctgggag gttctaaggt ttcttctttc aaatacaagg tggtggttgg atgagtacaa     1440
gtttgatggg ttcagatttg atggggtgac ttcaatgatg tacacccatc atggattgca     1500
ggtagatttc accggcaact acaatgaata ctttggatat gcaactgatg tagatgctgt     1560
ggtttatctg atgctgttga atgatatgat tcatggtctc ttcccagagg ctgtcaccat     1620
tggtgaagat gttagtggaa tgccaacagt ttgcattccg gttaagatg gtggtgttgg     1680
ctttgattat cgtctccaca tggctgtttgc tgataaatgg gttgagatta ttcagaagag     1740
agatgaagat tggaaaatgg gtgacattgt acatatgctg accaacaggc ggtggttgga     1800
aaagtgtgtt tcttatgctg aaagtcatga ccaggcccct tgttggtgaca aaactattgc     1860
attttggctg atggacaagg atatgtatga cttcatggct cgtgacagac catctactcc     1920
tcttatagat cgtggaatag cattgcacaa aatgatcagg cttattacca tgggcttagg     1980
cggagaagga tatttgaatt ttatgggaaa tgaattggga catcctgagt ggattgattt     2040
tccaagaggg gatcgacatc tgcccaatgg taaagtaatt ccagggaaca accacagtta     2100
tgataaatgc cgtcgtagat ttgatctagg tgatgcagac tatctaagat atcatggaat     2160
gcaagagttt gatcaggcaa tgcaacatct tgaagaagcc tatggtttca tgacttctga     2220
gca                                                                    2223
```

<210> SEQ ID NO 42
<211> LENGTH: 2224
<212> TYPE: DNA
<213> ORGANISM: Manihot esculenta

<400> SEQUENCE: 42

```
ttagttgcgt cagttctcac actctctcta acttctcagc gaaatgggac actacaccat       60
atcaggaata cgttttcctt gtgctccact atgcaaatct caatctaccg gcttccatgg      120
cgatcggagg acctcctctt gcctttcctt caacttcaag aaggaggcgt tttctaggag      180
ggtcttctct ggaaagtcat ctcatgaatc tgactcctca aatgtaatgg tcactgcgtc      240
taaagagtc cttcctgatg gtcggattga atgctattct tcttcaacag atcaattgga      300
agcccctggc acagtttcag aagaatccca ggtgcttact gatgttgaga gtctcattat      360
ggatgataag attgttgaag atgaagtaaa taaagaatct gttccaatgc gggagacagt      420
tagcatcaga aaaattggat ctaaaccaag gtccattcct ccacccggca gagggcaaag      480
aatatatgac atagatccaa gcttgacagg ctttcgtcaa cacctagatt accggtattc      540
acagtacaaa agactccgag aagaaattga caagtatgaa ggtggtctgg atgcattttc      600
tcgtggctat gaaaagtttg gtttctcacg cagtgaaaca ggataacctt atagagagtg      660
```

```
ggcaccagga gctacgtggg ctgcattgat tggagatttc aataactgga atcctaatgc      720
agatgtcatg actcagaatg agtgtggcgt ctgggagatc tttttgccga ataatgcaga      780
tggttcacca ccaattcccc atggttctcg agtaaagata tgcatggata ctccatctgg      840
caacaaagat tctattcctg cttggatcaa gttctcagtt caagcaccag gtgaactccc      900
atataatggc atatactatg atcctcccga ggaggagaag tatgtgttca aaaatcctca      960
gccaaagaga ccaaaatcac ttcggattta tgagtcgcac gttggaatga gtagtacgga     1020
gccagtaatt aacacatatg ccaactttag agatgatgtg cttcctcgca tcaaaaagct     1080
tggctacaat gctgttcagc tcatggctat tcaagagcat tcatattatg ctagttttgg     1140
gtatcacgtc acaaactttt atgcagctag cagccgattt ggaactcctg atgatttaaa     1200
gtctctaata gataaagctc acgagttagg tcttcttgtt ctcatggata ttgttcatag     1260
ccatgcatca actaatacgt tggatgggct gaatatgttt gatggtacgg atggtcacta     1320
cttttcactct ggaccacggg gtcatcattg gatgtgggac tctcgccttt tcaactatgg     1380
gagctgggag gttctaaggt ttcttctttc aaatgcaagg tggtggttgg atgagtacaa     1440
gtttgatggg ttcagatttg atggggtgac ttcaatgatg tacacccatc atggattgca     1500
ggtagatttt accggcaact acaatgaata ctttggatat gcaactgatg tagatgctgt     1560
ggtttatttg atgctgttga atgatatgat tcatggtctc ttcccagagg ctgtcaccat     1620
tggtgaagat gttagtggaa tgccaacagt ttgcattccg gttgaagatg gtggtgttgg     1680
cttttgattat cgtctccaca tggctgttgc tgataaatgg gttgagatta ttcagaagag     1740
agatgaagat tggaaaatgg gtgacattgt acatatgctg accaacaggc ggtggttgga     1800
aaagtgtgtt tcttatgctg aaagtcatga ccaggcccctt gttggtgaca aaactattgc     1860
attttggctg atggacaagg atatgtatga cttcatggct cttgacagac catctactcc     1920
tctcatagat cgtggagtag cattgcacaa aatgatcagg cttattacca tgggattagg     1980
cggagaagga tatttgaatt ttatgggaaa tgaatttgga caccccgagt ggattgattt     2040
tccaagaggt gatctacatc ttcccagtgg taaatttgtt cctgggaaca attacagtta     2100
tgataaatgc cggcgtaggt ttgatctagg caattcaaag cgtctgagat atcatggaat     2160
gcaagagttt gatcaagcaa ttcagcatct tgaagaagcc tatggtttca tgacttctga     2220
gcaa                                                                  2224
```

<210> SEQ ID NO 43
<211> LENGTH: 2223
<212> TYPE: DNA
<213> ORGANISM: Manihot esculenta

<400> SEQUENCE: 43

```
ttagttgcgt cagttctcac actctctcta acttctcagc gaaatgggac actacaccat       60
atcaggaata cgttttcctt gtgctccact ctgcaaatct caatctaccg gcttccatgg      120
tgatcgaagg acctcctctt gcctttcctt caacttcaag aaggcggcgt tttctaggag      180
ggtcttctct agaaagtcat ctcatgaatc tgactcctca aatgtaatgg tcactgcgtc      240
taaaagagtc cttcctgatg gtcggattga atgctattct tcttcaacag atcaattgga      300
agcccctggc acagtttcag aagaatccca ggtgcttact gatgttgaga gtctcattat      360
ggatgataag attgttgaag atgaagtaaa taagaatct gttccaatgc gggagacagt      420
tagcatcaga aaaattggat ctaaaccaag gtccattcct ccacccggca gagggcaaag      480
aatatatgac atagatccaa gcttgacagg cttttcgtcaa cacctagatt accggtattc      540
```

```
acagtacaaa agactccgag aagaaattga caagtatgaa ggtagtctgg atgcattttc      600
tcgtggctat gaaaagtttg gtttctcacg cagtgaaaca ggaataactt atagagagtg      660
ggcaccagga gctacgtggg ctgcattgat tggagatttc aataactgga atcctaatgc      720
agatgtcatg actcagaatg agtgtggtgt ctgggagatc ttttgccga ataatgcaga       780
tggttcacca ccaattcccc atggttctcg agtaaagata cgcatggata ctccatctgg      840
caacaaagat tctattcctg cttggatcaa gttcccagtt caagcaccag gtgaactccc      900
atataatggc atatactatg atcctcccga ggaggagaag tatgtgttca aaaatcctca      960
gccaaagaga ccaaaatcac ttcggattta tgagtcgcac gttggaatga gtagtacgga     1020
gccagtaatt aacacatatg ccaactttag agatgatgtg cttcctcgca tcaaaaagct     1080
tggctacaat gctgttcagc tcatggctat tcaagagcat tcatattatg ctagttttgg     1140
gtatcacgtc acaaactttt atgcagctag cagccgattt ggaactcctg atgatttaaa     1200
gtctctaata gataaagctc acgagttagg tcttcttgtt cttatggata ttgttcatag     1260
ccatgcatca actaatacgt tggatgggct gaatatgttt gatggtacgg atggtcacta     1320
cttttcactct ggactacggg gtcatcattg gatgtgggac tctcgccttt tcaaccatgg     1380
gagctgggag gttctaaggt ttcttctttc aaatgcaagg tggtggtgg atgagtacaa     1440
gtttgatggg ttcagatttg atgggtgac ttcaatgatg tacacccatc atggattgca       1500
ggtagatttt accggcaact acaatgaata ctttggatat gcaactgatg tagatgctgt     1560
ggtttatttg atgctgttga atgatatgat tcatggtctc ttcccagagg ctgtcaccat     1620
tggtgaagat gttagtggaa tgccaacagt ttgcattccg gttgaagatg gtggtgttgg     1680
cttttgattat cgtctccaca tggctgttgc tgataaatgg gttgagatta ttcagaagag     1740
agatgaagat tggaaaatgg gtgacattgt acatatgctg accaacaggc ggtggttgga     1800
aaagtgtgtt tcttatgctg aaagtcatga ccaggccctt gttggtgaca aaactattgc     1860
attttggctg atggacaagg atatgtatga cttcatggct cgtgacagac catctacccc     1920
tcttatagat cgtggagtag cattgcacaa aatgatcagg cttattacca tgggattagg     1980
cggagaagga tatttgaatt ttatgggaaa tgaatttgga caccccgagt ggattgattt     2040
tccaagaggt gatctacatc ttcccagtgg taaatttgtt cctgggaaca attacagtta     2100
tgataaatgc cggcgtaggt ttgatctagg caattcaaag catctgagat atcatggaat     2160
gcaagagttt gatcaagcaa ttcagcatct tgaagaagcc tatggtttca tgacttctga     2220
gca                                                                    2223

<210> SEQ ID NO 44
<211> LENGTH: 1394
<212> TYPE: DNA
<213> ORGANISM: Manihot esculenta

<400> SEQUENCE: 44 tagtttggg tatcacgtca caaactttta tgcagctagc agccgatttg gaactcctga       60
tgatttaaag tctctaatag ataaagctca cgagttaggt cttcttgttc tcatggatat     120
tgttcatagc catgcatcaa ctaatacgtt ggatgggctg aaatatgttt gatggtacgg     180
atggtcacta cttttcactct ggaccacggg tcatcattgg atgtgggact cccgcctttt    240
caactatggg agctgggagg ttctaaggtt tcttctttca aatgcaaggt ggtggttgga     300
tgagtacaag tttgatgggt tcagatttga tggggtgact tcaatgatgt acacccatca     360
```

-continued

```
tggattgcag gtagctttta ccggcaacta caatgaatac tttggatatg caactgatgt        420
agatgctgtg gtttatttga tgctgttgaa tgatatgatt catggtctct tcccagaggc        480
tgtcaccatt ggtgaagatg ttagtggaat gccaacagtt tgcattccgg ttgaagatgg        540
tggtgttggc tttgattatc gtctccacat ggctgttgct gataaatggg ttgagattat        600
tcagaagaga gatgaagatt ggaaaatggg tgacattgta catatgctga ccaacaggcg        660
gtggttggaa aagtgtgttt cttatgctga aagtcatgac caggcccttg ttggtgacaa        720
aactattgca ttttggctga tggacaagga tatgtatgac ttcatggctc ttgacagacc        780
atctacccct ctcatagatc gtggagtagc attgcacaaa atgatcaggc ttattaccat        840
gggattaggc ggagaaggat atttgaattt tatgggaaat gaatttggac accccgagtg        900
gattgatttt ccaagaggtg atctacatct tcccagtggt aaatttgttc ctgggaacaa        960
ttacagttat gataaatgcc ggcgtaggtt tgatctaggc aatgcaaagc atctgagata       1020
tcatggaatg caagagtttg atcaagcaat tcagcatctt gaagaagcct atggtttcat       1080
gacttctgag caccaataca tatcacggaa ggatgaaagg gatcggatca ttgtcttcga       1140
gaggggaaac ctcgtttttg tattcaattt tcattggact agcagctatt cggattaccg       1200
agttggctgc ttaaagccag gaaagtacaa gatagtcttg gattcagatg atcctttgtt       1260
tggaggcttt ggcaggctta gtcatgatgc agagcacttc agctttgaag ggtggtacga       1320
taaccggcct cggtccttca tggtatatgc accatctagg acagcagtgg tccatgcttt       1380
agtagaagat gaag                                                          1394
```

<210> SEQ ID NO 45
<211> LENGTH: 1394
<212> TYPE: DNA
<213> ORGANISM: Manihot esculenta

<400> SEQUENCE: 45

```
tagttttggg taccatgtca caaacttttt tgcacctagc agccgatttg gaactcctga         60
tgatttgaag tctttaatag ataaagctca tgagttaggg ctgcttgttc tcatggatat        120
tgttcatagc catgcgtcaa ataatacgtt ggatgggctg aacatgtttg atggtacgga        180
tagtcactac ttccactccg gatcacgggg tcatcattgg ttgtgggact ctcgccttt         240 caactatgga agctgggagg tgctaagatt tcttctttca aatgcaagat ggtggttgga        300
agagtacagg tttgatggtt ttagatttga tggggtgact tccatgatgt acactcccca        360
tgggttgcag gtagctttta ctggcaacta caatgagtac tttggatatg caactgatgt        420
agatgctgtg atttatttga tgcttgtgaa tgatatgatt cacggtcttt tccctgaggc        480
tgttaccatt ggtgaagatg ttagcggaaa gccaacattt tgcattccag tggaagatgg        540
tggtgttgga tttgattacc gtctccacat ggccattgcc gataaatgga ttgagattct        600
taagaagaga gatgaggact ggaaaatggg tgacattgtg catacactca ccaacagaag        660
gtggttggaa aaatgtgttg cttatgctga aagtcatgac caagctcttg ttggtgacaa        720
aactattgca ttttggctga tggacaagga catgtacgac ttcatggctc gtgacagacc        780
atctactcct cttatagatc gtggaatagc attgcacaaa atgatcaggc ttattaccat        840
gggcttaggc ggagaaggat atttgaattt tatgggaaat gaatttggac atcctgagtg        900
gattgatttt ccaagagggg atcgacatct gcccaatggt aaagtaattc caggaacaa         960 ccacagttat gataaatgcc gtcgtagatt tgatctaggt gatgcagact atctaagata       1020
tcatggaatg caagagtttg atcaggcaat gcaacatctt gaagaagcct atggtttcat       1080
```

```
gacttctgag caccagtata tatcacggaa ggatgaagga gatcggatca ttgtctttga   1140
gaggggaaac cttgttttg tattcaactt tcattggact aacagctatt cagattaccg   1200
agttggctgc ttcaagtcag gaaagtacaa gattgttttg gactcggatg atggcttgtt   1260
tggaggcttc aacaggctta gtcatgatgc cgagcacttc acctttgacg ggtggtatga   1320
taaccggcct cggtccttca tggtatatgc accatctagg acagcagtgg tccatgcttt   1380
agtagaagat gaag                                                     1394
```

<210> SEQ ID NO 46
<211> LENGTH: 474
<212> TYPE: PRT
<213> ORGANISM: Manihot esculenta

<400> SEQUENCE: 46

```
Ser Phe Gly Tyr His Val Thr Asn Phe Tyr Ala Ala Ser Ser Arg Phe
  1               5                  10                  15

Gly Thr Pro Asp Asp Leu Lys Ser Leu Ile Asp Lys Ala His Glu Leu
             20                  25                  30

Gly Leu Leu Val Leu Met Asp Ile Val His Ser His Ala Ser Asn Thr
         35                  40                  45

Thr Leu Asp Gly Leu Asn Met Phe Asp Gly Thr Asp Pro His Tyr Phe
     50                  55                  60

His Ser Gly Ser Arg Gly His His Trp Met Trp Asp Ser Arg Leu Phe
 65                  70                  75                  80

Asn Tyr Gly Ser Trp Glu Val Leu Arg Phe Leu Leu Ser Asn Ala Arg
                 85                  90                  95

Trp Trp Leu Asp Glu Tyr Lys Phe Asp Gly Phe Arg Phe Asp Gly Val
            100                 105                 110

Thr Ser Met Met Tyr Thr His His Gly Leu Gln Val Asp Phe Thr Gly
        115                 120                 125

Asn Tyr Asn Glu Tyr Phe Gly Tyr Ala Thr Asp Val Asp Ala Val Val
    130                 135                 140

Tyr Leu Met Leu Leu Asn Asp Met Ile His Gly Leu Phe Pro Glu Ala
145                 150                 155                 160

Val Thr Ile Gly Glu Asp Val Ser Gly Met Pro Thr Val Cys Ile Pro
                165                 170                 175

Val Glu Asp Gly Gly Val Gly Phe Asp Tyr Arg Leu His Met Ala Val
            180                 185                 190

Ala Asp Lys Trp Val Glu Ile Ile Gln Lys Arg Asp Glu Asp Trp Lys
        195                 200                 205

Met Gly Asp Ile Val His Met Leu Thr Asn Arg Arg Trp Leu Glu Lys
    210                 215                 220

Cys Val Ser Tyr Ala Glu Ser His Asp Gln Ala Leu Val Gly Asp Lys
225                 230                 235                 240

Thr Ile Ala Phe Trp Leu Met Asp Lys Asp Met Tyr Asp Phe Met Ala
                245                 250                 255

Leu Asp Arg Pro Ser Thr Pro Leu Ile Asp Arg Gly Val Ala Leu His
            260                 265                 270

Lys Met Ile Arg Leu Ile Thr Met Gly Leu Gly Gly Glu Gly Tyr Leu
        275                 280                 285

Asn Phe Met Gly Asn Glu Phe Gly His Pro Glu Trp Ile Asp Phe Pro
    290                 295                 300

Arg Gly Asp Leu His Leu Pro Ser Gly Lys Phe Val Pro Gly Asn Asn
```

-continued

```
                305                 310                 315                 320
Tyr Ser Tyr Asp Lys Cys Arg Arg Phe Asp Leu Gly Asp Asn Ser
                    325                 330                 335

Lys His Arg Tyr His Gly Met Gln Glu Phe Asp Gln Ala Ile Gln His
                340                 345                 350

Leu Glu Glu Ala Tyr Gly Phe Met Thr Ser Glu His Gln Tyr Ile Ser
                355                 360                 365

Arg Lys Asp Glu Gly Asp Arg Ile Ile Val Phe Glu Arg Gly Asn Leu
            370                 375                 380

Val Phe Val Phe Asn Phe His Trp Thr Ser Ser Tyr Ser Asp Tyr Arg
385                 390                 395                 400

Val Gly Cys Leu Lys Ser Gly Lys Tyr Lys Ile Val Leu Asp Ser Asp
                    405                 410                 415

Asp Pro Leu Phe Gly Gly Phe Gly Arg Leu Ser His Asp Ala Glu His
                420                 425                 430

Phe Ser Phe Glu Gly Trp Tyr Asp Asn Arg Pro Arg Ser Phe Met Val
            435                 440                 445

Tyr Thr Pro Cys Arg Thr Ala Val Val Tyr Ala Leu Val Glu Asp Glu
450                 455                 460

Val Glu Asn Glu Val Glu Pro Val Ala Gly
465                 470

<210> SEQ ID NO 47
<211> LENGTH: 474
<212> TYPE: PRT
<213> ORGANISM: Manihot esculenta

<400> SEQUENCE: 47

Ser Phe Gly Tyr His Val Thr Asn Phe Phe Ala Pro Ser Ser Arg Phe
  1               5                  10                  15

Gly Thr Pro Asp Asp Leu Lys Ser Leu Ile Asp Lys Ala His Glu Leu
                 20                  25                  30

Gly Leu Leu Val Leu Met Asp Ile Val His Ser His Ala Ser Asn Asn
             35                  40                  45

Thr Leu Asp Gly Leu Asn Met Phe Asp Gly Thr Asp Ser His Tyr Phe
         50                  55                  60

His Ser Gly Ser Arg Gly His His Trp Leu Trp Asp Ser Arg Leu Phe
 65                  70                  75                  80

Asn Tyr Gly Ser Trp Glu Val Leu Arg Phe Leu Leu Ser Asn Ala Arg
                 85                  90                  95

Trp Trp Leu Glu Glu Tyr Arg Phe Asp Gly Phe Arg Phe Asp Gly Val
            100                 105                 110

Thr Ser Met Met Tyr Thr Pro His Gly Leu Gln Val Ala Phe Thr Gly
        115                 120                 125

Asn Tyr Asn Glu Tyr Phe Gly Tyr Ala Thr Asp Val Asp Ala Val Ile
    130                 135                 140

Tyr Leu Met Leu Val Asn Asp Met Ile His Gly Leu Phe Pro Glu Ala
145                 150                 155                 160

Val Thr Ile Gly Glu Asp Val Ser Gly Lys Pro Thr Phe Cys Ile Pro
                165                 170                 175

Val Glu Asp Gly Gly Val Gly Phe Asp Tyr Arg Leu His Met Ala Ile
            180                 185                 190

Ala Asp Lys Trp Ile Glu Ile Leu Lys Lys Arg Asp Glu Asp Trp Lys
        195                 200                 205
```

```
Met Gly Asp Ile Val His Thr Leu Thr Asn Arg Arg Trp Leu Glu Lys
210                 215                 220
Cys Val Ala Tyr Ala Glu Ser His Asp Gln Ala Leu Val Gly Asp Lys
225                 230                 235                 240
Thr Ile Ala Phe Trp Leu Met Asp Lys Asp Met Tyr Asp Phe Met Ala
                245                 250                 255
Arg Asp Arg Pro Ser Thr Pro Leu Ile Asp Arg Gly Ile Ala Leu His
                260                 265                 270
Lys Met Ile Arg Leu Ile Thr Met Gly Leu Gly Gly Glu Gly Tyr Leu
            275                 280                 285
Asn Phe Met Gly Asn Glu Phe Gly His Pro Glu Trp Ile Asp Phe Pro
290                 295                 300
Arg Gly Asp Arg His Leu Pro Asn Gly Lys Val Ile Pro Gly Asn Asn
305                 310                 315                 320
His Ser Tyr Asp Lys Cys Arg Arg Phe Asp Leu Gly Asp Ala Asp
                325                 330                 335
Tyr Leu Arg Tyr His Gly Met Gln Glu Phe Asp Gln Ala Met Gln His
                340                 345                 350
Leu Glu Ala Tyr Gly Phe Met Thr Ser His Gln Tyr Ile Ser
            355                 360                 365
Arg Lys Asp Glu Gly Asp Arg Ile Ile Val Phe Glu Arg Gly Asn Leu
370                 375                 380
Val Phe Val Phe Asn Phe His Trp Thr Asn Ser Tyr Ser Asp Tyr Arg
385                 390                 395                 400
Val Gly Cys Phe Lys Ser Gly Lys Tyr Lys Ile Val Leu Asp Ser Asp
                405                 410                 415
Asp Gly Leu Phe Gly Phe Asn Arg Leu Ser His Asp Ala Glu His
            420                 425                 430
Phe Thr Phe Asp Gly Trp Tyr Asp Asn Arg Pro Arg Ser Phe Met Val
                435                 440                 445
Tyr Ala Pro Ser Arg Thr Ala Val Val His Ala Leu Val Glu Asp Glu
            450                 455                 460
Glu Asn Glu Ala Glu Asn Glu Val Glu Ser
465                 470

<210> SEQ ID NO 48
<211> LENGTH: 1069
<212> TYPE: DNA
<213> ORGANISM: Manihot esculenta
<220> FEATURE:
<221> NAME/KEY: CDS
<222> LOCATION: (1)..(684)

<400> SEQUENCE: 48 atg gac aag gat atg tat gac ttc atg gct ctt gac aga cca tct act      48
Met Asp Lys Asp Met Tyr Asp Phe Met Ala Leu Asp Arg Pro Ser Thr
1               5                   10                  15 cct ctc ata gat cgt gga gta gca ttg cac aaa atg atc agg ctt att     96
Pro Leu Ile Asp Arg Gly Val Ala Leu His Lys Met Ile Arg Leu Ile
            20                  25                  30 acc atg gga tta ggc gga gaa gga tat ttg aat ttt atg gga aat gaa    144
Thr Met Gly Leu Gly Gly Glu Gly Tyr Leu Asn Phe Met Gly Asn Glu
        35                  40                  45 ttt gga cac ccc gag tgg att gat ttt cca aga ggt gat cta cat ctt    192
Phe Gly His Pro Glu Trp Ile Asp Phe Pro Arg Gly Asp Leu His Leu
    50                  55                  60 ccc agt ggt aaa ttt gtt cct ggg aac aat tac agt tat gat aaa tgc    240
```

```
Pro Ser Gly Lys Phe Val Pro Gly Asn Asn Tyr Ser Tyr Asp Lys Cys
 65                  70                  75                  80 cgg cgt agg ttt gat cta ggc aat tca aag cgt ctg aga tat cat gga       288
Arg Arg Arg Phe Asp Leu Gly Asn Ser Lys Arg Leu Arg Tyr His Gly
                 85                  90                  95 atg caa gag ttt gat caa gca att cag cat ctt gaa gaa gcc tat ggt       336
Met Gln Glu Phe Asp Gln Ala Ile Gln His Leu Glu Glu Ala Tyr Gly
            100                 105                 110 ttc atg act tct gag cac caa tac ata tca cgg aag gat gaa agg gat       384
Phe Met Thr Ser Glu His Gln Tyr Ile Ser Arg Lys Asp Glu Arg Asp
        115                 120                 125 cgg atc att gtc ttc gag agg gga aac ctc gtt ttt gta ttc aat ttt       432
Arg Ile Ile Val Phe Glu Arg Gly Asn Leu Val Phe Val Phe Asn Phe
    130                 135                 140 cat tgg act agc agc tat tcg gat tac cga gtt ggc tgc tta aag cca       480
His Trp Thr Ser Ser Tyr Ser Asp Tyr Arg Val Gly Cys Leu Lys Pro
145                 150                 155                 160 gga aag tac aag ata gtc ttg gat tca gat gat cct ttg ttt gga ggc       528
Gly Lys Tyr Lys Ile Val Leu Asp Ser Asp Asp Pro Leu Phe Gly Gly
                165                 170                 175 ttt ggc agg ctt agt cat gat gca gag cac ttc agc ttt gaa ggg tgg       576
Phe Gly Arg Leu Ser His Asp Ala Glu His Phe Ser Phe Glu Gly Trp
            180                 185                 190 tac gat aac cgg cct cga tcc ttc atg gtg tac aca cca tgt aga aca       624
Tyr Asp Asn Arg Pro Arg Ser Phe Met Val Tyr Thr Pro Cys Arg Thr
        195                 200                 205 gca gtg gtc tat gct tta gtg gag gat gaa gtg gag aat gaa gtg gaa       672
Ala Val Val Tyr Ala Leu Val Glu Asp Glu Val Glu Asn Glu Val Glu
    210                 215                 220 cct gtc gcc ggt taagatatat cttagcaaca ggttctgaag caggaatgcc          724
Pro Val Ala Gly
225 attattgatc ttcctatgtg catctgcgtt gaacgaaata tattgagcct ataatttgat     784 gtcacggtcc ttgcagattt ccatcctggt tcttggtatt tgttgtcat gataaacata      844 atcaaagacc aataggaaac gcaggggttac atgctagctt ccatcatcat agggagctca    904 gacctcctaa accataaatc ttcaagctgc ctgcgttcgg tagtatgtta tgtggtactt     964 tgcaatctta aattatcatg atcgctgtgg atgctaacta tgacaatttt gtatatatgc    1024 caacgaggat tttaagtttt aaaaaaaaaa caaaaaaaat ccatg                    1069
```

<210> SEQ ID NO 49
<211> LENGTH: 228
<212> TYPE: PRT
<213> ORGANISM: Manihot esculenta

<400> SEQUENCE: 49

```
Met Asp Lys Asp Met Tyr Asp Phe Met Ala Leu Asp Arg Pro Ser Thr
  1               5                  10                  15

Pro Leu Ile Asp Arg Gly Val Ala Leu His Lys Met Ile Arg Leu Ile
             20                  25                  30

Thr Met Gly Leu Gly Gly Glu Gly Tyr Leu Asn Phe Met Gly Asn Glu
         35                  40                  45

Phe Gly His Pro Glu Trp Ile Asp Phe Pro Arg Gly Asp Leu His Leu
     50                  55                  60

Pro Ser Gly Lys Phe Val Pro Gly Asn Asn Tyr Ser Tyr Asp Lys Cys
 65                  70                  75                  80

Arg Arg Arg Phe Asp Leu Gly Asn Ser Lys Arg Leu Arg Tyr His Gly
```

```
                    85                  90                  95
Met Gln Glu Phe Asp Gln Ala Ile Gln His Leu Glu Ala Tyr Gly
            100                 105                 110

Phe Met Thr Ser Glu His Gln Tyr Ile Ser Arg Lys Asp Glu Arg Asp
            115                 120                 125

Arg Ile Ile Val Phe Glu Arg Gly Asn Leu Val Phe Val Asn Phe
        130                 135                 140

His Trp Thr Ser Ser Tyr Ser Asp Tyr Arg Val Gly Cys Leu Lys Pro
145                 150                 155                 160

Gly Lys Tyr Lys Ile Val Leu Asp Ser Asp Pro Leu Phe Gly Gly
            165                 170                 175

Phe Gly Arg Leu Ser His Asp Ala Glu His Phe Ser Phe Glu Gly Trp
            180                 185                 190

Tyr Asp Asn Arg Pro Arg Ser Phe Met Val Tyr Thr Pro Cys Arg Thr
        195                 200                 205

Ala Val Val Tyr Ala Leu Val Glu Asp Glu Val Glu Asn Glu Val Glu
    210                 215                 220

Pro Val Ala Gly
225

<210> SEQ ID NO 50
<211> LENGTH: 1921
<212> TYPE: DNA
<213> ORGANISM: Manihot esculenta
<220> FEATURE:
<221> NAME/KEY: CDS
<222> LOCATION: (61)..(1503)

<400> SEQUENCE: 50
tatggattga catcgataat acgactcact atagggattt tttttttttt tttttttgt      60 agt ttt ggg tac cat gtc aca aac ttt ttt gca cct agc agc cga ttt     108
Ser Phe Gly Tyr His Val Thr Asn Phe Phe Ala Pro Ser Ser Arg Phe
  1               5                  10                  15 gga act cct gat gat ttg aag tct tta ata gat aaa gct cat gag tta     156
Gly Thr Pro Asp Asp Leu Lys Ser Leu Ile Asp Lys Ala His Glu Leu
                 20                  25                  30 ggg ctg ctt gtt ctc atg gat att gtt cat agc cat gcg tca aat aat     204
Gly Leu Leu Val Leu Met Asp Ile Val His Ser His Ala Ser Asn Asn
             35                  40                  45 acg ttg gat ggg ctg aac atg ttt gat ggt acg gat agt cac tac ttc     252
Thr Leu Asp Gly Leu Asn Met Phe Asp Gly Thr Asp Ser His Tyr Phe
         50                  55                  60 cac tcc gga tca cgg ggt cat cat tgg ttg tgg gac tct cgc ctt ttc     300
His Ser Gly Ser Arg Gly His His Trp Leu Trp Asp Ser Arg Leu Phe
     65                  70                  75                  80 aac tat gga agc tgg gag gtg cta aga ttt ctt ctt tca aat gca aga     348
Asn Tyr Gly Ser Trp Glu Val Leu Arg Phe Leu Leu Ser Asn Ala Arg
                 85                  90                  95 tgg tgg ttg gaa gag tac agg ttt gat ggt ttt aga ttt gat ggg gtg     396
Trp Trp Leu Glu Glu Tyr Arg Phe Asp Gly Phe Arg Phe Asp Gly Val
            100                 105                 110 act tcc atg atg tac act ccc cat ggg ttg cag gta gct ttt act ggc     444
Thr Ser Met Met Tyr Thr Pro His Gly Leu Gln Val Ala Phe Thr Gly
            115                 120                 125 aac tac aat gag tac ttt gga tat gca act gat gta gat gct gtg att     492
Asn Tyr Asn Glu Tyr Phe Gly Tyr Ala Thr Asp Val Asp Ala Val Ile
        130                 135                 140 tat ttg atg ctt gtg aat gat atg att cac ggt ctt ttc cct gag gct     540
```

```
Tyr Leu Met Leu Val Asn Asp Met Ile His Gly Leu Phe Pro Glu Ala
145                 150                 155                 160 gtt acc att ggt gaa gat gtt agc gga aag cca aca ttt tgc att cca    588
Val Thr Ile Gly Glu Asp Val Ser Gly Lys Pro Thr Phe Cys Ile Pro
                165                 170                 175 gtg gaa gat ggt ggt gtt gga ttt gat tac cgt ctc cac atg gcc att    636
Val Glu Asp Gly Gly Val Gly Phe Asp Tyr Arg Leu His Met Ala Ile
            180                 185                 190 gcc gat aaa tgg att gag att ctt aag aag aga gat gag gac tgg aaa    684
Ala Asp Lys Trp Ile Glu Ile Leu Lys Lys Arg Asp Glu Asp Trp Lys
        195                 200                 205 atg ggt gac att gtg cat aca ctc acc aac aga agg tgg ttg gaa aaa    732
Met Gly Asp Ile Val His Thr Leu Thr Asn Arg Arg Trp Leu Glu Lys
    210                 215                 220 tgt gtt gct tat gct gaa agt cat gac caa gct ctt gtt ggt gac aaa    780
Cys Val Ala Tyr Ala Glu Ser His Asp Gln Ala Leu Val Gly Asp Lys
225                 230                 235                 240 act att gca ttt tgg ctg atg gac aag gac atg tac gac ttc atg gct    828
Thr Ile Ala Phe Trp Leu Met Asp Lys Asp Met Tyr Asp Phe Met Ala
                245                 250                 255 cgt gac aga cca tct act cct ctt ata gat cgt gga ata gca ttg cac    876
Arg Asp Arg Pro Ser Thr Pro Leu Ile Asp Arg Gly Ile Ala Leu His
            260                 265                 270 aaa atg atc agg ctt att acc atg ggc tta ggc gga gaa gga tat ttg    924
Lys Met Ile Arg Leu Ile Thr Met Gly Leu Gly Gly Glu Gly Tyr Leu
        275                 280                 285 aat ttt atg gga aat gaa ttt gga cat cct gag tgg att gat ttt cca    972
Asn Phe Met Gly Asn Glu Phe Gly His Pro Glu Trp Ile Asp Phe Pro
    290                 295                 300 aga ggg gat cga cat ctg ccc aat ggt aaa gta att cca ggg aac aac   1020
Arg Gly Asp Arg His Leu Pro Asn Gly Lys Val Ile Pro Gly Asn Asn
305                 310                 315                 320 cac agt tat gat aaa tgc cgt cgt aga ttt gat cta ggt gat gca gac   1068
His Ser Tyr Asp Lys Cys Arg Arg Arg Phe Asp Leu Gly Asp Ala Asp
                325                 330                 335 tat cta aga tat cat gga atg caa gag ttt gat cag gca atg caa cat   1116
Tyr Leu Arg Tyr His Gly Met Gln Glu Phe Asp Gln Ala Met Gln His
            340                 345                 350 ctt gaa gaa gcc tat ggt ttc atg act tct gag cac cag tat ata tca   1164
Leu Glu Glu Ala Tyr Gly Phe Met Thr Ser Glu His Gln Tyr Ile Ser
        355                 360                 365 cgg aag gat gaa gga gat cgg atc att gtc ttt gag agg gga aac ctt   1212
Arg Lys Asp Glu Gly Asp Arg Ile Ile Val Phe Glu Arg Gly Asn Leu
    370                 375                 380 gtt ttt gta ttc aac ttt cat tgg act aac agc tat tca gat tac cga   1260
Val Phe Val Phe Asn Phe His Trp Thr Asn Ser Tyr Ser Asp Tyr Arg
385                 390                 395                 400 gtt ggc tgc ttc aag tca gga aag tac aag att gtt ttg gac tcg gat   1308
Val Gly Cys Phe Lys Ser Gly Lys Tyr Lys Ile Val Leu Asp Ser Asp
                405                 410                 415 gat ggc ttg ttt gga ggc ttc aac agg ctt agt cat gat gcc gag cac   1356
Asp Gly Leu Phe Gly Gly Phe Asn Arg Leu Ser His Asp Ala Glu His
            420                 425                 430 ttc acc ttt gac ggg tgg tat gat aac cgg cct cgg tcc ttc atg gta   1404
Phe Thr Phe Asp Gly Trp Tyr Asp Asn Arg Pro Arg Ser Phe Met Val
        435                 440                 445 tat gca cca tct agg aca gca gtg gtc cat gct tta gta gaa gat gaa   1452
Tyr Ala Pro Ser Arg Thr Ala Val Val His Ala Leu Val Glu Asp Glu
    450                 455                 460
```

-continued

```
gag aat gaa gca gag aat gaa gta gaa agt gaa gtg aaa cca gcc tcc      1500
Glu Asn Glu Ala Glu Asn Glu Val Glu Ser Glu Val Lys Pro Ala Ser
465                 470                 475                 480 ggc tgagatagat atttagtaag aggatcccct aaagcaggaa tggttaacct           1553
Gly gtgcatctgc attgaacgac gtatattgag acttgaattg atttgctgct caggacacag   1613
aatattaatt ccaaggctca aggcagagat acacgccatg atgcatgatc atatgaaagc    1673
tccccaactt gtaaatcatt tagcaagctg cgtgcactct gtaaattata tgtagtactt    1733
tggcaagtca cgttattatg gataccatgg atgtccgcta ggaaaaattt tgtgtatacg    1793
cctactagga tttttaaatc tcgcatgttc cacataaagt ggtggttgaa tgttgcgcga    1853
ctatttttga gtaaaatgat tgaagttatt cttcacttgg gcctgtgaaa aaaaaaaaa     1913 aaaaaaaa                                                              1921
```

<210> SEQ ID NO 51
<211> LENGTH: 481
<212> TYPE: PRT
<213> ORGANISM: Manihot esculenta

<400> SEQUENCE: 51

```
Ser Phe Gly Tyr His Val Thr Asn Phe Phe Ala Pro Ser Ser Arg Phe
  1               5                  10                  15

Gly Thr Pro Asp Asp Leu Lys Ser Leu Ile Asp Lys Ala His Glu Leu
                 20                  25                  30

Gly Leu Leu Val Leu Met Asp Ile Val His Ser His Ala Ser Asn Asn
             35                  40                  45

Thr Leu Asp Gly Leu Asn Met Phe Asp Gly Thr Asp Ser His Tyr Phe
         50                  55                  60

His Ser Gly Ser Arg Gly His His Trp Leu Trp Asp Ser Arg Leu Phe
 65                  70                  75                  80

Asn Tyr Gly Ser Trp Glu Val Leu Arg Phe Leu Leu Ser Asn Ala Arg
                 85                  90                  95

Trp Trp Leu Glu Glu Tyr Arg Phe Asp Gly Phe Arg Phe Asp Gly Val
            100                 105                 110

Thr Ser Met Met Tyr Thr Pro His Gly Leu Gln Val Ala Phe Thr Gly
        115                 120                 125

Asn Tyr Asn Glu Tyr Phe Gly Tyr Ala Thr Asp Val Asp Ala Val Ile
    130                 135                 140

Tyr Leu Met Leu Val Asn Asp Met Ile His Gly Leu Phe Pro Glu Ala
145                 150                 155                 160

Val Thr Ile Gly Glu Asp Val Ser Gly Lys Pro Thr Phe Cys Ile Pro
                165                 170                 175

Val Glu Asp Gly Gly Val Gly Phe Asp Tyr Arg Leu His Met Ala Ile
            180                 185                 190

Ala Asp Lys Trp Ile Glu Ile Leu Lys Lys Arg Asp Glu Asp Trp Lys
        195                 200                 205

Met Gly Asp Ile Val His Thr Leu Thr Asn Arg Arg Trp Leu Glu Lys
    210                 215                 220

Cys Val Ala Tyr Ala Glu Ser His Asp Gln Ala Leu Val Gly Asp Lys
225                 230                 235                 240

Thr Ile Ala Phe Trp Leu Met Asp Lys Asp Met Tyr Asp Phe Met Ala
                245                 250                 255

Arg Asp Arg Pro Ser Thr Pro Leu Ile Asp Arg Gly Ile Ala Leu His
            260                 265                 270
```

```
Lys Met Ile Arg Leu Ile Thr Met Gly Leu Gly Gly Glu Gly Tyr Leu
            275                 280                 285

Asn Phe Met Gly Asn Glu Phe Gly His Pro Glu Trp Ile Asp Phe Pro
            290                 295                 300

Arg Gly Asp Arg His Leu Pro Asn Gly Lys Val Ile Pro Gly Asn Asn
305                 310                 315                 320

His Ser Tyr Asp Lys Cys Arg Arg Phe Asp Leu Gly Asp Ala Asp
            325                 330                 335

Tyr Leu Arg Tyr His Gly Met Gln Glu Phe Asp Gln Ala Met Gln His
            340                 345                 350

Leu Glu Glu Ala Tyr Gly Phe Met Thr Ser Glu His Gln Tyr Ile Ser
            355                 360                 365

Arg Lys Asp Glu Gly Asp Arg Ile Ile Val Phe Glu Arg Gly Asn Leu
            370                 375                 380

Val Phe Val Phe Asn Phe His Trp Thr Asn Ser Tyr Ser Asp Tyr Arg
385                 390                 395                 400

Val Gly Cys Phe Lys Ser Gly Lys Tyr Lys Ile Val Leu Asp Ser Asp
            405                 410                 415

Asp Gly Leu Phe Gly Gly Phe Asn Arg Leu Ser His Asp Ala Glu His
            420                 425                 430

Phe Thr Phe Asp Gly Trp Tyr Asp Asn Arg Pro Arg Ser Phe Met Val
            435                 440                 445

Tyr Ala Pro Ser Arg Thr Ala Val Val His Ala Leu Val Glu Asp Glu
            450                 455                 460

Glu Asn Glu Ala Glu Asn Glu Val Glu Ser Glu Val Lys Pro Ala Ser
465                 470                 475                 480

Gly
```

<210> SEQ ID NO 52
<211> LENGTH: 2805
<212> TYPE: DNA
<213> ORGANISM: Manihot esculenta
<220> FEATURE:
<221> NAME/KEY: CDS
<222> LOCATION: (131)..(2674)

<400> SEQUENCE: 52

```
agtgaattcg agctcggtac ccggggatcc gattcgcatt tctcgctatt gctttccgtt      60
tatttccata tataaaatat caaatctaat cacttgcgcc atttctatct ctctccaaac     120
tctcaccgaa atg gta tac tac act gta tca ggc ata cgt ttt cct tgt       169
            Met Val Tyr Tyr Thr Val Ser Gly Ile Arg Phe Pro Cys
              1               5                  10 gca cct tca ctc tac aaa tct cag ctc acc agc ttc cat ggc ggt cga      217
Ala Pro Ser Leu Tyr Lys Ser Gln Leu Thr Ser Phe His Gly Gly Arg
         15                  20                  25 agg acc tct tct ggc ctt tcc ttc ctc ttg aag aag gag ctg ttt cct      265
Arg Thr Ser Ser Gly Leu Ser Phe Leu Leu Lys Lys Glu Leu Phe Pro
 30                  35                  40                  45 cgg aag atc ttt gct gga aag tcc tct tat gaa tct gac tcc tca aat      313
Arg Lys Ile Phe Ala Gly Lys Ser Ser Tyr Glu Ser Asp Ser Ser Asn
             50                  55                  60 tta act gtc tct gca tct gag aag gtc ctt gtt cct gat gat cag att      361
Leu Thr Val Ser Ala Ser Glu Lys Val Leu Val Pro Asp Asp Gln Ile
         65                  70                  75 gat ggc tct tct tct tca aca tat caa tta gaa acc act ggc aca gtt      409
Asp Gly Ser Ser Ser Ser Thr Tyr Gln Leu Glu Thr Thr Gly Thr Val
```

```
                   80                  85                  90
ttg gag gaa tcc cag gtt ctt ggt gat gca gag agt ctt gtg atg gaa        457
Leu Glu Glu Ser Gln Val Leu Gly Asp Ala Glu Ser Leu Val Met Glu
        95                 100                 105 gat gat aag aat gtt gag gag gat gaa gta aaa aaa gag tcg gtt cca        505
Asp Asp Lys Asn Val Glu Glu Asp Glu Val Lys Lys Glu Ser Val Pro
110                 115                 120                 125 ttg cat gag aca att agc att gga aaa agt gaa tct aaa cca agg tcc        553
Leu His Glu Thr Ile Ser Ile Gly Lys Ser Glu Ser Lys Pro Arg Ser
                    130                 135                 140 att cct cca cct ggc agt ggg cag aga ata tat gac ata gat cca agc        601
Ile Pro Pro Pro Gly Ser Gly Gln Arg Ile Tyr Asp Ile Asp Pro Ser
                145                 150                 155 ttg gca ggt ttc cgt cag cat ctt gac tac cga tat tca cag tac aaa        649
Leu Ala Gly Phe Arg Gln His Leu Asp Tyr Arg Tyr Ser Gln Tyr Lys
            160                 165                 170 agg ctg cgt gag gaa att gac aag tat gaa ggt ggt ttg gat gca ttc        697
Arg Leu Arg Glu Glu Ile Asp Lys Tyr Glu Gly Gly Leu Asp Ala Phe
        175                 180                 185 tct cgt gga ttt gaa aag ttt ggt ttc tta cgc agt gaa aca gga ata        745
Ser Arg Gly Phe Glu Lys Phe Gly Phe Leu Arg Ser Glu Thr Gly Ile
190                 195                 200                 205 act tat agg gaa tgg gca cct gga gct acg tgg gct gca ctt att gga        793
Thr Tyr Arg Glu Trp Ala Pro Gly Ala Thr Trp Ala Ala Leu Ile Gly
                    210                 215                 220 gat ttc aac aat tgg aat cct aat gca gat gtc atg act cgg aat gag        841
Asp Phe Asn Asn Trp Asn Pro Asn Ala Asp Val Met Thr Arg Asn Glu
                225                 230                 235 ttt ggt gtc tgg gag att ttt ttg cca aat aac gca gat ggt tca cca        889
Phe Gly Val Trp Glu Ile Phe Leu Pro Asn Asn Ala Asp Gly Ser Pro
            240                 245                 250 cca att cct cat ggt tct cga gta aag ata cgc atg gat act cca tct        937
Pro Ile Pro His Gly Ser Arg Val Lys Ile Arg Met Asp Thr Pro Ser
        255                 260                 265 ggc atc aaa gat tca att cct gct tgg atc aag ttc tca gtt cag gca        985
Gly Ile Lys Asp Ser Ile Pro Ala Trp Ile Lys Phe Ser Val Gln Ala
270                 275                 280                 285 cct ggt gaa atc cca tac aat gcc ata tac tat gat cca cca aag gag       1033
Pro Gly Glu Ile Pro Tyr Asn Ala Ile Tyr Tyr Asp Pro Pro Lys Glu
                    290                 295                 300 gag aag tat gtg ttc aaa cat cct cag cca aag aga cca aaa tca ctt       1081
Glu Lys Tyr Val Phe Lys His Pro Gln Pro Lys Arg Pro Lys Ser Leu
                305                 310                 315 agg att tat gaa tct cat gtt ggg atg agt agt atg gag cca ata att       1129
Arg Ile Tyr Glu Ser His Val Gly Met Ser Ser Met Glu Pro Ile Ile
            320                 325                 330 aac aca tat gcc aac ttt aga gat gat atg ctt cct cgc atc aaa aag       1177
Asn Thr Tyr Ala Asn Phe Arg Asp Asp Met Leu Pro Arg Ile Lys Lys
        335                 340                 345 ctt ggc tac aat gct gtt cag atc atg gct att caa gag cat tcc tat       1225
Leu Gly Tyr Asn Ala Val Gln Ile Met Ala Ile Gln Glu His Ser Tyr
350                 355                 360                 365 tat gct agt ttt ggg tac cat gtc aca aac ttt ttt gca cct agc agc       1273
Tyr Ala Ser Phe Gly Tyr His Val Thr Asn Phe Phe Ala Pro Ser Ser
                    370                 375                 380 cga ttt gga act cct gat gat ttg aag tct tta ata gat aaa gct cat       1321
Arg Phe Gly Thr Pro Asp Asp Leu Lys Ser Leu Ile Asp Lys Ala His
                385                 390                 395 gag tta ggg ctg ctt gtt ctc atg gat att gtt cat agc cat gcg tca       1369
```

```
                Glu Leu Gly Leu Leu Val Leu Met Asp Ile Val His Ser His Ala Ser
                            400                 405                 410 aat aat acg ttg gat ggg ctg aac atg ttt gat ggt acg gat agt cac        1417
Asn Asn Thr Leu Asp Gly Leu Asn Met Phe Asp Gly Thr Asp Ser His
        415                 420                 425 tac ttc cac tcc gga tca cgg ggt cat cat tgg ttg tgg gac tct cgc        1465
Tyr Phe His Ser Gly Ser Arg Gly His His Trp Leu Trp Asp Ser Arg
430                 435                 440                 445 ctt ttc aac tat gga agc tgg gag gtg cta aga ttt ctt ctt tca aat        1513
Leu Phe Asn Tyr Gly Ser Trp Glu Val Leu Arg Phe Leu Leu Ser Asn
                450                 455                 460 gca aga tgg tgg ttg gaa gag tac agg ttt gat ggt ttt aga ttt gat        1561
Ala Arg Trp Trp Leu Glu Glu Tyr Arg Phe Asp Gly Phe Arg Phe Asp
            465                 470                 475 ggg gtg act tcc atg atg tac act ccc cat ggg ttg cag gta gct ttt        1609
Gly Val Thr Ser Met Met Tyr Thr Pro His Gly Leu Gln Val Ala Phe
        480                 485                 490 act ggc aac tac aat gag tac ttt gga tat gca act gat gta gat gct        1657
Thr Gly Asn Tyr Asn Glu Tyr Phe Gly Tyr Ala Thr Asp Val Asp Ala
    495                 500                 505 gtg att tat ttg atg ctt gtg aat gat atg att cac ggt ctt ttc cct        1705
Val Ile Tyr Leu Met Leu Val Asn Asp Met Ile His Gly Leu Phe Pro
510                 515                 520                 525 gag gct gtt acc att ggt gaa gat gtt agc gga aag cca aca ttt tgc        1753
Glu Ala Val Thr Ile Gly Glu Asp Val Ser Gly Lys Pro Thr Phe Cys
                530                 535                 540 att cca gtg gaa gat ggt ggt gtt gga ttt gat tac cgt ctc cac atg        1801
Ile Pro Val Glu Asp Gly Gly Val Gly Phe Asp Tyr Arg Leu His Met
            545                 550                 555 gcc att gcc gat aaa tgg att gag att ctt aag aag aga gat gag gac        1849
Ala Ile Ala Asp Lys Trp Ile Glu Ile Leu Lys Lys Arg Asp Glu Asp
        560                 565                 570 tgg aaa atg ggt gac att gtg cat aca ctc acc aac aga agg tgg ttg        1897
Trp Lys Met Gly Asp Ile Val His Thr Leu Thr Asn Arg Arg Trp Leu
    575                 580                 585 gaa aaa tgt gtt gct tat gct gaa agt cat gac caa gct ctt gtt ggt        1945
Glu Lys Cys Val Ala Tyr Ala Glu Ser His Asp Gln Ala Leu Val Gly
590                 595                 600                 605 gac aaa act att gca ttt tgg ctg atg gac aag gac atg tac gac ttc        1993
Asp Lys Thr Ile Ala Phe Trp Leu Met Asp Lys Asp Met Tyr Asp Phe
                610                 615                 620 atg gct cgt gac aga cca tct act cct ctt ata gat cgt gga ata gca        2041
Met Ala Arg Asp Arg Pro Ser Thr Pro Leu Ile Asp Arg Gly Ile Ala
            625                 630                 635 ttg cac aaa atg atc agg ctt att acc atg ggc tta ggc gga gaa gga        2089
Leu His Lys Met Ile Arg Leu Ile Thr Met Gly Leu Gly Gly Glu Gly
        640                 645                 650 tat ttg aat ttt atg gga aat gaa ttt gga cat cct gag tgg att gat        2137
Tyr Leu Asn Phe Met Gly Asn Glu Phe Gly His Pro Glu Trp Ile Asp
    655                 660                 665 ttt cca aga ggg gat cga cat ctg ccc aat ggt aaa gta att cca ggg        2185
Phe Pro Arg Gly Asp Arg His Leu Pro Asn Gly Lys Val Ile Pro Gly
670                 675                 680                 685 aac aac cac agt tat gat aaa tgc cgt cgt aga ttt gat cta ggt gat        2233
Asn Asn His Ser Tyr Asp Lys Cys Arg Arg Arg Phe Asp Leu Gly Asp
                690                 695                 700 gca gac tat cta aga tat cat gga atg caa gag ttt gat cag gca atg        2281
Ala Asp Tyr Leu Arg Tyr His Gly Met Gln Glu Phe Asp Gln Ala Met
            705                 710                 715
```

-continued

| | | | | | | | | | | | | | | | |
|---|---|---|---|---|---|---|---|---|---|---|---|---|---|---|---|
| caa | cat | ctt | gaa | gaa | gcc | tat | ggt | ttc | atg | act | tct | gag | cac | cag | tat | 2329 |
| Gln | His | Leu | Glu | Glu | Ala | Tyr | Gly | Phe | Met | Thr | Ser | Glu | His | Gln | Tyr |
| | 720 | | | | | 725 | | | | | 730 | | | | |
| ata | tca | cgg | aag | gat | gaa | gga | gat | cgg | atc | att | gtc | ttt | gag | agg | gga | 2377 |
| Ile | Ser | Arg | Lys | Asp | Glu | Gly | Asp | Arg | Ile | Ile | Val | Phe | Glu | Arg | Gly |
| 735 | | | | | 740 | | | | | 745 | | | | | |
| aac | ctt | gtt | ttt | gta | ttc | aac | ttt | cat | tgg | act | aac | agc | tat | tca | gat | 2425 |
| Asn | Leu | Val | Phe | Val | Phe | Asn | Phe | His | Trp | Thr | Asn | Ser | Tyr | Ser | Asp |
| 750 | | | | | 755 | | | | | 760 | | | | | 765 |
| tac | cga | gtt | ggc | tgc | ttc | aag | tca | gga | aag | tac | aag | att | gtt | ttg | gac | 2473 |
| Tyr | Arg | Val | Gly | Cys | Phe | Lys | Ser | Gly | Lys | Tyr | Lys | Ile | Val | Leu | Asp |
| | | | 770 | | | | | 775 | | | | | 780 | | |
| tcg | gat | gat | ggc | ttg | ttt | gga | ggc | ttc | aac | agg | ctt | agt | cat | gat | gcc | 2521 |
| Ser | Asp | Asp | Gly | Leu | Phe | Gly | Gly | Phe | Asn | Arg | Leu | Ser | His | Asp | Ala |
| | | 785 | | | | | 790 | | | | | 795 | | | |
| gag | cac | ttc | acc | ttt | gac | ggg | tgg | tat | gat | aac | cgg | cct | cgg | tcc | ttc | 2569 |
| Glu | His | Phe | Thr | Phe | Asp | Gly | Trp | Tyr | Asp | Asn | Arg | Pro | Arg | Ser | Phe |
| | 800 | | | | | 805 | | | | | 810 | | | | |
| atg | gta | tat | gca | cca | tct | agg | aca | gca | gtg | gtc | tat | gct | tta | gta | gaa | 2617 |
| Met | Val | Tyr | Ala | Pro | Ser | Arg | Thr | Ala | Val | Val | Tyr | Ala | Leu | Val | Glu |
| 815 | | | | | 820 | | | | | 825 | | | | | |
| gat | gaa | gag | aat | gaa | gca | gag | aat | gaa | gta | gaa | agt | gaa | gtg | aaa | cca | 2665 |
| Asp | Glu | Glu | Asn | Glu | Ala | Glu | Asn | Glu | Val | Glu | Ser | Glu | Val | Lys | Pro |
| 830 | | | | | 835 | | | | | 840 | | | | | 845 |
| gcc | tcc | ggc | tgagatagat | atttagtaag | aggatcccct | aaagcaggaa | | | | | | | | | | 2714 |
| Ala | Ser | Gly | | | | | | | | | | | | | | tggttaacct gtgcatctgc attgaacgac gtatattgag actggaaatc catatgacta   2774 gtagatcctc tagagtcgac ctgcaggcat g   2805

<210> SEQ ID NO 53
<211> LENGTH: 848
<212> TYPE: PRT
<213> ORGANISM: Manihot esculenta

<400> SEQUENCE: 53

Met Val Tyr Tyr Thr Val Ser Gly Ile Arg Phe Pro Cys Ala Pro Ser
1               5                   10                  15

Leu Tyr Lys Ser Gln Leu Thr Ser Phe His Gly Gly Arg Arg Thr Ser
            20                  25                  30

Ser Gly Leu Ser Phe Leu Leu Lys Lys Glu Leu Phe Pro Arg Lys Ile
        35                  40                  45

Phe Ala Gly Lys Ser Ser Tyr Glu Ser Asp Ser Asn Leu Thr Val
    50                  55                  60

Ser Ala Ser Glu Lys Val Leu Val Pro Asp Asp Gln Ile Asp Gly Ser
65                  70                  75                  80

Ser Ser Ser Thr Tyr Gln Leu Glu Thr Thr Gly Thr Val Leu Glu Glu
                85                  90                  95

Ser Gln Val Leu Gly Asp Ala Glu Ser Leu Val Met Glu Asp Asp Lys
            100                 105                 110

Asn Val Glu Glu Asp Glu Val Lys Lys Glu Ser Val Pro Leu His Glu
        115                 120                 125

Thr Ile Ser Ile Gly Lys Ser Glu Ser Lys Pro Arg Ser Ile Pro Pro
    130                 135                 140

Pro Gly Ser Gly Gln Arg Ile Tyr Asp Ile Asp Pro Ser Leu Ala Gly
145                 150                 155                 160

Phe Arg Gln His Leu Asp Tyr Arg Tyr Ser Gln Tyr Lys Arg Leu Arg
                165                 170                 175

```
Glu Glu Ile Asp Lys Tyr Glu Gly Gly Leu Asp Ala Phe Ser Arg Gly
            180                 185                 190

Phe Glu Lys Phe Gly Phe Leu Arg Ser Glu Thr Gly Ile Thr Tyr Arg
        195                 200                 205

Glu Trp Ala Pro Gly Ala Thr Trp Ala Ala Leu Ile Gly Asp Phe Asn
    210                 215                 220

Asn Trp Asn Pro Asn Ala Asp Val Met Thr Arg Asn Glu Phe Gly Val
225                 230                 235                 240

Trp Glu Ile Phe Leu Pro Asn Asn Ala Asp Gly Ser Pro Pro Ile Pro
                245                 250                 255

His Gly Ser Arg Val Lys Ile Arg Met Asp Thr Pro Ser Gly Ile Lys
            260                 265                 270

Asp Ser Ile Pro Ala Trp Ile Lys Phe Ser Val Gln Ala Pro Gly Glu
        275                 280                 285

Ile Pro Tyr Asn Ala Ile Tyr Tyr Asp Pro Pro Lys Glu Glu Lys Tyr
    290                 295                 300

Val Phe Lys His Pro Gln Pro Lys Arg Pro Lys Ser Leu Arg Ile Tyr
305                 310                 315                 320

Glu Ser His Val Gly Met Ser Ser Met Glu Pro Ile Ile Asn Thr Tyr
                325                 330                 335

Ala Asn Phe Arg Asp Asp Met Leu Pro Arg Ile Lys Lys Leu Gly Tyr
            340                 345                 350

Asn Ala Val Gln Ile Met Ala Ile Gln Glu His Ser Tyr Tyr Ala Ser
        355                 360                 365

Phe Gly Tyr His Val Thr Asn Phe Phe Ala Pro Ser Ser Arg Phe Gly
    370                 375                 380

Thr Pro Asp Asp Leu Lys Ser Leu Ile Asp Lys Ala His Glu Leu Gly
385                 390                 395                 400

Leu Leu Val Leu Met Asp Ile Val His Ser His Ala Ser Asn Asn Thr
                405                 410                 415

Leu Asp Gly Leu Asn Met Phe Asp Gly Thr Asp Ser His Tyr Phe His
            420                 425                 430

Ser Gly Ser Arg Gly His His Trp Leu Trp Asp Ser Arg Leu Phe Asn
        435                 440                 445

Tyr Gly Ser Trp Glu Val Leu Arg Phe Leu Leu Ser Asn Ala Arg Trp
    450                 455                 460

Trp Leu Glu Glu Tyr Arg Phe Asp Gly Phe Arg Phe Asp Gly Val Thr
465                 470                 475                 480

Ser Met Met Tyr Thr Pro His Gly Leu Gln Val Ala Phe Thr Gly Asn
                485                 490                 495

Tyr Asn Glu Tyr Phe Gly Tyr Ala Thr Asp Val Asp Ala Val Ile Tyr
            500                 505                 510

Leu Met Leu Val Asn Asp Met Ile His Gly Leu Phe Pro Glu Ala Val
        515                 520                 525

Thr Ile Gly Glu Asp Val Ser Gly Lys Pro Thr Phe Cys Ile Pro Val
    530                 535                 540

Glu Asp Gly Gly Val Gly Phe Asp Tyr Arg Leu His Met Ala Ile Ala
545                 550                 555                 560

Asp Lys Trp Ile Glu Ile Leu Lys Lys Arg Asp Glu Asp Trp Lys Met
                565                 570                 575

Gly Asp Ile Val His Thr Leu Thr Asn Arg Arg Trp Leu Glu Lys Cys
            580                 585                 590
```

```
Val Ala Tyr Ala Glu Ser His Asp Gln Ala Leu Val Gly Asp Lys Thr
            595                 600                 605

Ile Ala Phe Trp Leu Met Asp Lys Asp Met Tyr Asp Phe Met Ala Arg
        610                 615                 620

Asp Arg Pro Ser Thr Pro Leu Ile Asp Arg Gly Ile Ala Leu His Lys
625                 630                 635                 640

Met Ile Arg Leu Ile Thr Met Gly Leu Gly Gly Glu Gly Tyr Leu Asn
                645                 650                 655

Phe Met Gly Asn Glu Phe Gly His Pro Glu Trp Ile Asp Phe Pro Arg
            660                 665                 670

Gly Asp Arg His Leu Pro Asn Gly Lys Val Ile Pro Gly Asn Asn His
        675                 680                 685

Ser Tyr Asp Lys Cys Arg Arg Phe Asp Leu Gly Asp Ala Asp Tyr
            690                 695                 700

Leu Arg Tyr His Gly Met Gln Glu Phe Asp Gln Ala Met Gln His Leu
705                 710                 715                 720

Glu Glu Ala Tyr Gly Phe Met Thr Ser Glu His Gln Tyr Ile Ser Arg
                725                 730                 735

Lys Asp Glu Gly Asp Arg Ile Ile Val Phe Glu Arg Gly Asn Leu Val
            740                 745                 750

Phe Val Phe Asn Phe His Trp Thr Asn Ser Tyr Ser Asp Tyr Arg Val
        755                 760                 765

Gly Cys Phe Lys Ser Gly Lys Tyr Lys Ile Val Leu Asp Ser Asp Asp
770                 775                 780

Gly Leu Phe Gly Gly Phe Asn Arg Leu Ser His Asp Ala Glu His Phe
785                 790                 795                 800

Thr Phe Asp Gly Trp Tyr Asp Asn Arg Pro Arg Ser Phe Met Val Tyr
                805                 810                 815

Ala Pro Ser Arg Thr Ala Val Val Tyr Ala Leu Val Glu Asp Glu Glu
            820                 825                 830

Asn Glu Ala Glu Asn Glu Val Glu Ser Glu Val Lys Pro Ala Ser Gly
        835                 840                 845

<210> SEQ ID NO 54
<211> LENGTH: 879
<212> TYPE: PRT
<213> ORGANISM: Solanum tuberosum

<400> SEQUENCE: 54

Met Val Tyr Thr Leu Ser Gly Val Arg Phe Pro Thr Val Pro Ser Val
 1               5                  10                  15

Tyr Lys Ser Asn Gly Phe Ser Ser Asn Gly Asp Arg Arg Asn Ala Asn
            20                  25                  30

Val Ser Val Phe Leu Lys Lys His Ser Leu Ser Arg Lys Ile Leu Ala
        35                  40                  45

Glu Lys Ser Ser Tyr Asn Ser Glu Phe Arg Pro Ser Thr Val Ala Ala
    50                  55                  60

Ser Gly Lys Val Leu Val Pro Gly Thr Gln Ser Asp Ser Ser Ser
65                  70                  75                  80

Ser Thr Asp Gln Phe Glu Phe Thr Glu Thr Ser Pro Glu Asn Ser Pro
                85                  90                  95

Ala Ser Thr Asp Val Asp Ser Ser Thr Met Glu His Ala Ser Gln Ile
            100                 105                 110

Lys Thr Glu Asn Asp Asp Val Glu Pro Ser Ser Asp Leu Thr Gly Ser
        115                 120                 125
```

```
Val Glu Glu Leu Asp Phe Ala Ser Ser Leu Gln Leu Gln Glu Gly Gly
    130                 135                 140

Lys Leu Glu Glu Ser Lys Thr Leu Asn Thr Ser Glu Glu Thr Ile Ile
145                 150                 155                 160

Asp Glu Ser Asp Arg Ile Arg Glu Arg Gly Ile Pro Pro Gly Leu
                165                 170                 175

Gly Gln Lys Ile Tyr Glu Ile Asp Pro Leu Leu Thr Asn Tyr Arg Gln
            180                 185                 190

His Leu Asp Tyr Arg Tyr Ser Gln Tyr Lys Lys Leu Arg Glu Ala Ile
        195                 200                 205

Asp Lys Tyr Glu Gly Gly Leu Glu Ala Phe Ser Arg Gly Tyr Glu Lys
    210                 215                 220

Met Gly Phe Thr Arg Ser Ala Thr Gly Ile Thr Tyr Arg Glu Trp Ala
225                 230                 235                 240

Leu Gly Ala Gln Ser Ala Ala Leu Ile Gly Asp Phe Asn Asn Trp Asp
                245                 250                 255

Ala Asn Ala Asp Ile Met Thr Arg Asn Glu Phe Gly Val Trp Glu Ile
            260                 265                 270

Phe Leu Pro Asn Asn Val Asp Gly Ser Pro Ala Ile Pro His Gly Ser
        275                 280                 285

Arg Val Lys Ile Arg Met Asp Thr Pro Ser Gly Val Lys Asp Ser Ile
    290                 295                 300

Pro Ala Trp Ile Asn Tyr Ser Leu Gln Leu Pro Asp Glu Ile Pro Tyr
305                 310                 315                 320

Asn Gly Ile His Tyr Asp Pro Pro Glu Glu Glu Arg Tyr Ile Phe Gln
                325                 330                 335

His Pro Arg Pro Lys Lys Pro Lys Ser Leu Arg Ile Tyr Glu Ser His
            340                 345                 350

Ile Gly Met Ser Ser Pro Glu Pro Lys Ile Asn Ser Tyr Val Asn Phe
        355                 360                 365

Arg Asp Glu Val Leu Pro Arg Ile Lys Lys Leu Gly Tyr Asn Ala Leu
    370                 375                 380

Gln Ile Met Ala Ile Gln Glu His Ser Tyr Tyr Ala Ser Phe Gly Tyr
385                 390                 395                 400

His Val Thr Asn Phe Phe Ala Pro Ser Ser Arg Phe Gly Thr Pro Asp
                405                 410                 415

Asp Leu Lys Ser Leu Ile Asp Lys Ala His Glu Leu Gly Ile Val Val
            420                 425                 430

Leu Met Asp Ile Val His Ser His Ala Ser Asn Asn Thr Leu Asp Gly
        435                 440                 445

Leu Asn Met Phe Asp Cys Thr Asp Ser Cys Tyr Phe His Ser Gly Ala
    450                 455                 460

Arg Gly Tyr His Trp Met Trp Asp Ser Arg Leu Phe Asn Tyr Gly Asn
465                 470                 475                 480

Trp Glu Val Leu Arg Tyr Leu Leu Ser Asn Ala Arg Trp Ala Leu Asp
                485                 490                 495

Ala Phe Lys Phe Asp Gly Phe Arg Phe Asp Gly Val Thr Ser Met Met
            500                 505                 510

Tyr Ile His His Gly Leu Ser Val Gly Phe Thr Gly Asn Tyr Glu Glu
        515                 520                 525

Tyr Phe Gly Leu Ala Thr Asp Val Asp Ala Val Val Tyr Leu Met Leu
    530                 535                 540
```

-continued

```
Val Asn Asp Leu Ile His Gly Leu Pro Pro Asp Ala Ile Thr Ile Gly
545                 550                 555                 560

Glu Asp Val Ser Gly His Pro Thr Phe Cys Asp Pro Val Gln Glu Gly
                565                 570                 575

Gly Val Gly Phe Asp Tyr Arg Leu His Met Ala Ile Ala Asp Lys Arg
            580                 585                 590

Ile Glu Leu Leu Lys Lys Arg Asp Glu Asp Trp Arg Val Gly Asp Ile
        595                 600                 605

Val His Thr Leu Thr Asn Arg Arg Trp Ser Glu Lys Cys Val Ser Tyr
    610                 615                 620

Ala Glu Ser His Asp Gln Ala Leu Val Gly Asp Lys Thr Ile Ala Phe
625                 630                 635                 640

Trp Leu Met Asp Lys Asp Met Tyr Asp Phe Met Ala Leu Asp Arg Pro
                645                 650                 655

Ser Thr Ser Leu Ile Asp Arg Gly Ile Ala Leu His Lys Met Ile Arg
            660                 665                 670

Leu Val Thr Met Gly Leu Gly Gly Glu Gly Tyr Leu Asn Phe Met Gly
        675                 680                 685

Asn Glu Phe Gly His Pro Glu Trp Ile Asp Phe Pro Arg Ala Glu Gln
    690                 695                 700

His Leu Ser Asp Gly Ser Val Ile Pro Gly Asn Gln Phe Ser Tyr Asp
705                 710                 715                 720

Lys Cys Arg Arg Arg Phe Asp Leu Gly Asp Ala Glu Tyr Leu Arg Tyr
                725                 730                 735

Arg Gly Leu Gln Glu Phe Asp Arg Pro Met Gln Tyr Leu Glu Asp Lys
            740                 745                 750

Tyr Glu Phe Met Thr Ser Glu His Gln Phe Ile Ser Arg Lys Asp Glu
        755                 760                 765

Gly Asp Arg Met Ile Val Phe Glu Lys Gly Asn Leu Val Phe Val Phe
    770                 775                 780

Asn Phe His Trp Thr Lys Ser Tyr Ser Asp Tyr Arg Ile Ala Cys Leu
785                 790                 795                 800

Lys Pro Gly Lys Tyr Lys Val Ala Leu Asp Ser Asp Pro Leu Phe
                805                 810                 815

Gly Gly Phe Gly Arg Ile Asp His Asn Ala Glu Tyr Phe Thr Phe Glu
            820                 825                 830

Gly Trp Tyr Asp Asp Arg Pro Arg Ser Ile Met Val Tyr Ala Pro Cys
        835                 840                 845

Lys Thr Ala Val Val Tyr Ala Leu Val Asp Lys Glu Glu Glu Glu
    850                 855                 860

Glu Glu Glu Val Ala Ala Val Glu Glu Val Val Val Glu Glu Glu
865                 870                 875

<210> SEQ ID NO 55
<211> LENGTH: 922
<212> TYPE: PRT
<213> ORGANISM: Pisum sativum

<400> SEQUENCE: 55

Met Val Tyr Thr Ile Ser Gly Ile Arg Phe Pro Val Leu Pro Ser Leu
1               5                   10                  15

His Lys Ser Thr Leu Arg Cys Asp Arg Arg Ala Ser Ser His Ser Phe
                20                  25                  30

Phe Leu Lys Asn Asn Ser Ser Phe Ser Arg Thr Ser Leu Tyr Ala
            35                  40                  45
```

-continued

```
Lys Phe Ser Arg Asp Ser Glu Thr Lys Ser Ser Thr Ile Ala Glu Ser
    50                  55                  60

Asp Lys Val Leu Ile Pro Glu Asp Gln Asp Asn Ser Val Ser Leu Ala
 65                  70                  75                  80

Asp Gln Leu Glu Asn Pro Asp Ile Thr Ser Glu Asp Ala Gln Asn Leu
                 85                  90                  95

Glu Asp Leu Thr Met Lys Asp Gly Asn Lys Tyr Asn Ile Asp Glu Ser
            100                 105                 110

Thr Ser Ser Tyr Arg Glu Val Gly Asp Glu Lys Gly Ser Val Thr Ser
        115                 120                 125

Ser Ser Leu Val Asp Val Asn Thr Asp Thr Gln Ala Lys Lys Thr Ser
    130                 135                 140

Val His Ser Asp Lys Lys Val Lys Val Asp Lys Pro Lys Ile Ile Pro
145                 150                 155                 160

Pro Pro Gly Thr Gly Gln Lys Ile Tyr Glu Ile Asp Pro Leu Leu Gln
                165                 170                 175

Ala His Arg Gln His Leu Asp Phe Arg Tyr Gly Gln Tyr Lys Arg Ile
            180                 185                 190

Arg Glu Glu Ile Asp Lys Tyr Glu Gly Gly Leu Asp Ala Phe Ser Arg
        195                 200                 205

Gly Tyr Glu Lys Phe Gly Phe Thr Arg Ser Ala Thr Gly Ile Thr Tyr
    210                 215                 220

Arg Glu Trp Ala Pro Gly Ala Lys Ser Ala Ala Leu Val Gly Asp Phe
225                 230                 235                 240

Asn Asn Trp Asn Pro Asn Ala Asp Val Met Thr Lys Asp Ala Phe Gly
                245                 250                 255

Val Trp Glu Ile Phe Leu Pro Asn Asn Ala Asp Gly Ser Pro Pro Ile
            260                 265                 270

Pro His Gly Ser Arg Val Lys Ile His Met Asp Thr Pro Ser Gly Ile
        275                 280                 285

Lys Asp Ser Ile Pro Ala Trp Ile Lys Phe Ser Val Gln Ala Pro Gly
    290                 295                 300

Glu Ile Pro Tyr Asn Gly Ile Tyr Tyr Asp Pro Pro Glu Glu Glu Lys
305                 310                 315                 320

Tyr Val Phe Lys His Pro Gln Pro Lys Arg Pro Gln Ser Ile Arg Ile
                325                 330                 335

Tyr Glu Ser His Ile Gly Met Ser Ser Pro Glu Pro Lys Ile Asn Thr
            340                 345                 350

Tyr Ala Asn Phe Arg Asp Asp Val Leu Pro Arg Ile Lys Lys Leu Gly
        355                 360                 365

Tyr Asn Ala Val Gln Ile Met Ala Ile Gln Glu His Ser Tyr Tyr Ala
    370                 375                 380

Ser Phe Gly Tyr His Val Thr Asn Phe Phe Ala Pro Ser Ser Arg Phe
385                 390                 395                 400

Gly Thr Pro Glu Asp Leu Lys Ser Leu Ile Asp Arg Ala His Glu Leu
                405                 410                 415

Gly Leu Leu Val Leu Met Asp Ile Val His Ser His Ser Ser Asn Asn
            420                 425                 430

Thr Leu Asp Gly Leu Asn Met Phe Asp Gly Thr Asp Gly His Tyr Phe
        435                 440                 445

His Pro Gly Ser Arg Gly Tyr His Trp Met Trp Asp Ser Arg Leu Phe
    450                 455                 460
```

-continued

```
Asn Tyr Gly Ser Trp Glu Val Leu Arg Tyr Leu Leu Ser Asn Ala Arg
465                 470                 475                 480

Trp Ala Leu Asp Glu Tyr Lys Phe Asp Gly Phe Arg Phe Asp Gly Val
            485                 490                 495

Thr Ser Met Met Tyr Thr His His Gly Leu Gln Val Ser Phe Thr Gly
        500                 505                 510

Asn Tyr Ser Glu Tyr Phe Gly Leu Ala Thr Asp Val Glu Ala Val Val
    515                 520                 525

Tyr Met Met Leu Val Asn Asp Leu Ile His Gly Leu Pro Pro Glu Ala
530                 535                 540

Val Ser Ile Gly Glu Asp Val Ser Gly Met Pro Thr Phe Cys Leu Pro
545                 550                 555                 560

Thr Gln Asp Gly Gly Ile Gly Phe Asn Tyr Arg Leu His Met Ala Val
                565                 570                 575

Ala Asp Lys Trp Ile Glu Leu Leu Lys Lys Gln Asp Glu Asp Trp Arg
            580                 585                 590

Met Gly Asp Ile Val His Thr Leu Thr Asn Arg Arg Trp Leu Glu Lys
        595                 600                 605

Cys Val Val Tyr Ala Glu Ser His Asp Gln Ala Leu Val Gly Asp Lys
    610                 615                 620

Thr Leu Ala Phe Trp Leu Met Asp Lys Asp Met Tyr Asp Phe Met Ala
625                 630                 635                 640

Leu Asp Arg Pro Ser Thr Pro Leu Ile Asp Arg Gly Ile Ala Leu His
                645                 650                 655

Lys Met Ile Arg Leu Ile Thr Met Gly Leu Gly Gly Glu Gly Tyr Leu
            660                 665                 670

Asn Phe Met Gly Asn Glu Phe Gly His Pro Glu Trp Ile Asp Phe Pro
        675                 680                 685

Arg Gly Glu Gln His Leu Pro Asn Gly Lys Ile Val Pro Gly Asn Asn
    690                 695                 700

Asn Ser Tyr Asp Lys Cys Arg Arg Phe Asp Leu Gly Asp Ala Asp
705                 710                 715                 720

Tyr Leu Arg Tyr His Gly Met Gln Glu Phe Asp Arg Ala Met Gln His
                725                 730                 735

Leu Glu Glu Arg Tyr Gly Phe Met Thr Ser Glu His Gln Tyr Ile Ser
            740                 745                 750

Arg Lys Asn Glu Gly Asp Arg Val Ile Ile Phe Glu Arg Asp Asn Leu
        755                 760                 765

Val Phe Val Phe Asn Phe His Trp Thr Asn Ser Tyr Ser Asp Tyr Lys
    770                 775                 780

Val Gly Cys Leu Lys Pro Gly Lys Tyr Lys Ile Val Leu Asp Ser Asp
785                 790                 795                 800

Asp Thr Leu Phe Gly Gly Phe Asn Arg Leu Asn His Thr Ala Glu Tyr
                805                 810                 815

Phe Thr Ser Glu Gly Trp Tyr Asp Asp Arg Pro Arg Ser Phe Leu Val
            820                 825                 830

Tyr Ala Pro Ser Arg Thr Ala Val Val Tyr Ala Leu Ala Asp Gly Val
        835                 840                 845

Glu Ser Glu Pro Ile Glu Leu Ser Asp Gly Val Glu Ser Glu Pro Ile
    850                 855                 860

Glu Leu Ser Val Gly Val Glu Ser Glu Pro Ile Glu Leu Ser Val Glu
865                 870                 875                 880

Glu Ala Glu Ser Glu Pro Ile Glu Arg Ser Val Glu Glu Val Glu Ser
```

885                 890                 895
Glu Thr Thr Gln Gln Ser Val Glu Val Glu Ser Glu Thr Thr Gln Gln
                900                 905                 910

Ser Val Glu Val Glu Ser Glu Thr Thr Gln
        915                 920

<210> SEQ ID NO 56
<211> LENGTH: 848
<212> TYPE: PRT
<213> ORGANISM: Arabidopsis thaliana

<400> SEQUENCE: 56

Arg Ala Arg Val Arg Phe Pro His Leu Pro Ser Ile Lys Lys Lys Asn
  1               5                  10                  15

Ser Ser Leu His Ser Phe Asn Glu Asp Leu Arg Arg Ser Asn Ala Val
                 20                  25                  30

Ser Phe Ser Leu Arg Lys Asp Ser Arg Ser Ser Gly Lys Val Phe Ala
             35                  40                  45

Arg Lys Pro Ser Tyr Asp Ser Asp Ser Ser Ser Leu Ala Thr Thr Ala
         50                  55                  60

Ser Glu Lys Leu Arg Gly His Gln Ser Asp Ser Ser Ser Ala Ser
 65                  70                  75                  80

Asp Gln Val Gln Ser Arg Asp Thr Val Ser Asp Thr Gln Val Leu
                 85                  90                  95

Gly Asn Val Asp Val Gln Lys Thr Glu Glu Ala Gln Glu Thr Glu Thr
                100                 105                 110

Leu Asp Gln Thr Ser Ala Leu Ser Thr Ser Gly Ser Ile Ser Tyr Lys
            115                 120                 125

Glu Asp Phe Ala Lys Met Ser His Ser Val Asp Gln Glu Val Gly Gln
        130                 135                 140

Arg Lys Ile Pro Pro Gly Asp Gly Lys Arg Ile Tyr Asp Ile Asp
145                 150                 155                 160

Pro Met Leu Asn Ser His Arg Asn His Leu Asp Tyr Arg Tyr Gly Gln
                165                 170                 175

Tyr Arg Lys Leu Arg Glu Glu Ile Asp Lys Asn Glu Gly Gly Leu Glu
            180                 185                 190

Ala Phe Ser Arg Gly Tyr Glu Ile Phe Gly Phe Thr Arg Ser Ala Thr
        195                 200                 205

Gly Ile Thr Tyr Arg Glu Trp Ala Pro Gly Ala Lys Ala Ala Ser Leu
    210                 215                 220

Ile Gly Asp Phe Asn Asn Trp Asn Ala Lys Ser Asp Val Met Ala Arg
225                 230                 235                 240

Asn Asp Phe Gly Val Trp Glu Ile Phe Leu Pro Asn Asn Ala Asp Gly
                245                 250                 255

Ser Pro Ala Ile Pro His Gly Ser Arg Val Lys Ile Arg Met Asp Thr
            260                 265                 270

Pro Ser Gly Ile Lys Asp Ser Ile Pro Ala Trp Ile Lys Tyr Ser Val
        275                 280                 285

Gln Pro Pro Gly Glu Ile Pro Tyr Asn Gly Val Tyr Tyr Asp Pro Pro
    290                 295                 300

Glu Glu Asp Lys Tyr Ala Phe Lys His Pro Arg Pro Lys Lys Pro Thr
305                 310                 315                 320

Ser Leu Arg Ile Tyr Glu Ser His Val Gly Met Ser Ser Thr Glu Pro
                325                 330                 335

-continued

```
Lys Ile Asn Thr Tyr Ala Asn Phe Arg Asp Asp Val Leu Pro Arg Ile
            340                 345                 350

Lys Lys Leu Gly Tyr Asn Ala Val Gln Ile Met Ala Ile Gln Glu His
        355                 360                 365

Ala Tyr Tyr Ala Ser Phe Gly Tyr His Val Thr Asn Phe Phe Ala Pro
    370                 375                 380

Ser Ser Arg Phe Gly Thr Pro Asp Asp Leu Lys Ser Leu Ile Asp Lys
385                 390                 395                 400

Ala His Glu Leu Gly Leu Val Val Leu Met Asp Ile Val His Ser His
                405                 410                 415

Ala Ser Lys Asn Thr Leu Asp Gly Leu Asp Met Phe Asp Gly Thr Asp
            420                 425                 430

Gly Tyr Phe His Ser Gly Ser Arg Gly Tyr His Trp Met Trp Asp Thr
        435                 440                 445

Arg Leu Phe Asn Tyr Gly Ser Trp Glu Val Leu Arg Tyr Leu Leu Ser
    450                 455                 460

Asn Ala Arg Trp Ala Leu Glu Glu Tyr Lys Phe Asp Gly Phe Arg Phe
465                 470                 475                 480

Asp Gly Val Thr Ser Met Met Tyr Thr His His Gly Leu Gln Val Glu
                485                 490                 495

Phe Thr Gly Asn Tyr Asn Glu Tyr Phe Gly Ala Ser Thr Asp Val Asp
            500                 505                 510

Ala Val Val Tyr Leu Met Leu Val Asn Asp Leu Ile His Gly Leu Tyr
        515                 520                 525

Pro Glu Ala Ile Val Val Gly Glu Asp Val Ser Gly Met Pro Ala Phe
    530                 535                 540

Cys Val Pro Val Arg Asp Gly Gly Val Gly Phe Asp Tyr Arg Leu His
545                 550                 555                 560

Met Ala Val Ala Asp Lys Trp Ile Glu Leu Leu Lys Lys Arg Asp Glu
                565                 570                 575

Asp Trp Gln Val Gly Asp Ile Thr Phe Thr Leu Thr Asn Arg Arg Trp
            580                 585                 590

Gly Glu Lys Cys Val Val Tyr Ala Glu Ser His Asp Gln Ala Leu Val
        595                 600                 605

Gly Asp Lys Thr Ile Ala Phe Trp Leu Met Asp Lys Asp Met Tyr Asp
    610                 615                 620

Phe Met Ala Val Asp Arg Gln Ala Thr Pro Arg Val Asp Arg Gly Ile
625                 630                 635                 640

Ala Leu His Lys Met Ile Arg Leu Ile Thr Met Gly Leu Gly Gly Glu
                645                 650                 655

Gly Tyr Leu Asn Phe Met Gly Asn Glu Phe Gly His Pro Glu Trp Ile
            660                 665                 670

Asp Phe Pro Arg Thr Asp Gln His Leu Pro Asp Gly Arg Val Ile Ala
        675                 680                 685

Gly Asn Asn Gly Ser Tyr Asp Lys Ser Arg Arg Phe Asp Leu Gly
    690                 695                 700

Asp Ala Glu Tyr Leu Arg Tyr His Gly Leu Gln Glu Phe Asp Arg Ala
705                 710                 715                 720

Met Gln Asn Leu Glu Glu Thr Tyr Gly Phe Met Thr Ser Glu His Gln
                725                 730                 735

Tyr Ile Ser Pro Lys Asp Glu Gly Asp Arg Val Ile Val Phe Glu Arg
            740                 745                 750

Gly Asn Leu Leu Phe Val Phe Asn Phe His Trp Thr Asn Ser Tyr Ser
```

```
                755                 760                 765
Asp Tyr Arg Ile Gly Cys Ser Val Pro Gly Lys Tyr Lys Ile Val Leu
        770                 775                 780

Asp Ser Asp Asn Ser Leu Phe Gly Gly Phe Asn Arg Leu Asp Asp Ser
785                 790                 795                 800

Ala Glu Phe Phe Thr Ser Asp Gly Arg His Asp Asp Arg Pro Cys Ser
                805                 810                 815

Phe Glu Val Tyr Ala Pro Cys Arg Thr Ala Val Val Tyr Ala Ala Val
                820                 825                 830

Asp Glu Arg Ser Ser Leu Val Pro Ile Gly Leu Leu Pro Glu Asp Val
                835                 840                 845

<210> SEQ ID NO 57
<211> LENGTH: 800
<212> TYPE: PRT
<213> ORGANISM: Arabidopsis thaliana

<400> SEQUENCE: 57

Arg Ser Ser Leu Thr Pro Arg Pro Thr Leu Pro Ser Arg Pro Leu Asn
1               5                   10                  15

Thr Gly Phe Asn Ala Gly Asn Ser Thr Leu Ser Phe Phe Lys Lys
                20                  25                  30

His Pro Leu Ser Arg Lys Ile Phe Ala Gly Lys Gln Ser Ala Glu Phe
            35                  40                  45

Asp Ser Ser Gln Ala Ile Ser Ala Ser Glu Lys Val Leu Val Pro
    50                  55                  60

Asp Asn Leu Asp Asp Asp Pro Arg Gly Phe Ser Gln Ile Phe Asp Leu
65              70                  75                  80

Glu Ser Gln Thr Met Glu Tyr Thr Glu Ala Val Arg Thr Glu Asp Gln
                85                  90                  95

Thr Met Asn Val Val Lys Glu Arg Gly Val Lys Pro Arg Ile Val Pro
            100                 105                 110

Pro Pro Gly Asp Gly Lys Lys Ile Tyr Glu Ile Asp Pro Met Leu Arg
        115                 120                 125

Thr Tyr Asn Asn His Leu Asp Tyr Arg Tyr Gly Gln Tyr Lys Arg Leu
    130                 135                 140

Arg Glu Glu Ile Asp Lys Tyr Glu Gly Gly Leu Glu Ala Phe Ser Arg
145                 150                 155                 160

Gly Tyr Glu Lys Leu Gly Phe Ser Arg Ser Asp Ala Gly Ile Thr Tyr
                165                 170                 175

Arg Glu Trp Ala Pro Gly Ala Lys Ala Ala Ser Leu Ile Gly Asp Phe
            180                 185                 190

Asn Asn Trp Asn Ser Asn Ala Asp Ile Met Thr Arg Asn Glu Phe Gly
        195                 200                 205

Val Trp Glu Ile Phe Leu Pro Asn Asn Thr Asp Gly Ser Pro Ala Ile
    210                 215                 220

Pro His Gly Ser Arg Val Lys Ile Arg Met Asp Thr Pro Ser Gly Ile
225                 230                 235                 240

Lys Asp Ser Ile Pro Ala Trp Ile Lys Phe Ser Val Gln Ala Pro Gly
                245                 250                 255

Glu Ile Pro Phe Asn Gly Ile Tyr Tyr Asp Pro Pro Glu Glu Glu Lys
            260                 265                 270

Tyr Val Phe Lys His Pro Gln Pro Lys Arg Pro Lys Ser Leu Arg Ile
        275                 280                 285
```

-continued

```
Tyr Glu Ala His Val Gly Met Ser Ser Thr Glu Pro Met Val Asn Thr
290                 295                 300
Tyr Ala Asn Phe Arg Asp Asp Val Leu Pro Arg Ile Lys Lys Leu Gly
305                 310                 315                 320
Tyr Asn Ala Val Gln Ile Met Ala Ile Gln Glu His Ser Tyr Tyr Ala
                325                 330                 335
Ser Phe Gly Tyr His Val Thr Asn Phe Phe Ala Pro Ser Ser Arg Cys
                340                 345                 350
Gly Thr Pro Glu Glu Leu Lys Ser Leu Ile Asp Arg Ala His Glu Leu
                355                 360                 365
Gly Leu Val Val Leu Met Asp Ile Val His Ser His Ala Ser Lys Asn
370                 375                 380
Thr Leu Asp Gly Leu Asn Met Phe Asp Gly Thr Asp Ala His Tyr Phe
385                 390                 395                 400
His Ser Gly Pro Arg Gly Tyr His Trp Met Trp Asp Ser Arg Leu Phe
                405                 410                 415
Asn Tyr Gly Ser Trp Glu Val Leu Arg Tyr Leu Leu Ser Asn Ala Arg
                420                 425                 430
Trp Ala Leu Glu Glu Tyr Lys Phe Asp Gly Phe Arg Phe Asp Gly Val
                435                 440                 445
Thr Ser Met Met Tyr Thr His His Gly Leu Ser Val Gly Phe Thr Gly
450                 455                 460
Asn Tyr Thr Glu Tyr Phe Gly Leu Glu Thr Asp Val Asp Ala Val Asn
465                 470                 475                 480
Tyr Leu Met Leu Val Asn Asp Met Ile His Gly Leu Tyr Pro Glu Ala
                485                 490                 495
Ile Thr Val Gly Glu Asp Val Ser Gly Met Pro Thr Phe Cys Asp Pro
                500                 505                 510
Val Gln Asp Gly Gly Val Gly Phe Asp Tyr Arg Leu His Met Ala Ile
                515                 520                 525
Ala Asp Lys Trp Ile Glu Met Leu Lys Lys Arg Asp Glu Asp Trp Gln
                530                 535                 540
Met Gly Asp Ile Ile Tyr Thr Leu Thr Asn Arg Arg Trp Ser Glu Lys
545                 550                 555                 560
Cys Ile Ser Tyr Ala Glu Ser His Asp Gln Ala Leu Val Gly Asp Lys
                565                 570                 575
Thr Ile Ala Phe Trp Leu Met Asp Lys Asp Met Tyr Asp Phe Met Ala
                580                 585                 590
Val Asp Arg Pro Ser Thr Pro Leu Ile Asp Arg Gly Ile Ala Leu His
                595                 600                 605
Lys Met Ile Arg Leu Ile Thr Met Gly Leu Gly Gly Glu Gly Tyr Leu
610                 615                 620
Asn Phe Met Gly Asn Glu Phe Gly His Pro Glu Trp Ile Asp Phe Pro
625                 630                 635                 640
Arg Gly Glu Gln Arg Leu Ser Asp Gly Ser Val Ile Pro Gly Asn Asn
                645                 650                 655
Phe Ser Tyr Asp Lys Cys Arg Arg Phe Asp Leu Gly Asp Ala Asp
                660                 665                 670
Tyr Leu Arg Tyr Arg Gly Leu Gln Glu Phe Asp Gln Ala Met Gln His
                675                 680                 685
Leu Glu Glu Asn Tyr Gly Phe Met Thr Ser Glu His Gln Phe Ile Ser
                690                 695                 700
Arg Lys Asp Glu Ala Asp Arg Val Ile Val Phe Glu Arg Gly Asp Leu
```

```
                          705                 710                 715                 720
            Val Phe Val Phe Asn Phe His Trp Thr Ser Ser Tyr Phe Asp Tyr Arg
                            725                 730                 735

Ile Gly Cys Ser Lys Pro Gly Lys Tyr Lys Ile Val Leu Asp Ser Asp
                            740                 745                 750

Asp Pro Leu Phe Gly Gly Phe Ser Arg Ile Asp Arg Ala Ala Glu Tyr
                            755                 760                 765

Phe Thr Tyr Asp Gly Leu Tyr Asp Glu Arg Pro Cys Ser Phe Met Val
                            770                 775                 780

Tyr Ala Pro Cys Arg Thr Ala Val Val Tyr Ala Leu Ala Asn His Asp
            785                 790                 795                 800

<210> SEQ ID NO 58
<211> LENGTH: 802
<212> TYPE: PRT
<213> ORGANISM: Zea mays

<400> SEQUENCE: 58

Met Ala Phe Ala Val Ser Gly Ala Val Leu Gly Gly Ala Val Arg Ala
  1               5                  10                  15

Pro Arg Leu Thr Gly Gly Glu Gly Ser Leu Val Phe Arg His Thr
                 20                  25                  30

Gly Leu Phe Leu Thr Arg Gly Ala Arg Val Gly Cys Ser Cys Thr His
                 35                  40                  45

Gly Ala Met Arg Ala Ala Ala Ala Arg Lys Ala Val Met Val Pro
             50                  55                  60

Glu Gly Glu Asn Asp Gly Leu Ala Ser Arg Ala Asp Ser Ala Gln Phe
 65                  70                  75                  80

Gln Ser Asp Glu Leu Glu Val Pro Asp Ile Ser Glu Thr Thr Cys
                 85                  90                  95

Gly Ala Gly Val Ala Asp Ala Gln Ala Leu Asn Arg Val Arg Val Val
                100                 105                 110

Pro Pro Pro Ser Asp Gly Gln Lys Ile Phe Gln Ile Asp Pro Met Leu
            115                 120                 125

Gln Gly Tyr Lys Tyr His Leu Glu Tyr Arg Tyr Ser Leu Tyr Arg Arg
            130                 135                 140

Ile Arg Ser Asp Ile Asp Glu His Glu Gly Gly Leu Glu Ala Phe Ser
145                 150                 155                 160

Arg Ser Tyr Glu Lys Phe Gly Phe Asn Arg Ser Ala Glu Gly Ile Thr
                165                 170                 175

Tyr Arg Glu Trp Ala Pro Gly Ala Phe Ser Ala Ala Leu Val Gly Asp
            180                 185                 190

Phe Asn Asn Trp Asp Pro Asn Ala Asp Arg Met Ser Lys Asn Glu Phe
            195                 200                 205

Gly Val Trp Glu Ile Phe Leu Pro Asn Asn Ala Asp Gly Thr Ser Pro
        210                 215                 220

Ile Pro His Gly Ser Arg Val Lys Val Arg Met Asp Thr Pro Ser Gly
225                 230                 235                 240

Ile Lys Asp Ser Ile Pro Ala Trp Ile Lys Tyr Ser Val Gln Ala Pro
                245                 250                 255

Gly Glu Ile Pro Tyr Asp Gly Ile Tyr Tyr Asp Pro Pro Glu Glu Val
            260                 265                 270

Lys Tyr Val Phe Arg His Ala Gln Pro Lys Arg Pro Lys Ser Leu Arg
            275                 280                 285
```

-continued

Ile Tyr Glu Thr His Val Gly Met Ser Ser Pro Glu Pro Lys Ile Asn
290                 295                 300

Thr Tyr Val Asn Phe Arg Asp Glu Val Leu Pro Arg Ile Lys Lys Leu
305                 310                 315                 320

Gly Tyr Asn Ala Val Gln Ile Met Ala Ile Gln Glu His Ser Tyr Tyr
            325                 330                 335

Gly Ser Phe Gly Tyr His Val Thr Asn Phe Phe Ala Pro Ser Ser Arg
            340                 345                 350

Phe Gly Thr Pro Glu Asp Leu Lys Ser Leu Ile Asp Arg Ala His Glu
        355                 360                 365

Leu Gly Leu Leu Val Leu Met Asp Val Val His Ser His Ala Ser Ser
370                 375                 380

Asn Thr Leu Asp Gly Leu Asn Gly Phe Asp Gly Thr Asp Thr His Tyr
385                 390                 395                 400

Phe His Ser Gly Pro Arg Gly His His Trp Met Trp Asp Ser Arg Leu
                405                 410                 415

Phe Asn Tyr Gly Asn Trp Glu Val Leu Arg Phe Leu Leu Ser Asn Ala
            420                 425                 430

Arg Trp Ala Leu Glu Glu Tyr Lys Phe Asp Gly Phe Arg Phe Asp Gly
        435                 440                 445

Val Thr Ser Met Met Tyr Thr His His Gly Leu Gln Val Thr Phe Thr
450                 455                 460

Gly Asn Phe Asn Glu Tyr Phe Gly Phe Ala Thr Asp Val Asp Ala Val
465                 470                 475                 480

Val Tyr Leu Met Leu Val Asn Asp Leu Ile His Gly Leu Tyr Pro Glu
                485                 490                 495

Ala Val Thr Ile Gly Glu Asp Val Ser Gly Met Pro Thr Phe Ala Leu
            500                 505                 510

Pro Val His Asp Gly Gly Val Gly Phe Asp Tyr Arg Met His Met Ala
        515                 520                 525

Val Ala Asp Lys Trp Ile Asp Leu Leu Lys Gln Ser Asp Glu Thr Trp
530                 535                 540

Lys Met Gly Asp Ile Val His Thr Leu Thr Asn Arg Arg Trp Leu Glu
545                 550                 555                 560

Lys Cys Val Thr Tyr Ala Glu Ser His Asp Gln Ala Leu Val Gly Asp
                565                 570                 575

Lys Thr Ile Ala Phe Trp Leu Met Asp Lys Asp Met Tyr Asp Phe Met
            580                 585                 590

Ala Leu Asp Arg Pro Ser Thr Pro Thr Ile Asp Arg Gly Ile Ala Leu
        595                 600                 605

His Lys Met Ile Arg Leu Ile Thr Met Gly Leu Gly Gly Glu Gly Tyr
610                 615                 620

Leu Asn Phe Met Gly Asn Glu Phe Gly His Pro Glu Trp Ile Asp Phe
625                 630                 635                 640

Pro Arg Gly Pro Gln Arg Leu Pro Ser Gly Lys Phe Ile Pro Gly Asn
                645                 650                 655

Asn Asn Ser Tyr Asp Lys Cys Arg Arg Phe Asp Leu Gly Asp Ala
            660                 665                 670

Asp Tyr Leu Arg Tyr His Gly Met Gln Glu Phe Asp Gln Ala Met Gln
        675                 680                 685

His Leu Glu Gln Lys Tyr Glu Phe Met Thr Ser Asp His Gln Tyr Ile
690                 695                 700

Ser Arg Lys His Glu Glu Asp Lys Val Ile Val Phe Glu Lys Glu Asp

-continued

```
             705                 710                 715                 720
Leu Val Phe Val Phe Asn Phe His Cys Asn Asn Ser Tyr Phe Asp Tyr
                    725                 730                 735
Arg Ile Gly Cys Arg Lys Pro Gly Val Tyr Lys Val Val Leu Asp Ser
                740                 745                 750
Asp Ala Gly Leu Phe Gly Gly Phe Ser Arg Ile His His Ala Ala Glu
            755                 760                 765
His Phe Thr Ala Asp Cys Ser His Asp Asn Arg Pro Tyr Ser Phe Ser
    770                 775                 780
Val Tyr Thr Pro Ser Arg Thr Cys Val Val Tyr Ala Pro Val Glu Pro
785                 790                 795                 800
Val Glu

<210> SEQ ID NO 59
<211> LENGTH: 828
<212> TYPE: PRT
<213> ORGANISM: Oryza sativa

<400> SEQUENCE: 59

Met Ala Ala Pro Ala Ser Ala Val Pro Gly Ser Ala Ala Gly Leu Arg
  1               5                  10                  15
Ala Gly Ala Val Arg Phe Pro Val Pro Ala Gly Ala Arg Ser Trp Arg
                 20                  25                  30
Ala Ala Ala Glu Leu Pro Thr Ser Arg Ser Leu Leu Ser Gly Arg Arg
             35                  40                  45
Phe Pro Gly Ala Val Arg Val Gly Gly Ser Gly Gly Arg Val Ala Val
         50                  55                  60
Arg Ala Ala Gly Ala Ser Gly Glu Val Met Ile Pro Glu Gly Glu Ser
 65                  70                  75                  80
Asp Gly Met Pro Val Ser Ala Gly Ser Asp Asp Leu Gln Leu Pro Ala
                 85                  90                  95
Leu Asp Asp Glu Leu Ser Thr Glu Val Gly Ala Glu Val Glu Ile Glu
            100                 105                 110
Ser Ser Gly Ala Ser Asp Val Glu Gly Val Lys Arg Val Val Glu Glu
        115                 120                 125
Leu Ala Ala Glu Gln Lys Pro Arg Val Val Pro Pro Thr Gly Asp Gly
    130                 135                 140
Gln Lys Ile Phe Gln Met Asp Ser Met Leu Asn Gly Tyr Lys Tyr His
145                 150                 155                 160
Leu Glu Tyr Arg Tyr Ser Leu Tyr Arg Arg Leu Arg Ser Asp Ile Asp
                165                 170                 175
Gln Tyr Glu Gly Gly Leu Glu Thr Phe Ser Arg Gly Tyr Glu Lys Phe
            180                 185                 190
Gly Phe Asn His Ser Ala Glu Gly Val Thr Tyr Arg Glu Trp Ala Pro
        195                 200                 205
Gly Ala His Ser Ala Ala Leu Val Gly Asp Phe Asn Asn Trp Asn Pro
    210                 215                 220
Asn Ala Asp Arg Met Ser Lys Asn Glu Phe Gly Val Trp Glu Phe Ile
225                 230                 235                 240
Leu Pro Asn Asn Ala Asp Gly Ser Ser Pro Ile Pro His Gly Ser Arg
                245                 250                 255
Val Lys Val Arg Met Glu Thr Pro Ser Gly Ile Lys Asp Ser Ile Pro
            260                 265                 270
Ala Trp Ile Lys Tyr Ser Val Gln Ala Ala Gly Glu Ile Pro Tyr Asn
```

```
                275                 280                 285
Gly Ile Tyr Tyr Asp Pro Pro Glu Glu Lys Tyr Ile Phe Lys His
    290                 295                 300
Pro Gln Pro Lys Arg Arg Lys Ser Leu Arg Ile Tyr Glu Thr His Val
305                 310                 315                 320
Gly Met Ser Ser Thr Glu Pro Lys Ile Asn Thr Tyr Ala Asn Phe Arg
                325                 330                 335
Asp Glu Val Leu Pro Arg Ile Lys Lys Leu Gly Tyr Asn Ala Val Gln
                340                 345                 350
Ile Met Ala Ile Gln Glu His Ala Tyr Tyr Gly Ser Phe Gly Tyr His
            355                 360                 365
Val Thr Asn Phe Phe Ala Pro Ser Ser Arg Phe Gly Thr Pro Glu Asp
    370                 375                 380
Leu Lys Ser Leu Ile Asp Lys Ala His His Leu Gly Leu Val Val Leu
385                 390                 395                 400
Met Asp Val Val His Ser His Ala Ser Asn Asn Thr Leu Asp Gly Leu
                405                 410                 415
Asn Gly Phe Asp Gly Thr Asp Thr His Tyr Phe His Ser Gly Ser Arg
            420                 425                 430
Gly His His Trp Met Trp Asp Ser Arg Leu Phe Asn Tyr Gly Asn Trp
        435                 440                 445
Glu Val Leu Arg Phe Leu Leu Ser Asn Ala Arg Trp Ala Leu Glu Glu
    450                 455                 460
Tyr Lys Phe Asp Gly Phe Arg Phe Asp Gly Val Thr Ser Met Met Tyr
465                 470                 475                 480
Thr His His Gly Leu Gln Val Ala Phe Thr Gly Asn Tyr Ser Glu Tyr
                485                 490                 495
Phe Gly Phe Ala Thr Asp Ala Asp Ala Val Val Tyr Leu Met Leu Val
                500                 505                 510
Asn Asp Leu Ile His Gly Leu Tyr Pro Glu Ala Ile Thr Ile Gly Glu
            515                 520                 525
Asp Val Ser Ser Met Pro Thr Phe Ala Leu Pro Val Gln Asp Gly Gly
    530                 535                 540
Val Gly Phe Asp Tyr Arg Leu His Met Ala Val Pro Asp Lys Trp Ile
545                 550                 555                 560
Glu Leu Leu Lys Gln Ser Asp Glu Ser Trp Lys Met Gly Asp Ile Val
                565                 570                 575
His Thr Leu Thr Asn Arg Arg Trp Ser Glu Lys Cys Val Thr Tyr Ala
            580                 585                 590
Glu Ser His Asp Gln Ala Leu Val Gly Asp Lys Thr Ile Ala Phe Trp
            595                 600                 605
Leu Met Asp Lys Asp Met Tyr Asp Phe Met Ala Leu Asp Arg Pro Ala
    610                 615                 620
Thr Pro Ser Ile Asp Arg Gly Ile Ala Leu His Lys Met Ile Arg Leu
625                 630                 635                 640
Ile Thr Met Gly Leu Gly Gly Glu Gly Tyr Leu Asn Phe Met Gly Asn
                645                 650                 655
Glu Phe Gly His Pro Glu Trp Ile Asp Phe Pro Arg Ala Pro Gln Val
                660                 665                 670
Leu Pro Asn Gly Lys Phe Ile Pro Gly Asn Asn Ser Tyr Asp Lys
            675                 680                 685
Cys Arg Arg Arg Phe Asp Leu Gly Asp Ala Asp Tyr Leu Arg Tyr Arg
    690                 695                 700
```

-continued

```
Gly Met Leu Glu Phe Asp Arg Ala Met Gln Ser Leu Glu Lys Tyr
705                 710                 715                 720

Gly Phe Met Thr Ser Asp His Gln Tyr Ile Ser Arg Lys His Glu Glu
            725                 730                 735

Asp Lys Met Ile Ile Phe Glu Lys Gly Asp Leu Val Phe Val Phe Asn
            740                 745                 750

Phe His Trp Ser Asn Ser Tyr Phe Asp Tyr Arg Val Gly Cys Leu Lys
            755                 760                 765

Pro Gly Lys Tyr Lys Val Val Leu Asp Ser Asp Ala Gly Leu Phe Gly
        770                 775                 780

Gly Phe Gly Arg Ile His His Thr Ala Glu His Phe Thr Ala Asp Cys
785                 790                 795                 800

Ser His Asp Asn Arg Pro Tyr Ser Phe Ser Val Tyr Ser Pro Ser Arg
                805                 810                 815

Thr Cys Val Val Tyr Ala Pro Ala Glu Pro Ala Glu
                820                 825
```

<210> SEQ ID NO 60
<211> LENGTH: 844
<212> TYPE: PRT
<213> ORGANISM: Manihot esculenta

<400> SEQUENCE: 60

```
Met Gly His Tyr Thr Ile Ser Gly Ile Arg Phe Pro Cys Ala Pro Leu
 1               5                  10                  15

Arg Lys Ser Gln Ser Thr Gly Phe His Gly Asp Arg Arg Thr Ser Ser
            20                  25                  30

Cys Leu Ser Phe Asn Phe Lys Lys Ala Ala Phe Ser Arg Arg Val Phe
        35                  40                  45

Ser Gly Lys Ser Ser His Glu Ser Asp Ser Ser Asn Val Met Val Thr
    50                  55                  60

Ala Ser Lys Arg Val Leu Pro Asp Gly Arg Ile Glu Cys Tyr Ser Ser
65                  70                  75                  80

Ser Thr Asp Gln Leu Glu Ala Pro Gly Thr Val Ser Glu Glu Ser Gln
                85                  90                  95

Val Leu Thr Asp Val Glu Ser Leu Ile Met Asp Asp Lys Ile Val Glu
            100                 105                 110

Asp Glu Val Asn Lys Glu Ser Val Pro Met Arg Glu Thr Val Ser Ile
        115                 120                 125

Gly Lys Ile Gly Ser Lys Pro Arg Ser Ile Pro Pro Gly Arg Gly
    130                 135                 140

Gln Arg Ile Tyr Asp Ile Asp Pro Ser Leu Thr Gly Phe Arg Gln His
145                 150                 155                 160

Leu Asp Tyr Arg Tyr Ser Gln Tyr Lys Arg Leu Arg Glu Glu Ile Asp
                165                 170                 175

Lys Tyr Glu Gly Ser Leu Asp Ala Phe Ser Arg Gly Tyr Glu Lys Phe
            180                 185                 190

Gly Phe Ser Arg Ser Glu Thr Gly Ile Thr Tyr Arg Glu Trp Ala Pro
        195                 200                 205

Gly Ala Thr Trp Ala Ala Leu Ile Gly Asp Phe Asn Asn Trp Asn Pro
    210                 215                 220

Asn Ala Asp Val Met Thr Gln Asn Glu Cys Gly Val Trp Glu Ile Phe
225                 230                 235                 240

Leu Pro Asn Asn Ala Asp Gly Ser Pro Pro Ile Pro His Gly Ser Arg
```

-continued

```
                245                 250                 255
Val Lys Ile Arg Met Asp Thr Pro Ser Gly Asn Lys Asp Ser Ile Pro
                260                 265                 270
Ala Trp Ile Lys Phe Ser Val Gln Ala Pro Gly Glu Leu Pro Tyr Asn
                275                 280                 285
Gly Ile Tyr Tyr Asp Pro Pro Glu Glu Lys Tyr Val Phe Lys Asn
                290                 295             300
Pro Gln Pro Lys Arg Pro Lys Ser Leu Arg Ile Tyr Glu Ser His Val
305                 310                 315                 320
Gly Met Ser Ser Thr Glu Pro Val Ile Asn Thr Tyr Ala Asn Phe Arg
                325                 330                 335
Asp Asp Val Leu Pro Arg Ile Lys Lys Leu Gly Tyr Asn Ala Val Gln
                340                 345                 350
Leu Met Ala Ile Gln Glu His Ser Tyr Tyr Ala Ser Phe Gly Tyr His
                355                 360                 365
Val Thr Asn Phe Tyr Ala Ala Ser Ser Arg Phe Gly Thr Pro Asp Asp
                370                 375             380
Leu Lys Ser Leu Val Asp Lys Ala His Glu Leu Gly Leu Leu Val Leu
385                 390                 395                 400
Met Asp Ile Val His Ser His Ala Ser Thr Asn Thr Leu Asp Gly Leu
                405                 410                 415
Asn Met Phe Asp Gly Thr Asp Gly His Tyr Phe His Ser Gly Pro Arg
                420                 425             430
Gly His His Trp Met Trp Asp Ser Arg Leu Phe Asn Tyr Gly Ser Trp
            435                 440                 445
Glu Val Leu Arg Phe Leu Leu Ser Asn Thr Arg Trp Trp Leu Asp Glu
450                 455                 460
Tyr Lys Phe Asp Gly Phe Arg Phe Asp Gly Val Thr Ser Met Met Tyr
465                 470                 475             480
Thr His His Gly Leu Gln Val Asp Phe Thr Gly Asn Tyr Asn Glu Tyr
                485                 490                 495
Phe Gly Tyr Ala Thr Asp Val Asp Ala Val Val Tyr Leu Met Leu Leu
                500                 505             510
Asn Asp Met Ile His Gly Leu Phe Pro Glu Ala Val Thr Ile Gly Glu
            515                 520                 525
Asp Val Ser Gly Met Pro Thr Val Cys Ile Pro Val Glu Asp Gly Gly
            530                 535             540
Val Gly Phe Asp Tyr Arg Leu His Met Ala Val Ala Asp Lys Trp Val
545                 550                 555                 560
Glu Ile Ile Gln Lys Arg Asp Glu Asp Trp Lys Met Gly Asp Ile Val
                565                 570                 575
His Met Leu Thr Asn Arg Arg Trp Leu Glu Lys Cys Val Ser Tyr Ala
                580                 585             590
Glu Ser His Asp Gln Ala Leu Val Gly Asp Lys Thr Ile Ala Phe Trp
            595                 600                 605
Leu Met Asp Lys Asp Met Tyr Asp Phe Met Ala Arg Asp Arg Pro Ser
610                 615                 620
Thr Pro Leu Ile Asp Arg Gly Ile Ala Leu His Lys Met Ile Arg Leu
625                 630                 635                 640
Ile Thr Met Gly Leu Gly Gly Glu Gly Tyr Leu Asn Phe Met Gly Asn
                645                 650                 655
Glu Phe Gly His Pro Glu Trp Ile Asp Phe Pro Arg Gly Asp Arg His
                660                 665                 670
```

-continued

```
Leu Pro Asn Gly Lys Val Ile Pro Gly Asn Asn His Ser Tyr Asp Lys
        675                 680                 685

Cys Arg Arg Arg Phe Asp Leu Gly Asp Ala Asp Tyr Leu Arg Tyr His
        690                 695                 700

Gly Met Gln Glu Phe Asp Gln Ala Met Gln His Leu Glu Glu Ala Tyr
705                 710                 715                 720

Gly Phe Met Thr Ser Glu His Gln Tyr Ile Ser Arg Lys Asp Glu Gly
                725                 730                 735

Asp Arg Ile Ile Val Phe Glu Arg Gly Asn Leu Val Phe Val Phe Asn
            740                 745                 750

Phe His Trp Thr Asn Ser Tyr Ser Asp Tyr Arg Val Gly Cys Phe Lys
        755                 760                 765

Ser Gly Lys Tyr Lys Ile Val Leu Asp Ser Asp Asp Gly Leu Phe Gly
        770                 775                 780

Gly Phe Asn Arg Leu Ser His Asp Ala Glu His Phe Thr Phe Asp Gly
785                 790                 795                 800

Trp Tyr Asp Asn Arg Pro Arg Ser Phe Met Val Tyr Ala Pro Ser Arg
                805                 810                 815

Thr Ala Val Val His Ala Leu Val Glu Asp Glu Glu Asn Glu Ala Glu
                820                 825                 830

Asn Glu Val Glu Ser Glu Val Lys Pro Ala Ser Gly
            835                 840
```

What is claimed is:

1. An isolated nucleic acid from cassava, or its complement, wherein the isolated nucleic acid encodes a polypeptide having starch branching enzyme Class A (SBEII) activity and the amino acid sequence of SEQ ID NO: 29.

2. The isolated nucleic acid according to claim 1, or its complement, wherein the isolated nucleic acid comprises the nucleic acid sequence of SEQ ID NO: 28.

3. The isolated nucleic acid according to claim 2, wherein the nucleic acid further comprises a 5' and/or a 3' untranslated region.

4. The isolated nucleic acid according to claim 1, or its complement, wherein the isolated nucleic acid comprises nucleotides 21–2531 of the nucleic acid sequence of SEQ ID NO: 28.

5. A construct comprising a nucleic acid from cassava, wherein said nucleic acid has at least 88% sequence identity to SEQ ID NO: 28 and wherein said nucleic acid encodes a protein with SBE II activity.

6. The construct of claim 5, further comprising a promoter operable in plants, wherein said promoter is operably linked to the nucleic acid.

7. The construct of claim 6, wherein the nucleic acid is in the sense or the anti-sense orientation.

8. A plant cell, plant tissue, or plant comprising the construct of claim 5 or 6.

9. A method of producing a transformed cassava plant, wherein the method comprises introducing into a cell of a cassava plant the construct of claim 5 or 6 to produce a transformed cassava cell and regenerating a transformed cassava plant from the transformed cassava cell.

10. A method of producing a transformed progeny cassava plant, wherein the method comprises introducing into a cell of a cassava plant a construct comprising a nucleic acid from cassava to produce a transformed cassava cell, wherein said nucleic acid has at least 88% sequence identity to SEQ ID NO: 28 and wherein said nucleic acid encodes a protein with SBE II activity; regenerating a transformed cassava plant from the transformed cassava cell; sexually crossing the transformed cassava plant with a second cassava plant, wherein the second cassava plant is not transformed with said nucleic acid; harvesting the resultant seed; growing the harvested seed; and selecting a transformed cassava progeny plant which comprises the nucleic acid.

* * * * *